(12) United States Patent
Tamura et al.

(10) Patent No.: US 10,406,243 B2
(45) Date of Patent: Sep. 10, 2019

(54) METHODS OF TREATMENT COMPRISING A POLYROTAXANE AND MEDICINAL COMPOSITION

(71) Applicant: National University Corporation Tokyo Medical and Dental University, Tokyo (JP)

(72) Inventors: Atsushi Tamura, Tokyo (JP); Nobuhiko Yui, Tokyo (JP)

(73) Assignee: National University Corporation Tokyo Medical and Dental University, Tokyo (JP)

(*) Notice: Subject to any disclaimer, the term of this patent is extended or adjusted under 35 U.S.C. 154(b) by 526 days.

(21) Appl. No.: 14/913,978

(22) PCT Filed: Aug. 18, 2014

(86) PCT No.: PCT/JP2014/071553
§ 371 (c)(1),
(2) Date: Feb. 23, 2016

(87) PCT Pub. No.: WO2015/025815
PCT Pub. Date: Feb. 26, 2015

(65) Prior Publication Data
US 2016/0199512 A1 Jul. 14, 2016

(30) Foreign Application Priority Data
Aug. 23, 2013 (JP) .................................. 2013-172994

(51) Int. Cl.
*A61K 9/00* (2006.01)
*A61K 47/69* (2017.01)

(52) U.S. Cl.
CPC ........ *A61K 47/6951* (2017.08); *A61K 9/0085* (2013.01)

(58) Field of Classification Search
CPC ............ A61K 47/6951; C08B 37/0015; C08B 37/0012
See application file for complete search history.

(56) References Cited

U.S. PATENT DOCUMENTS

2004/0162275 A1* 8/2004 Yui ...................... A61K 31/724
514/183

FOREIGN PATENT DOCUMENTS

| JP | 2009-518418 A | 5/2009 |
| WO | 2007/067602 A1 | 12/2006 |
| WO | 2007/067602 A1 | 6/2007 |
| WO | 2014182804 A1 | 11/2014 |

OTHER PUBLICATIONS

Aqul, A. et al., The Journal of Neuroscience, "Unesterified Cholesterol Accumulation in Late Endosomes/Lysosomes Causes Neurodegeneration and is Prevented by Driving Cholesterol Export from This Compartment", 2011, vol. 31, No. 25, pp. 9404-9413 (Year: 2011).*
Li, J.J. et al., Appl. Microbiol Biotechnol., "Polyrotaxanes for applications in life science and biotechnology", 2011, vol. 90, pp. 427-443 (Year: 2011).*
Santos-Lozano, A. et al., Ann Transl Med, "Niemann-Pick disease treatment: a systematic review of clinical trials", 2015, vol. 3, No. 22, 9 pages (Year: 2015).*
EP14838693.1 , "Extended European Search Report", dated Apr. 19, 2017, 8 pages.
Tamura et al., "Lysosomal-specific Cholesterol Reduction by Biocleavable Polyrotaxanes for Ameliorating Niemann-Pick Type C Disease," Scientific Reports, vol. 4, Mar. 12, 2014, 8 pages.
Brewster et al., "Cyclodextrins as pharmaceutical solubilizers", Advanced Drug Delivery Reviews 59 (2007), pp. 645-666.
Liu et al., "Reversal of defective lysosomal transport in NPC disease ameliorates liver dysfunction and neurodegeneration in the npc1−/− mouse", Proc. Natl. Acad. Sci. U.S.A. vol. 106 (7) (2009), pp. 2377-2382.
Frijlink et al., "The Pharmacokinetics of β-Cyclodextrin and Hydroxypropyl-β-cyclodexrin in the Rat", Pharmaceutical Research, vol. 7 (12), (1990), pp. 1248-1252.
Irie et al., "Pharmaceutical Applications of Cyclodextrins. III. Toxicological Issues and Safety Evaluation", Journal of Pharmaceutical Sciences vol. 86 (2) (1997), pp. 147-162.
Lieberman et al., "Autophagy in lysosomal storage disorders", Autophagy 8(5) (2012), pp. 719-730.
Ishibashi et al., "Association of autophagy with cholesterol-accumulated compartments in Niemann-Pick disease type C cells", Journal of Clinical Neuroscience 16 (2009), pp. 954-959.
Cuervo, "Autophagy: in sickness and in health", TRENDS in Cell Biology vol. 14 (2) (2004), pp. 70-77.
Collins et al., "Synthesis, Characterization, and Evaluation of Pluronic-Based β-Cyclodextrin Polyrotaxans for Mobilization of Accumulated Cholesterol from Niemann-Pick Type C Fibroblasts", Biochemistry vol. 52 (2013), pp. 3242-3253.
Yui et al., "Functional Cyclodextrin Polyrotaxanes for Drug Delivery", Adv Polym Sci (2009), pp. 55-77.
International Application No. PCT/JP2014/071553, International Preliminary Report on Patentability, dated Feb. 25, 2016.
Yamashita et al., "Supramolecular control of polyplex dissociation and cell transfection: Efficacy of amino groups and threading cyclodextrins in biocleavable polyrotaxanes", Journal of Controlled Release, Jul. 17, 2008, vol. 131, pp. 137-144.
Tamura et al., "Molecular logistics using cytocleavable polyrotaxanes for the reactivation of enzymes delivered in living cells", Scientific Reports, 3, 2252 (2013).

(Continued)

*Primary Examiner* — Shaojia A Jiang
*Assistant Examiner* — Bahar Craigo
(74) *Attorney, Agent, or Firm* — Kilpatrick Townsend & Stockton LLP

(57) ABSTRACT

A medicinal composition for diseases caused by dyslipidemia and/or autophagy dysfunction, etc., said medicinal composition comprising polyrotaxane that carries bulky substituents introduced, via intracellularly degradable bonds, into both ends of a linear molecule penetrating through plural cyclic molecules.

9 Claims, 24 Drawing Sheets

(56) References Cited

OTHER PUBLICATIONS

Tamura et al., "Cellular internalization and gene silencing of siRNA polyplexes by cytocleavable cationic polyrotaxanes with tailored rigid backbones", Biomaterials, 34, 2480-2491 (2013).
Tamura et al., "A supramolecular endosomal escape approach for enhancing gene silencing of siRNA using acid-degradable cationic polyrotaxanes", J. Mater. Chem. B, 2013, 1, 3535-3544.
Dan et al., "One-Pot Synthesis of an Acid-Labile Amphiphilic Triblock Copolymer and its pH-Responsive Vesicular Assembly", Angew. Chem. Int. Ed. 2013, 52, 7300-7305.
Dan et al., "Aggregation and pH Responsive Disassembly of a New Acid-Labile Surfactant Synthesized by Thiol-Acrylate Michael Addition Reaction", Langmuir 2011, 27(2), 612-617.
Elbert et al., "Protein delivery from materials formed by self-selective conjugate addition reactions", Journal of Controlled Release 76 (2001) 11-25.
Oishi et al., "pH-Responsive Oligodeoxynucleotide (ODN)-Poly(Ethylene Glycol) Conjugate through Acid-Labile β-Thiopropionate Linkage: Preparation and Polyion Complex Micelle Formation", Biomacromolecules 2003, 4, 1426-1432.

* cited by examiner

METHODS OF TREATMENT COMPRISING A POLYROTAXANE AND MEDICINAL COMPOSITION

CROSS-REFERENCE TO RELATED APPLICATIONS

The present application is the U.S. national stage of PCT/JP2014/071553, filed Aug. 18, 2014, which claims benefit of priority to Japanese Patent Application No. 2013-172994, filed Aug. 23, 2013, both of which are incorporated by reference herein in their entirety.

BACKGROUND OF THE INVENTION

Technical Field

The present invention relates to pharmaceutical compositions for treating a disorder caused by at least one of lipid metabolism disorders and autophagy dysfunctions, which include a polyrotaxane, and to novel polyrotaxanes.

Background Art

Disorders in which lipids, sugar, cholesterol etc. are accumulated in lysosomes due to genetic deficiency or genetic mutation of membrane transport proteins or catabolic enzymes in lysosomes are collectively called as lysosomal diseases. About 30 types of lysosomal diseases have been designated as specified diseases in Japan, and it has been known that few effective remedies are available.

In Niemann-Pick Type C (hereinafter, sometimes referred to as "NPC disease") which is one of the lysosomal diseases, for example, cholesterol and lipids are accumulated in lysosomes due to mutation of NPC1 which is a membrane protein. The NPC disease develops from childhood, manifesting symptoms such as progressive neurological dysfunction and hepatosplenomegaly, and is an intractable metabolic disorder causing death at around age of 10 in many cases.

In recent years, use of cyclodextrins has been held as a promising remedy for the NPC disease. Cyclodextrins are cyclic sugars, and are named, depending on the number of repetitions of sugar, as α-cyclodextrin (number of repetitions: 6), β-cyclodextrin (number of repetitions: 7), and γ-cyclodextrin (number of repetitions: 8). These cyclodextrins are known to include various compounds in the cavity, and particularly, β-cyclodextrin is known to have a superior ability to include cholesterol (for example, refer to Non-Patent Literature 1). In recent years, it has been revealed that the amount of cholesterol in cells decreases by allowing β-cyclodextrin modified by hydroxypropyl groups (hereinafter, sometimes referred to as "HP-β-CD") to act on NPC disease patient-derived cells. Furthermore, it has been discovered that administering HP-β-CD to Npc1-deficient mice (Npc1$^{-/-}$ mice) decreases the amount of cholesterol accumulated in each tissue, and extends the survival (for example, refer to Non-Patent Literature 2). Thus, β-cyclodextrin, which is capable of decreasing the cholesterol accumulated in cells, has been attracting attention as a novel remedy for the NPC disease. Particularly, compassionate use being approved in the United States, and phase I trial of a remedy for the NPC disease being started from the year 2012, it has been considered to be a medicine having an extremely high degree of expectations.

On the other hand, cyclodextrins (hereinafter, sometimes referred to as "CD"), being a low-molecular compound with a molecular weight of about 1,000, have a short blood half-life of about a few tens of minutes, and have problems such as rapid renal excretion immediately after administering, and low cell membrane permeability (for example, refer to Non-Patent Literature 3). Therefore, to have a sufficient therapeutic effect, it is necessary to administer repetitively a highly concentrated CD (the amount administered to the Npc1-deficient mice was 4,000 mg/kg; for example, refer to Non-Patent Literature 2). However, since highly concentrated CD shows hemolytic activity and causes tissue damage, use of highly concentrated CD is a matter of concern due to side effects such as a damage to normal tissues (for example, refer to Non-Patent Literature 4). Therefore, achieving a sufficient therapeutic effect non-invasively on human beings is considered to be difficult.

Consequently, in the present circumstances, a rapid development of a pharmaceutical composition with a high safety, having a superior cholesterol removing effect, and having a high therapeutic effect or a preventive effect on lysosomal diseases including Niemann-Pick Type C, is eagerly sought.

Moreover, it has been revealed in recent years that the lysosomal diseases are not only metabolism disorders of lipids, but are disorders of autophagy which plays a role in protein degradation in cells (for example, refer to Non-Patent Literature 5). In autophagy, organelles such as mitochondria and proteins which have become unnecessary in cells are degraded by lysosomes, but the abnormality in the autophagy function leads to accumulation of unnecessary proteins in cells. It has also been indicated that the disordered function of autophagy is associated with the pathology of lysosomal diseases. Particularly, in NPC disease, it has been shown that autophagosomes accumulate in the cytoplasm (for example, refer to Non-Patent Literature 6). Such an accumulation of autophagosomes indicates that the unnecessary proteins and organelles, which should have been degraded by lysosomes normally, are accumulated in the cytoplasm.

Moreover, as other disorders which show impaired proteolysis in autophagy, neurodegenerative disorders such as Alzheimer's disease, Parkinson's disease, and Huntington's disease have been identified (for example, refer to Non-Patent Literature 7).

Consequently, in the present circumstances, a rapid development of a pharmaceutical composition having a high therapeutic effect or preventive effect on disorders caused due to the autophagy dysfunction, including lysosomal diseases, is also eagerly sought.

CITATION LIST

Non-Patent Literature

Non-Patent Literature 1: M. E. Brewster et al. Adv. Drug Deliv. Rev. 59(7), 645-666 (2007)
Non-Patent Literature 2: B. Liu et al. Proc. Natl. Acad. Sci. U.S.A. 106(7), 2377-2382 (2009)
Non-Patent Literature 3: H. W. Frijlink et al. Pharm. Res. 7(12), 1248-1252 (1990)
Non-Patent Literature 4: T. Irie et al. J. Pharm. Sci. 86(2), 147-162 (1997)
Non-Patent Literature 5: A. P. Lieberman et al. Autophagy 8(5), 719-730 (2012)
Non-Patent Literature 6: S. Ishibashi et al. J. Clin. Neurosci. 16(7), 954-959 (2009)
Non-Patent Literature 7: A. M. Cuervo Trends Cell Biol. 14(2), 70-77 (2004)

BRIEF SUMMARY OF THE INVENTION

Technical Problem

The problem to be solved by the present invention is to resolve the above-mentioned various problems, so as to achieve the following object. Namely, an object of the present invention is to provide a pharmaceutical composition with a high safety, having at least one of the superior cholesterol removing effect and superior effect of enhancing formation of autolysosomes, and having a high therapeutic effect or preventive effect on disorders caused due to at least one of lipid metabolism disorders and autophagy dysfunctions, as well as to provide polyrotaxane compounds which can be used suitably in the pharmaceutical composition.

Solution to Problem

Means to Solve the Problem are as Follows

<1> A pharmaceutical composition for a disease caused by at least any one of lipid metabolism disorders and autophagy dysfunctions, comprising a polyrotaxane having a plurality of cyclic molecules threaded by a linear molecule, wherein the linear molecule is linked to bulky substituents via intracellularly degradable linkages at both ends.
<2> A polyrotaxane comprising a plurality of cyclic molecules threaded by a linear molecule,
wherein the linear molecule is linked to bulky substituents via intracellularly degradable linkages at both ends,
wherein the linear molecule is a copolymer composed of polyethylene glycol and polypropylene glycol in the order of polyethylene glycol-polypropylene glycol-polyethylene glycol, and
wherein the plurality of cyclic molecules are β-cyclodextrins.

Advantageous Effects of Invention

According to the present invention, a variety of conventional problems as described above can be solved to achieve the above-mentioned object, and a pharmaceutical composition with a high safety, having at least either one of a superior cholesterol removing effect and a superior effect of enhancing formation of autolysosomes, and having a high therapeutic effect or a preventive effect on disorders caused due to at least one of lipid metabolism disorders and autophagy dysfunctions, as well as polyrotaxanes which can be used favorably in the pharmaceutical composition, can be provided.

DETAILED DESCRIPTION OF THE INVENTION

Figure 1:
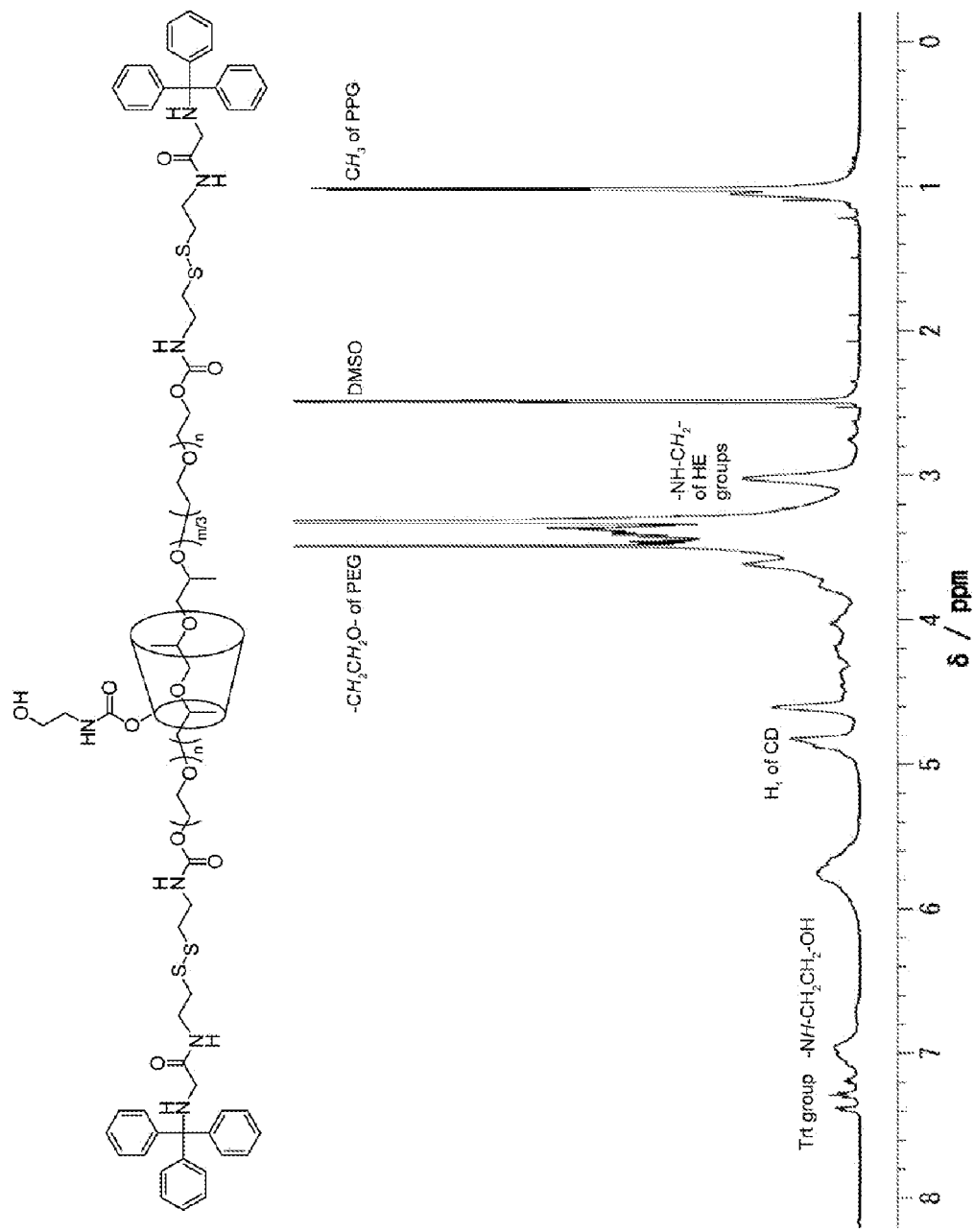
FIG. 1 is a proton nuclear magnetic resonance spectrum at 500 MHz, measured in deuterated dimethyl sulfoxide, of a polyrotaxane obtained in Preparation Example 1. Horizontal axis: unit in ppm.

Description of Embodiments
(Pharmaceutical Composition)

A pharmaceutical composition of the present invention is a pharmaceutical composition for a disorder caused by at least one of lipid metabolism disorders and autophagy dysfunctions.

The pharmaceutical composition of the present invention includes at least a polyrotaxane, and further includes other ingredients as necessary.

<Pol5yrotaxane>

The polyrotaxane is not particularly limited, provided that it is a polyrotaxane having a plurality of cyclic molecules threaded by a linear molecule that has bulky substituents via intracellularly degradable linkages at both ends, and can be appropriately selected according to the purpose.

One kind of polyrotaxane may be used alone, or two or more kinds of polyrotaxanes may be used in combination.

The number average molecular weight of the polyrotaxane is not particularly limited, and can be appropriately selected according to the object. It is preferable, however, that an average molecular weight of the polyrotaxane is in a range of about 20,000 to 100,000.

——Linear Molecule——

The linear molecule penetrates through a plurality of cyclic molecules, and has intracellularly degradable linkages at its two end portions. The linear molecule is linked with bulky substituents via the intracellularly degradable linkages.

The linear molecule is not particularly limited and can be appropriately selected according to the object, provided that the linear molecule penetrates the cavity of the plurality of cyclic molecules, and can maintain that state, and has intracellularly degradable linkages at both end portions.

An element other than the two end portions of the linear molecule can be appropriately selected from known polyrotaxane elements, which include polyethylene glycol, polypropylene glycol, a copolymer of polyethylene glycol and polypropylene glycol, polymethyl vinyl ether, polyethylene imine, polyamino acids and the like.

There is no particular restriction on the molecular weight of the element other than the two end portions of the linear molecule, and the molecular weight can be appropriately selected according to the molecular weight of the target polyrotaxane and the number of cyclic molecules to be threaded.

For these, chemically synthesized products or marketed products may be used.

It is preferable to appropriately select the elements other than the two end portions of the linear molecule depending on the cyclic molecule to be combined as described later. For example, in a case in which the cyclic molecule is α-cyclodextrin, polyethylene glycol is preferable, and in a case in which the cyclic molecule is β-cyclodextrin, polypropylene glycol or a copolymer of polyethylene glycol and polypropylene glycol is preferable.

As for the copolymer of polyethylene glycol and polypropylene glycol, it is preferable that polyethylene glycol and polypropylene glycol are polymerized in the order of polyethylene glycol, polypropylene glycol, and polyethylene glycol.

The number average molecular weight of a polyethylene glycol moiety in the copolymer of polyethylene glycol and polypropylene glycol is not particularly limited, and can be appropriately selected according to the object. The number average molecular weight of the polyethylene glycol moiety can be in a range of 500 to 10,000 for example. Moreover, the number average molecular weight of a polypropylene glycol moiety in the copolymer of polyethylene glycol and polypropylene glycol is not particularly limited, and can be appropriately selected according to the object. The number average weight of the polypropylene glycol moiety can be in a range of 500 to 5,000 for example.

Specific examples of the copolymer of polyethylene glycol and polypropylene glycol include Pluronic and the like.

——Intracellularly Degradable Linkage——

The intracellularly degradable linkage is not particularly limited, provided that the linkage is degradable in a cell, and can be appropriately selected according to the object. Examples of the intracellularly degradable linkage include an acetal linkage, a ketal linkage, a disulfide linkage, an ester linkage, an ortho ester linkage, a vinyl ether linkage, a hydrazide linkage, an amide linkage and the like. Among these, from a viewpoint of being superior for intracellularly selective degradation, the acetal linkage, the ketal linkage, the disulfide linkage, the ester linkage, the ortho ester linkage, the vinyl ether linkage, and the hydrazide linkage are preferable, and the disulfide linkage is more preferable.

One kind of them may be used alone, or two or more kinds may be used in combination.

The method for forming the intracellularly degradable linkages are not particularly limited, and any known method may be used appropriately. Examples of the methods include methods similar to those described in "Journal of Controlled Release 76 (2001) 11-25," "Biomacromolecules 2003, 4, 1426-1432," "Langmuir 2011, 27(2), 612-617," "Angew. Chem. Int. Ed. 2013, 52, 7300-7305," "J. Mater. Chem. B, 2013, 1, 3535-3544," "Biomaterials, 34, 2480-2491 (2013)," "Scientific Reports, 3, 2252 (2013)" and the like.

—Cyclic Molecules—

The cyclic molecules are not particularly limited, and can be selected according to the object. The examples of cyclic molecules include cyclodextrin, crown ether, cyclofructan, calixarene, and the like. Among these, from a viewpoint of being superior in ability to include cholesterol, cyclodextrin is preferable.

One kind of them may be used alone, or two or more kinds may be used in combination.

The cyclodextrin is not particularly limited, and can be appropriately selected according to the object. Examples of cyclodextrin include α-cyclodextrin, β-cyclodextrin, and γ-cyclodextrin. Among these, α-cyclodextrin and β-cyclodextrin are preferable, and from a viewpoint of being superior in ability to include cholesterol, β-cyclodextrin is more preferable.

The number of cyclic molecules per one molecule of polyrotaxane is not particularly limited, and can be appropriately selected according to the object. On average 5 to 200 cyclic molecules are preferable.

The cyclic molecules may be modified or may not be modified with a substituent group, and for improving water solubility of the polyrotaxane, it is preferable that the cyclic molecules are modified with a substituent group.

The position to be modified is not particularly limited, provided that it improves the water solubility of polyrotaxane, and can be appropriately selected according to the object. In a case of cyclodextrin, for example, it is preferable that the hydroxyl group is modified.

The substituent group is not particularly limited, and can be appropriately selected according to the object. Examples of the substituent group include a hydroxyethyl group, a hydroxypropyl group, a hydroxybutyl group, a hydroxyethoxyethyl group, a methyl group, an N,N-dimethyl aminoethyl group (sometimes referred to as "DMAE" group), a carboxyl group, a primary amino group, peptide molecules, water-soluble polymers such as polyethylene glycol, and the like. Among these, from a viewpoint of ability to improve an efficiency of uptake of polyrotaxane into cells, the DMAE group is preferable.

The hydroxyl group may be modified directly with the substituent, or may be modified via a linker.

The linker is not particularly limited, and can be appropriately selected according to the object. Examples of the linker include a carbamic ester linkage (—O—CO—NH—), an ester linkage (—O—CO—), a carbonate linkage (—O—CO—O—), and an ether linkage (—O—).

The number of modifications with the substituent per one molecule of polyrotaxane is not particularly limited, and can be appropriately selected according to the object. On average 10 to 400 modifications with the substituent are preferable.

The method for making the cyclic molecules threaded by the linear molecule is not particularly limited, and can be appropriately selected from known methods.

The method for modifying the cyclic molecules is also not particularly limited, and can be appropriately selected from known methods.

—Bulky Substituent—

The bulky substituent is not particularly limited, provided that it is capable of preventing detachment of the plurality of cyclic molecules by capping both ends of the linear molecule, and can be appropriately selected according to the object. Examples of bulky substituent include amino acids or derivatives thereof, oligopeptides, fluorescent molecules, and the like. Among these, N-trityl glycine is preferable from a viewpoint of hydrolysis-resistance under physiological conditions.

The method for linking the bulky substituent groups with the linear molecule is not particularly limited, and can be appropriately selected from known methods.

It is preferable that a polyrotaxane in the pharmaceutical composition is the polyrotaxane according to the present invention.

The polyrotaxane of the present invention is a polyrotaxane comprising a plurality of cyclic molecules threaded by a linear molecule, wherein the linear molecule is linked to bulky substituents via intracellularly degradable linkages at both ends, wherein the linear molecule is a copolymer composed of polyethylene glycol and polypropylene glycol in the order of polyethylene glycol-polypropylene glycol-polyethylene glycol, and wherein the plurality of cyclic molecules are β-cyclodextrins.

The cyclic molecules and the linear molecule in the polyrotaxane of the present invention, and the intracellularly degradable linkages and the bulky substituents in the linear molecule are similar to those described for the polyrotaxane in the pharmaceutical composition, and the preferred embodiments are also similar.

More preferable embodiments of the polyrotaxane of the present invention include a polyrotaxane represented by following Structural Formula (1), a polyrotaxane represented by following Structural Formula (2), a polyrotaxane represented by following Structure Formula (4), a polyrotaxane represented by following Structural Formula (5), and a polyrotaxane represented by following Structural Formula (6).

Structural Formula (1)

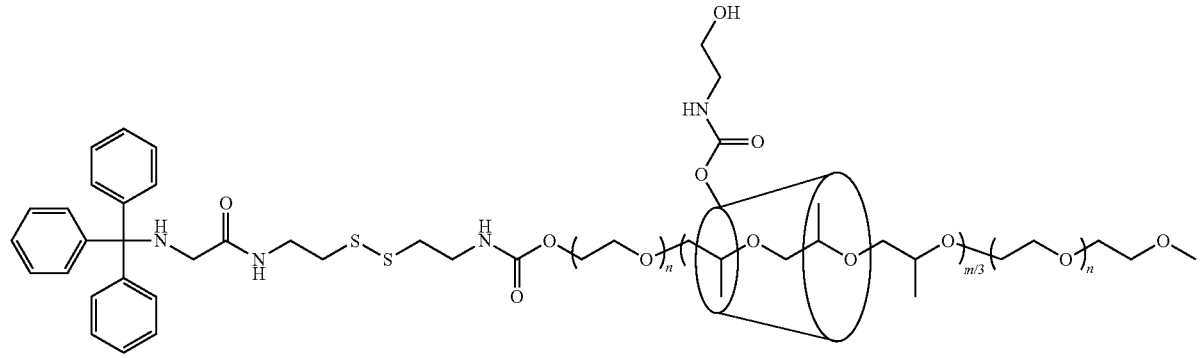

-continued
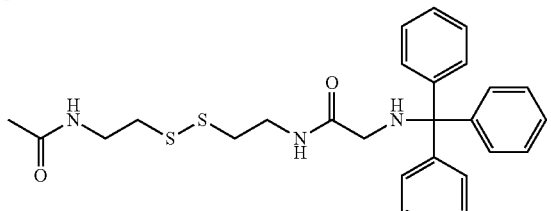
Structural Formula (2)
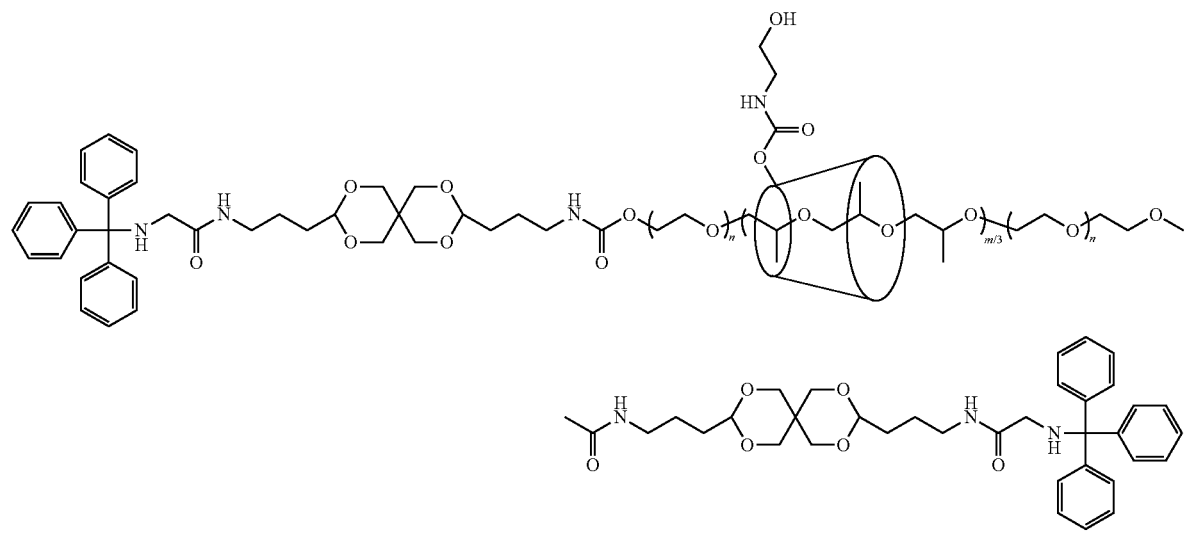
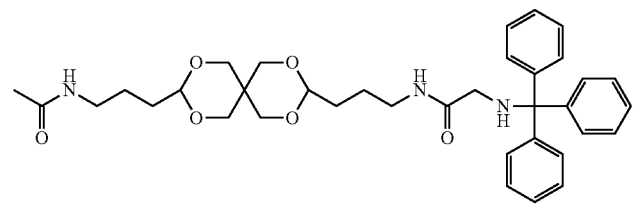
Structural Formula (4)
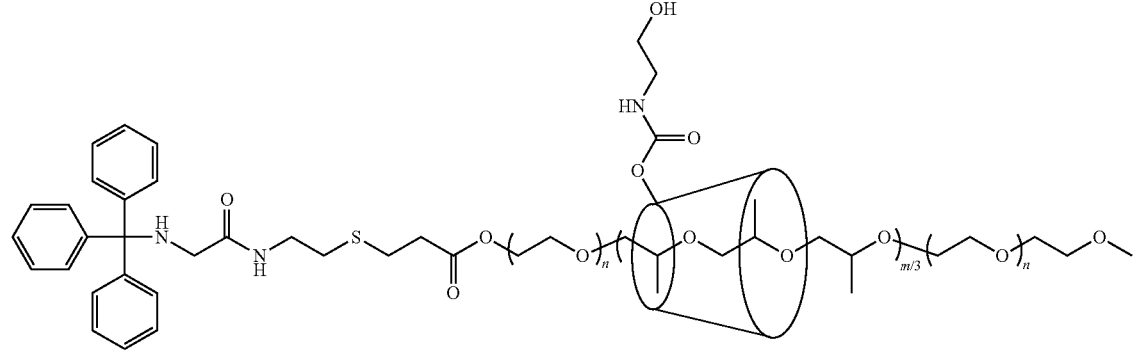
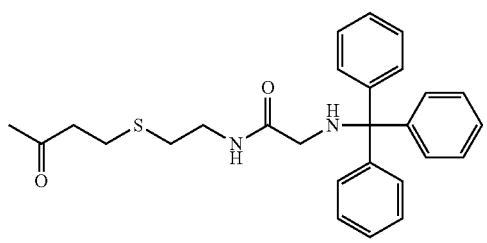

Structural Formula (5)

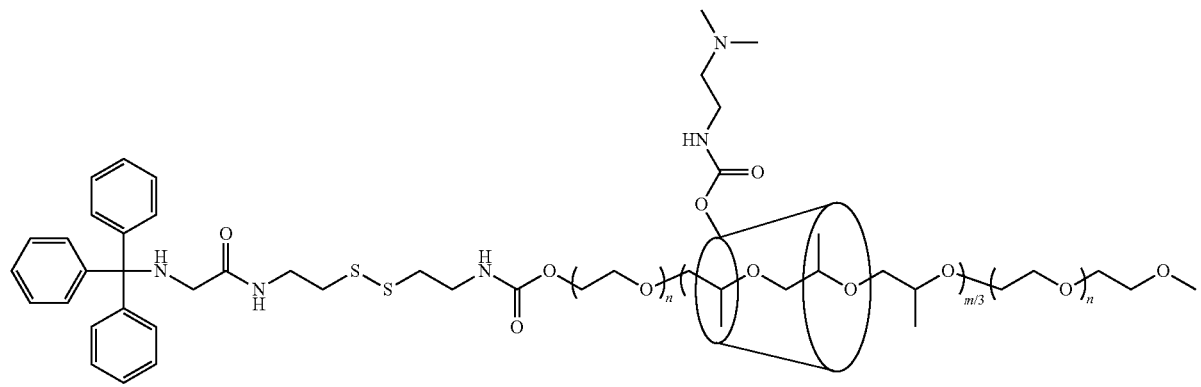

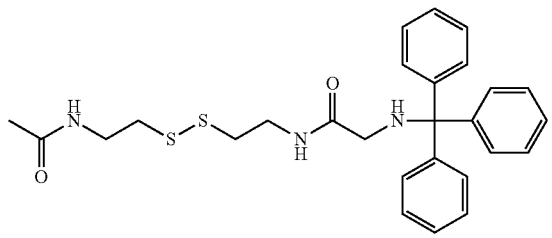

Structural Formula (6)

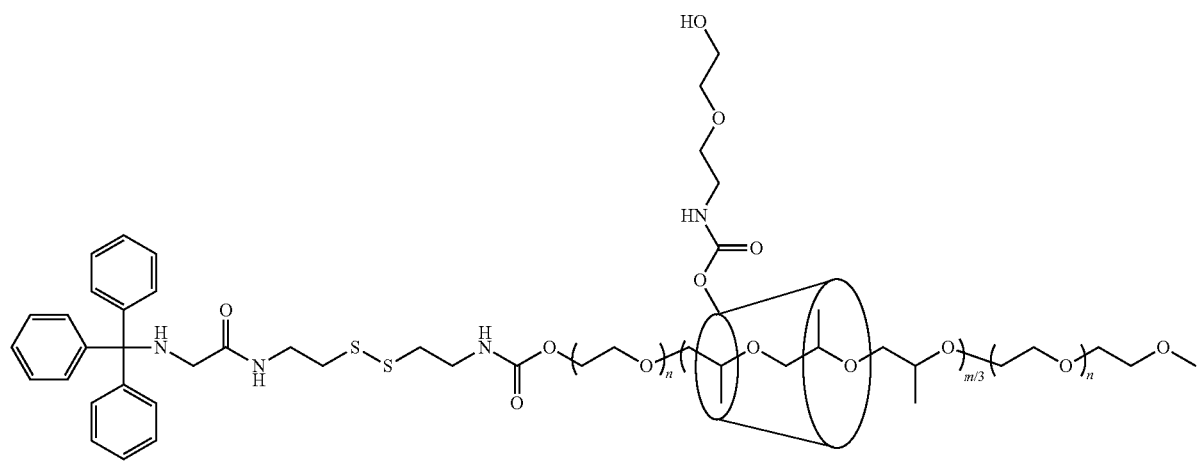

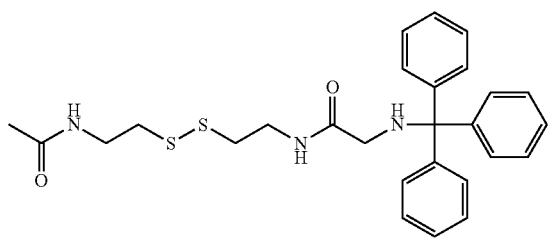

The linear molecule of the polyrotaxane represented by Structural Formula (1), (2), (4), (5), or (6) is a copolymer in which polyethylene glycol and polypropylene glycol are polymerized in the order of polyethylene glycol, polypropylene glycol, and polyethylene glycol, and the cyclic molecules are β-cyclodextrin, and the bulky substituents are N-trityl glycine.

The intracellularly degradable linkages in the linear molecule of the polyrotaxane represented by Structural Formulae (1), (5), and (6) are disulfide linkages, the intracellularly degradable linkages in the linear molecule of the polyrotaxane represented by Structural Formula (2) are acetal linkages, and the intracellularly degradable linkages in the linear molecule of the polyrotaxane represented by Structural Formula (4) are ester linkages.

In Structural Formulae (1), (2), (4), (5), and (6), "m" denotes the number of repetitive units (hereinafter, sometimes referred to as "monomers") of polypropylene glycol (in Structural Formulae (1), (2), (4), (5), and (6), since three repetitive units of propylene glycol are depicted, it is described as "m/3"), and "n" denotes the number of repetitive units (monomers) of polyethylene glycol. Moreover, β-CD in Structural Formulae (1), (2), and (4) is represented by following Formula (A), and only one β-CD is depicted in Structural Formulae (1), (2), and (4). Furthermore, β-CD in Structural Formula (5) is represented by following Formula (B), and only one β-CD is depicted in Structural Formula (5). β-CD in Structural Formula (6) is represented by following Formula (C), and only one β-CD is depicted in Structural Formula (6).

Moreover, in following Formula (A), a primary hydroxyl group of β-cyclodextrin is modified with a hydroxy ethyl group via carbamic ester (—O—CO—NH—), in following Formula (B), a primary hydroxyl group of β-cyclodextrin is modified with N,N-dimethyl amino ethyl group via carbamic ester (—O—CO—NH—), and in following Formula (C), a primary hydroxyl group of β-cyclodextrin is modified with a hydroxy ethoxy ethyl group via carbamic ester (—O—CO—NH—). In following Formulae (A), (B), and (C), cases where the number of modifications is x (x=1 to 7) are shown.

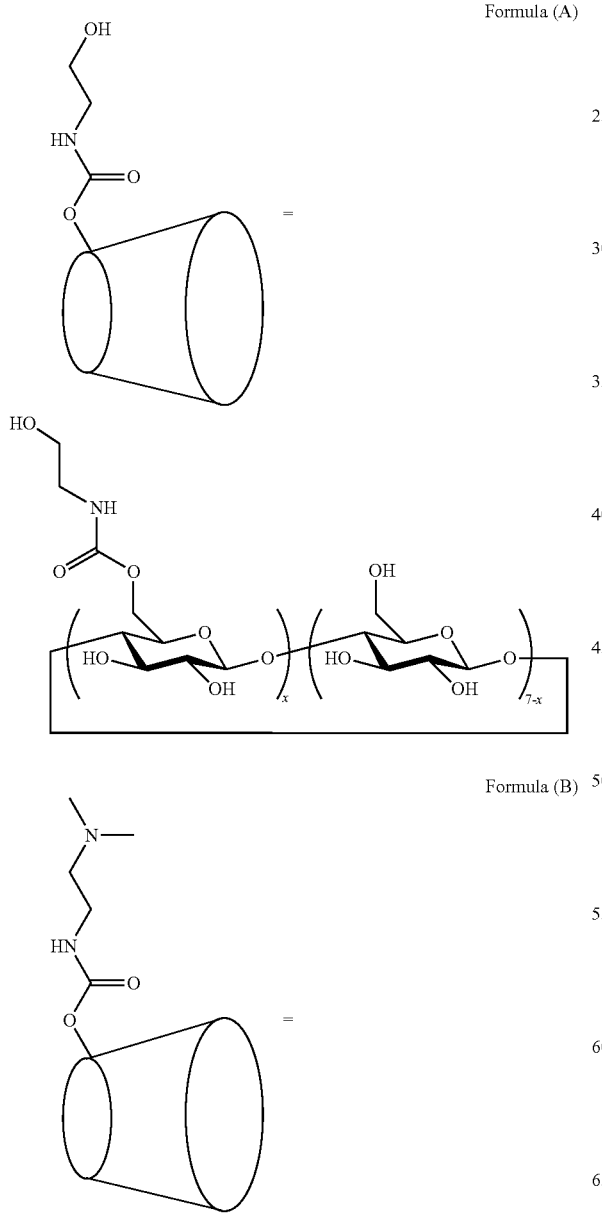

Formula (A)

Formula (B)

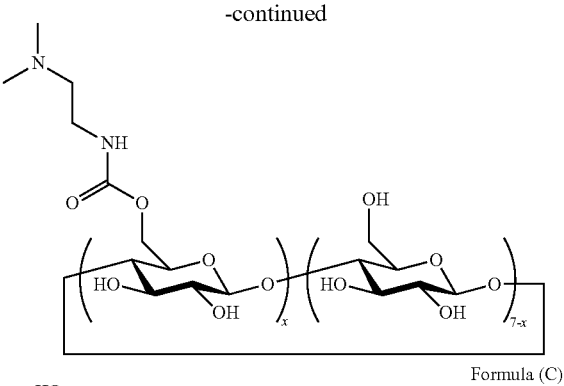

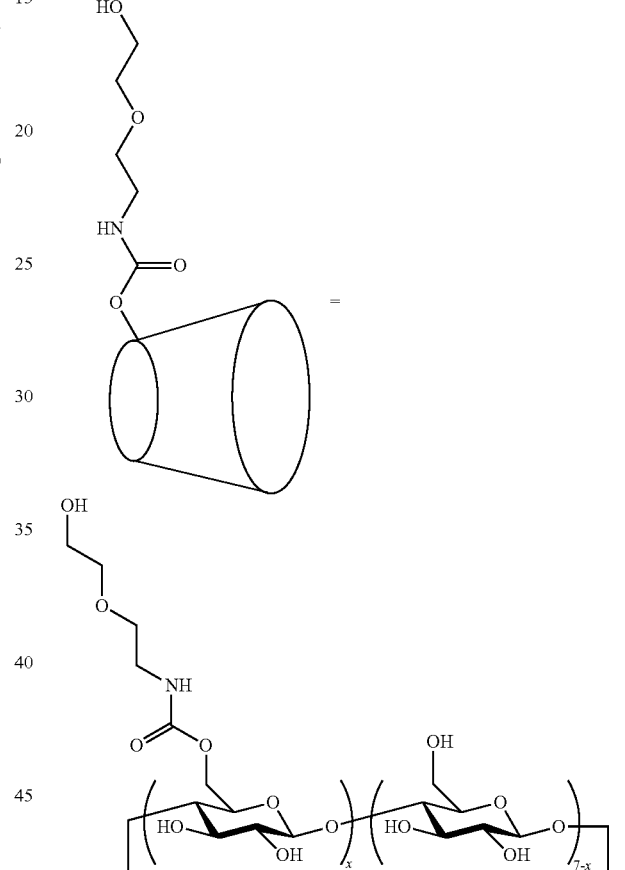

Formula (C)

The number average molecular weight of a linear molecule in the polyrotaxane represented by each of Structural Formulae (1), (2), (4), (5), and (6) is 1,100 for the polyethylene glycol moiety and 4,200 for the polypropylene glycol moiety.

The number of threaded cyclic molecules in the polyrotaxane represented by Structural Formula (1) is on average 12.9 per molecule of polyrotaxane.

The number of threaded cyclic molecules in the polyrotaxane represented by Structural Formula (2) is on average 12.9 per molecule of polyrotaxane.

The number of threaded cyclic molecules in the polyrotaxane represented by Structural Formula (4) is on average 11.7 per molecule of polyrotaxane.

The number of threaded cyclic molecules in the polyrotaxane represented by Structural Formula (5) is on average 12.9 per molecule of polyrotaxane.

The number of threaded cyclic molecules in the polyrotaxane represented by Structural Formula (6) is on average 16.1 per molecule of polyrotaxane.

The number of modifications with hydroxyethyl group in the polyrotaxane represented by Structural Formula (1) is on average 53.4 modifications per molecule of polyrotaxane.

The number of modifications with hydroxyethyl group in the polyrotaxane represented by Structural Formula (2) is on average 66.9 modifications per molecule of polyrotaxane.

The number of modifications with hydroxyethyl group in the polyrotaxane represented by Structural Formula (4) is on average 65.9 modifications per molecule of polyrotaxane.

The number of modifications with N, N-dimethyl amino ethyl group in the polyrotaxane represented by Structural Formula (5) is on average 65.3 modifications per molecule of polyrotaxane.

The number of modifications with hydroxyl ethoxy ethyl group in the polyrotaxane represented by Structural Formula (6) is on average 64.7 modifications per molecule of polyrotaxane.

The polyrotaxane represented by Structural Formula (1) can be prepared suitably by the method of Preparation Example 1 described later. The polyrotaxane represented by Structural Formula (2) can be prepared suitably by the method of Preparation Example 2 described later. The polyrotaxane represented by Structural Formula (4) can be prepared suitably by the method of Preparation Example 3 described later. The polyrotaxane represented by Structural Formula (5) can be prepared suitably by the method of Preparation Example 4 described later. The polyrotaxane represented by Structural Formula (6) can be prepared suitably by the method of Preparation Example 5 described later.

As to whether or not the polyrotaxane prepared has a structure represented by Structural Formula (1), (2), (4), (5), or (6) can be verified by various methods of analysis appropriately selected, and proton nuclear magnetic resonance is one of such methods.

Figure 2:
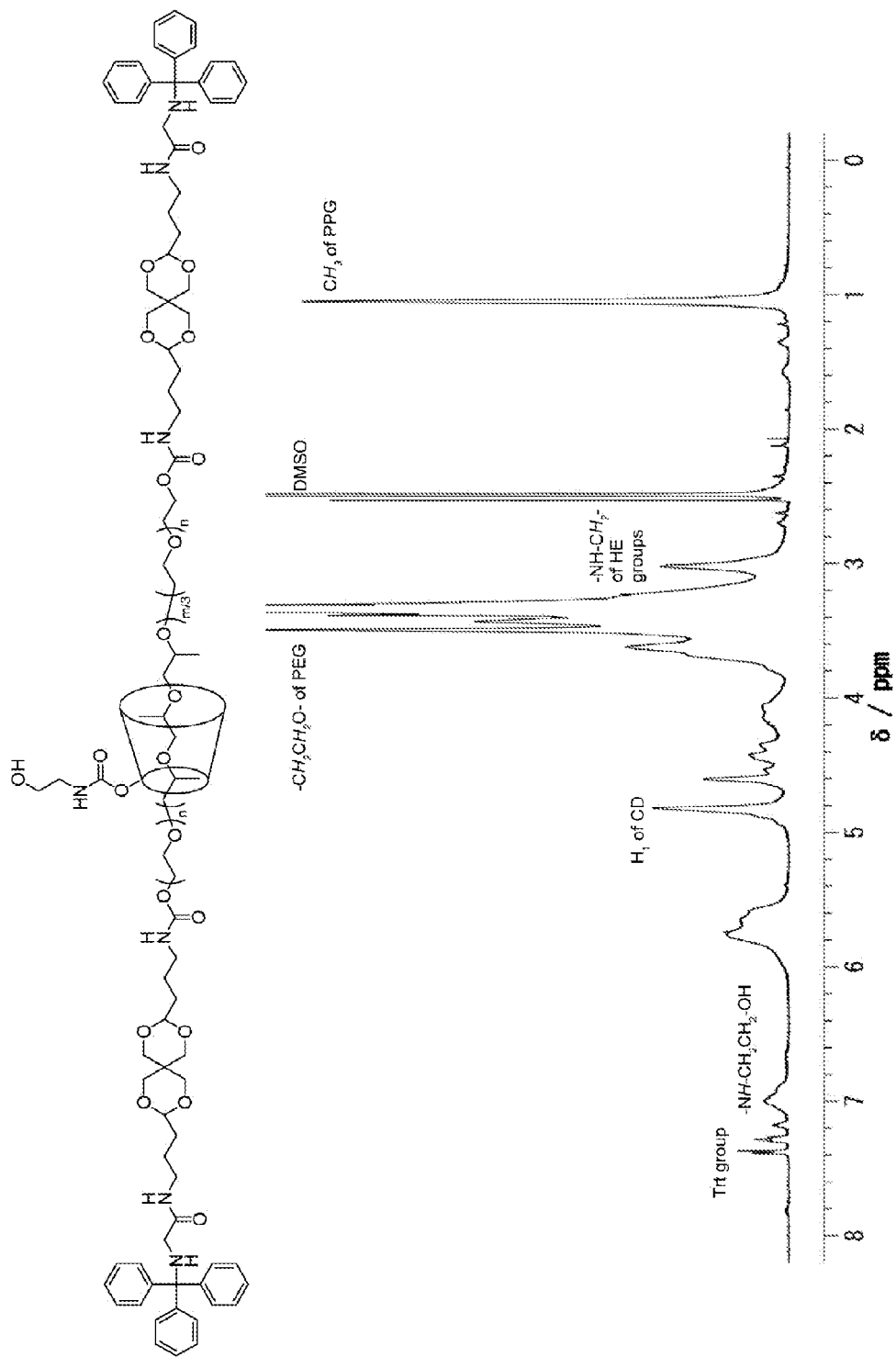
FIG. 2 is a proton nuclear magnetic resonance spectrum at 500 MHz, measured in deuterated dimethyl sulfoxide, of a polyrotaxane obtained in Preparation Example 2. Horizontal axis: unit in ppm.
Figure 4:
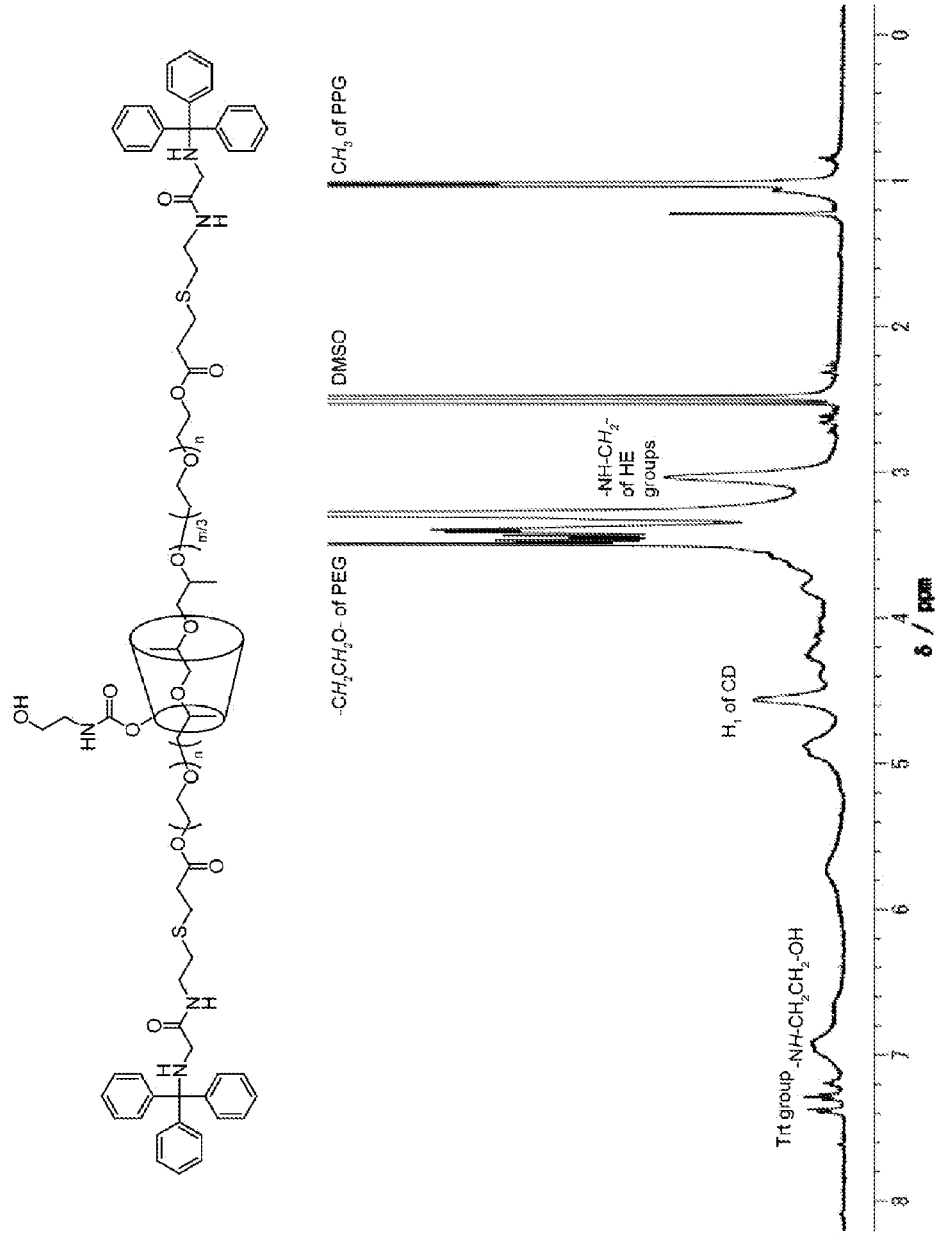
FIG. 4 is a proton nuclear magnetic resonance spectrum at 500 MHz, measured in deuterated dimethyl sulfoxide, of a polyrotaxane obtained in Preparation Example 3. Horizontal axis: unit in ppm.
Figure 5:
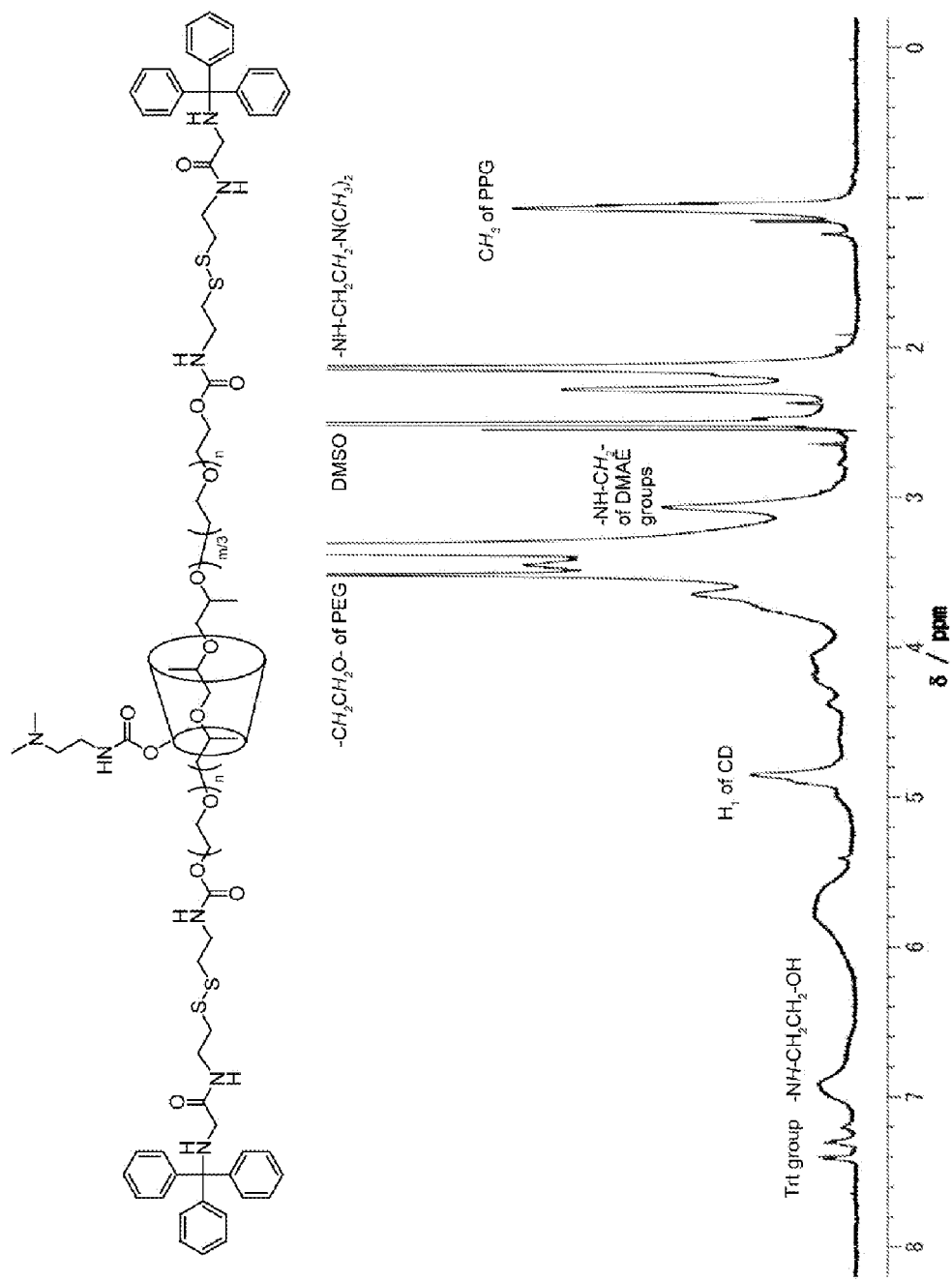
FIG. 5 is a proton nuclear magnetic resonance spectrum at 500 MHz, measured in deuterated dimethyl sulfoxide, of a polyrotaxane obtained in Preparation Example 4. Horizontal axis: unit in ppm.
Figure 6:
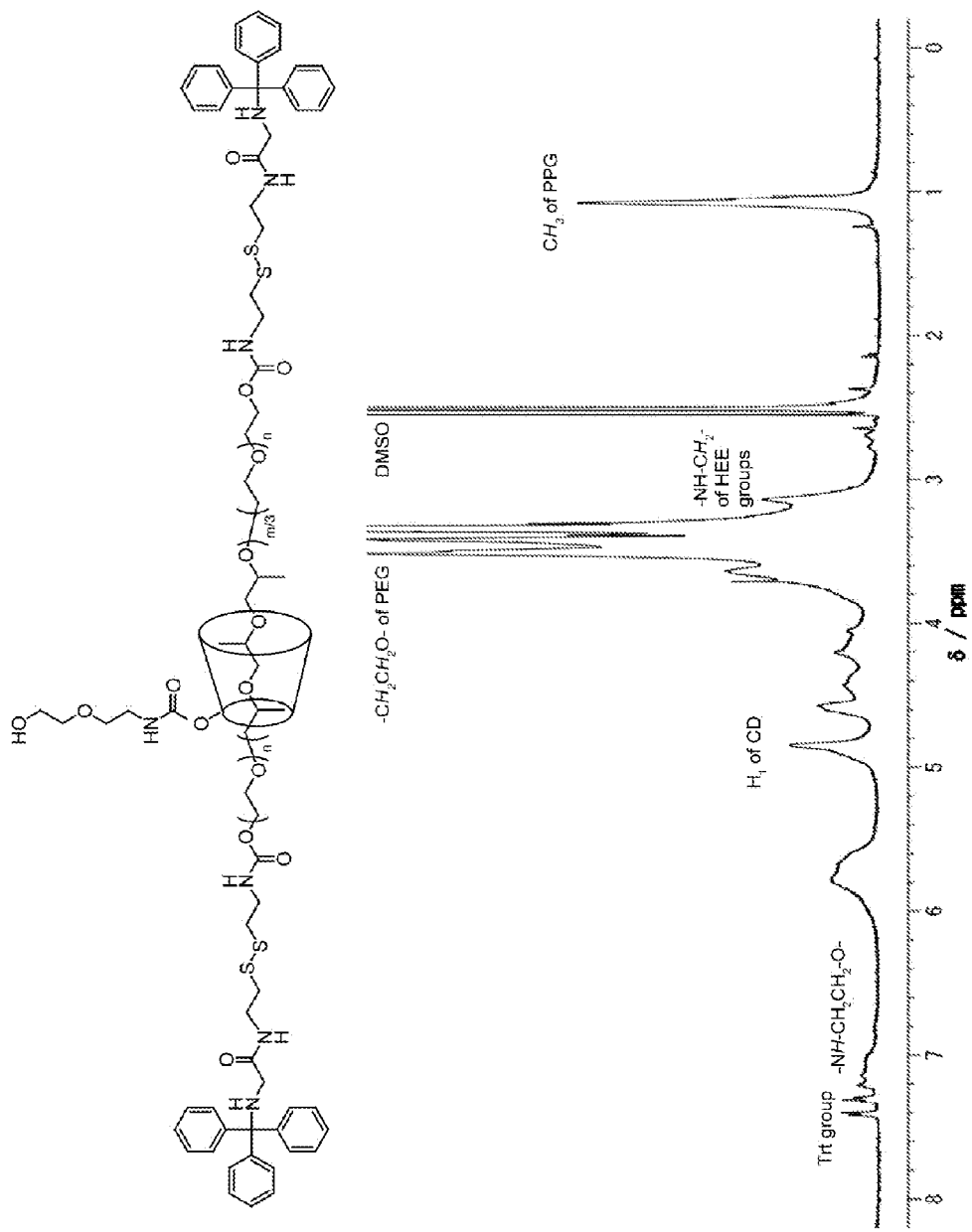
FIG. 6 is a proton nuclear magnetic resonance spectrum at 500 MHz, measured in deuterated dimethyl sulfoxide, of a polyrotaxane obtained in Preparation Example 5. Horizontal axis: unit in ppm.

A proton nuclear magnetic resonance spectrum at 500 MHz, measured in deuterated dimethyl sulfoxide, of the polyrotaxane represented by Structural Formula (1) is as shown in FIG. 1. A proton nuclear magnetic resonance spectrum at 500 MHz, measured in deuterated dimethyl sulfoxide, of the polyrotaxane represented by Structural Formula (2) is as shown in FIG. 2. A proton nuclear magnetic resonance spectrum at 500 MHz, measured in deuterated dimethyl sulfoxide, of the polyrotaxane represented by Structural Formula (4) is as shown in FIG. 4. A proton nuclear magnetic resonance spectrum at 500 MHz, measured in deuterated dimethyl sulfoxide, of the polyrotaxane represented by Structural Formula (5) is as shown in FIG. 5. A proton nuclear magnetic resonance spectrum at 500 MHz, measured in deuterated dimethyl sulfoxide, of the polyrotaxane represented by Structural Formula (6) is as shown in FIG. 6.

There may be some error in values measured by the analytical methods. However, a person skilled in the art can easily identify that the polyrotaxane has a structure represented by Structural Formula (1), (2), (4), (5), or (6).

The amount of polyrotaxane in the pharmaceutical composition of the present invention is not particularly limited, and can be appropriately selected according the object. The pharmaceutical composition may be the polyrotaxane itself.

<Diseases Caused Due to at Least One of Lipid Metabolism Disorders and Autophagy Dysfunctions>

A disease caused by at least one of lipid metabolism disorders and autophagy dysfunctions may be a disease caused only due to a lipid metabolism disorder, or may be a disease caused only due to an autophagy dysfunction, or may be a disease caused due to both of a lipid metabolism disorder and an autophagy dysfunction.

<<Diseases Caused Due to Lipid Metabolism Disorder>>

Diseases caused due to lipid metabolism disorder include lysosomal diseases. The lysosomal disease is also a disease caused due to autophagy dysfunction which presents an accumulation of autophagosomes.

—Lysosomal Diseases—

Concrete examples of lysosomal diseases include Gaucher's disease, Niemann-Pick Type A disease, Niemann-Pick Type B disease, Niemann-Pick Type C disease, GM1 gangliosidosis, GM2 gangliosidosis (sometimes also referred to as "Tay-Sachs Sandhoff AB variant"), Krabbe disease, metachromatic leukodystrophy, multiple sulfatase deficiency, Farber disease, Mucopolysaccharidosis I, Mucopolysaccharidosis II (sometimes also referred to as "Hunter disease"), Mucopolysaccharidosis III (sometimes also referred to as "Sanfilippo disease"), Mucopolysaccharidosis IV, Mucopolysaccharidosis VI (sometimes also referred to as 'Maroteaux-Lamy disease), Mucopolysaccharidosis VII (sometimes also referred to as "Sly disease"), Mucopolysaccharidosis IX (sometimes also referred to as "Hyaluronidase deficiency"), Sialidosis, Galactosialidosis, I-cell disease/Mucolipidosis type III, α-mannosidosis, β-mannosidosis, Fucosidosis, Aspartyglucosaminuria, Schindler/Kanzaki disease, Wolman disease, Dannon disease, free sialic acid storage disease, ceroid lipofuscinosis, and Fabry disease.

Disorders caused due to autophagy dysfunction include Alzheimer's disease, Parkinson's disease, and Huntington's disease. These are disorders in which autophagosomes are accumulated.

The pharmaceutical composition of the present invention can be used favorably for the treatment of lysosomal diseases which include Gaucher's disease, Niemann-Pick Type A disease, Niemann-Pick Type B disease, Niemann-Pick Type C disease, GM1 gangliosidosis, GM2 gangliosidosis, Farber disease, Wolman disease, and Fabry disease, and can be used more favorably for the treatment of Niemann-Pick Type C disease.

<Other Ingredients>

The other ingredients are not particularly limited, and can be appropriately selected according to the object. The other ingredients include pharmaceutically acceptable carriers. The carriers are also not particularly limited, and can be appropriately selected according to the dosage form.

The amount of the other ingredients in the pharmaceutical composition of the present invention is not particularly limited, and can be appropriately selected according to the object.

<Dosage Form>

The dosage form of the pharmaceutical composition of the present invention is not particularly limited, and can be appropriately selected according to the desired method of administration described later. The examples includes injectables (solutions, suspensions, and solid formulations to be dissolved before use), inhalation powders, and the like.

As the injectables, injectables for subcutaneous use, intramuscular use, and intravenous use can be prepared conventionally by adding agents such as a pH adjusting agent, a buffering agent, a stabilizing agent, a tonicity agent, and a local anesthetic agent to the polyrotaxane.

Examples of the pH adjusting agent and the buffering agent are sodium citrate, sodium acetate, sodium phosphate, and the like. Examples of the stabilizing agent are sodium pyrosulfite, EDTA, thioglycolic acid, thiolactic acid, and the like. Examples of the tonicity agent are sodium chloride, glucose sugar, and the like. Examples of the local anesthetic agent are procaine hydrochloride, lidocaine hydrochloride, and the like.

<Administration>

The method for administration of the pharmaceutical composition of the present invention is not particularly limited, and can be selected from a local administration and a systemic administration depending on the dosage form of the pharmaceutical composition and condition of a patient. Examples of the local administration include intracerebroventricular administration, and the like.

The subject to administer the pharmaceutical composition of the present invention is not particularly limited, and can be appropriately selected, according to the object, from among human beings, mice, rats, cows, pigs, monkeys, dogs, cats, and the like.

The amount of administration of the pharmaceutical composition of the present invention is not particularly limited, and can be appropriately selected according to the dosage form, age of the subject, weight of the subject, desired degree of effect, and the like.

The timing of administration of the pharmaceutical composition of the present invention is not particularly limited, and can be appropriately selected according to the object. The pharmaceutical composition may be administered prophylactically to prevent the disease or may be administered therapeutically to treat the disease.

The number of dosages of the pharmaceutical composition of the present invention is not particularly limited, and can be appropriately selected according to the age of the subject, weight of the subject, desired degree of effect, and the like.

The polyrotaxane included in the pharmaceutical composition of the present invention is supposed that hemolysis and nonspecific inclusion of hydrophobic biomolecules does not occur, and is considered to be highly safe, since the cavities of the cyclic molecules are occupied by the linear molecule until degraded intracellularly.

Moreover, when the polyrotaxane reaches inside the cells, the intracellularly degradable linkages at ends are cleaved, and a large number of cyclic molecules are released gradually, thereby, the polyrotaxane acting as a cholesterol removing agent. Therefore, a cholesterol removing effect and its prolonged durability are expected.

Furthermore, since a polyrotaxane framework has a high molecular weight with the number average molecular weight of about 20,000 to 100,000, it is less susceptible to renal excretion after intravenous injection, and the blood half-life is considered to be longer than that of cyclo-dextrin alone. Therefore, it is believed to lead to reduction in the dose and dosage frequency.

Moreover, the polyrotaxane included in the pharmaceutical composition of the present invention has a low cytotoxicity, and also is capable of removing cholesterol at low concentration.

Furthermore, the polyrotaxane included in the pharmaceutical composition of the present invention has a superior effect of enhancing formation of autolysosomes.

The polyrotaxane included in the pharmaceutical composition of the present invention, and the polyrotaxane of the present invention can be used also as an intracellular cholesterol removing agent, or as an autolysosome formation enhancing agent.

(Method of Prophylaxis or Treatment)

The pharmaceutical composition, by administering to an individual, removes cholesterol in the cells and enhances formation of autolysosomes, and is capable of preventing or treating a disorder caused due to at least one of lipid metabolism disorders and autophagy dysfunctions. Consequently, the present invention also relates to a method for either preventing or treating a disorder caused due to at least one of the liquid metabolism disorders and autophagy dysfunctions by administering the pharmaceutical composition of the present invention to an individual.

EXAMPLES

Specific preparation examples and test examples of the present invention are illustrated below, but the present invention should not be construed as being limited by these preparation examples and test examples.

Preparation Example 1: Preparation of Polyrotaxane-1

Pluronic P123 (Sigma-Aldrich; a copolymer composed of polyethylene glycol (hereinafter sometimes referred to as "PEG") and polypropylene glycol (hereinafter sometimes referred to as "PPG") in the order of PEG-PPG-PEG; the number-average molecular weight of the PPG moiety is 4,200, and the number average molecular weight of the PEG moieties is 1,100×2) was used as a liner molecule, and was linked to a cystamine group at each of both ends.

20 g of above-mentioned Pluronic P123 and 10.2 g of 1,1'-carbonyldiimidazole (Sigma-Aldrich) were measured and transferred to an eggplant-shaped flask. 267 mL of tetrahydrofuran (Kanto Chemical) was added and dissolved, and the mixture was stirred for 24 hours at room temperature. After the reaction, the mixture was transferred to a dialysis membrane of molecular weight cut-off of 1,000 (Spectra) to dialysis against tetrahydrofuran, so as to remove unreacted material. By concentrating on a rotary evaporator, 20 g of Pluronic P123 having a carbonylimidazole at each of both ends (hereinafter, sometimes referred to as "P123-CI") was obtained.

9 g of P123-CI was measured and dissolved in 8 mL of N,N-dimethylformamide. 2 g of desalted cystamine (Wako Pure Chemical Industries) was measured and added to an eggplant-shaped flask, and dissolved in 72 mL of N,N-dimethyl formamide. The P123-CI solution was added dropwise to an eggplant-shaped flask, and stirred at room temperature for 24 hours. After the reaction, the mixture was transferred to a dialysis membrane of molecular weight cut-off of 1,000 to dialysis against methanol (Kanto Chemical), so as to remove unreacted material. By concentrating on a rotary evaporator, 4.95 g of Pluronic P123 having a cystamine group at each of both ends (hereinafter, sometimes referred to as "P123-SS—$NH_2$") was obtained.

P123-SS—$NH_2$ and β-cyclodextrin (hereinafter, sometimes referred to as "β-CD") were used to prepare pseudopolyrotaxane as follows.

12 g of β-CD was measured and added to a jar, and dissolved in 600 mL of phosphate buffer solution. 1 g of above-mentioned P123-SS—$NH_2$ was measured and dissolved in a small amount of ultra-pure water. The P123-SS—$NH_2$ solution was added to the β-CD solution and stirred at room temperature for 24 hours. After the reaction, the resulting precipitate was collected by centrifugation. A pseudopolyrotaxane was obtained by freeze-drying the collected solid.

A polyrotaxane comprising a plurality of β-CD molecules threaded by a linear molecule, where the linear molecule is linked to bulky substituents via intracellularly degradable disulfide bonds at both ends (hereinafter, sometimes referred to as "PRX"), was obtained by capping the both ends of the pseudo-polyrotaxane with N-trityl-glycine (Sigma-Aldrich) as follows.

1.64 g of N-tritylglycine and 1.64 g of 4-(4,6-dimethoxy-1,3,5-triazin-2-yl)-4-methylmorpholinium chloride hydrate (Wako Pure Chemical Industries) were measured and added to a screw tube, and dissolved in a mixed solvent of 11.2 mL of N,N-dimethylformamide and 44.8 mL of methanol. This solution was added to the obtained pseudo-polyrotaxane, and the mixture was stirred at room temperature for 24 hours. After the reaction, the resulting precipitate was collected by centrifugation. The obtained precipitate was washed with methanol, N,N-dimethylformamide, and ultrapure water in this order to remove unreacted substances. By freeze-drying the recovered solid, 697.2 mg of polyrotaxane having a disulfide bond at each end was obtained.

Water-soluble Polyrotaxane-1 (hereinafter, sometimes referred to as "HE-SS-PRX") was obtained by introducing hydroxyethyl (HE) groups into the β-CDs of the polyrotaxane as follows (the average number of threaded β-CDs per polyrotaxane molecule is 12.9; the average number of HE substitutions is 53.4).

250 mg of the polyrotaxane having disulfide bonds at the ends was measured and dissolved in 10 mL of dimethylsulfoxide. 235 mg of 1,1'-carbonyldiimidazole was added, and the mixture was stirred at room temperature for 24 hours. Then, 439 μL of 2-amino-ethanol was added to the reaction solution, and the mixture was stirred for another 24 hours at room temperature. After the reaction, the mixture was transferred to a dialysis membrane of molecular weight cut-off of 3,500 (Spectra) to dialysis against ultrapure water, so as to remove unreacted material. By freeze-drying the recovered solution, 231.5 mg of polyrotaxane having a disulfide bond at each of the ends and having been introduced with hydroxyethyl groups (HE-SS-PRX) was obtained.

FIG. 1 shows a proton nuclear magnetic resonance spectrum at 500 MHz for HE-SS-PRX in heavy dimethylsulfoxide (Sigma-Aldrich).

The proton nuclear magnetic resonance spectrum confirmed that HE-SS-PRX had a structure represented by following Structural Formula (1). In below Structural Formula (1), "m" represents the number of polypropylene glycol repeating units (in Formula (1), "m/3" is denoted since three polypropylene glycol repeating units are shown in parentheses) and "n" represents the number of polyethylene glycol repeating units. In addition, in Structural Formula (1) below, only one β-CD, which is represented by following Formula (A), is shown. Further, in Formula (A) below, the case where the number of the modifying hydroxyethyl groups is x (x=1 to 7) is shown.

Structural Formula (1)

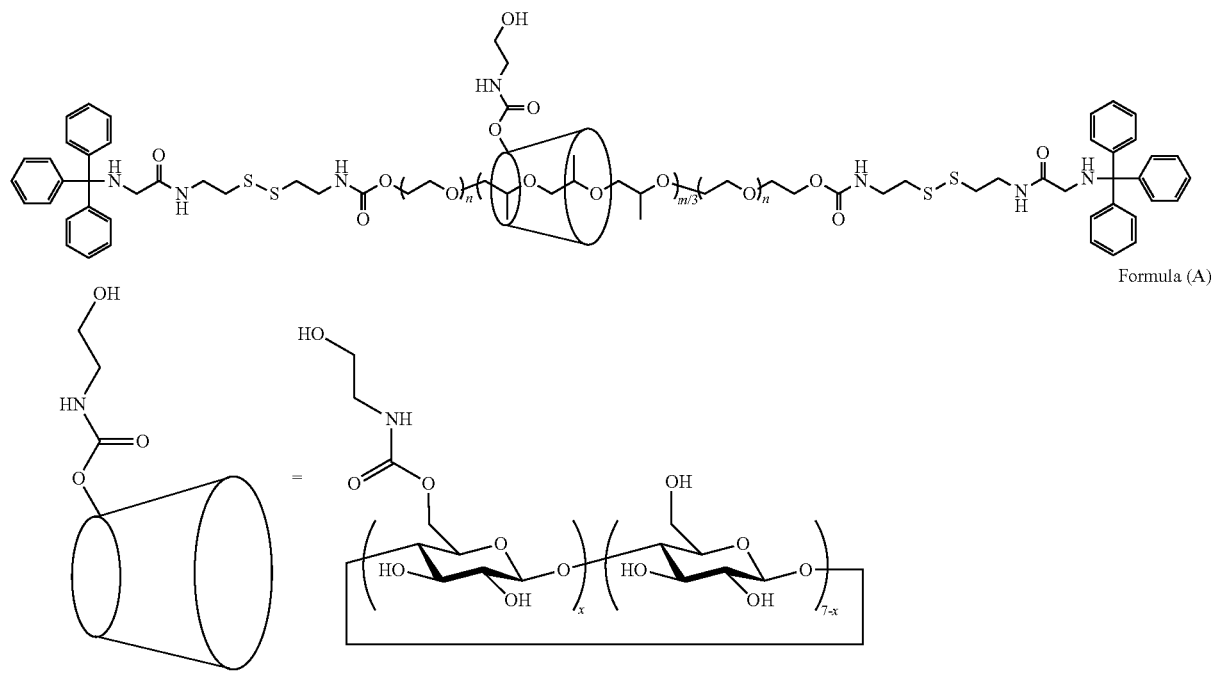

Formula (A)

Preparation Example 2: Preparation of Polyrotaxane-2

Above-mentioned Pluronic P123 was used as a linear molecule, and was provided with acetal bonds at both ends as follows.

8.14 g of P123-CI that was synthesized in the same manner as in Preparation Example 1 was measured and dissolved in 10 mL of N,N-dimethylformamide. 6.81 g of 3,9-bis(3-amino-propyl)-2,4,8,10-tetraoxaspiro[5.5]undecane was added to an eggplant-shaped flask, and dissolved in 100 mL of N,N-dimethylformamide. The P123-CI solution was added dropwise to the eggplant-shaped flask, and stirred at room temperature for 24 hours. After the reaction, the mixture was transferred to a dialysis membrane of molecular weight cut-off of 1,000 to dialysis against methanol, so as to remove unreacted material. By concentrating on a rotary evaporator, 7.0 g of Pluronic P123 having a cyclic acetal bond at each of both ends (hereinafter, sometimes referred to as "P123-ace-NH$_2$") was obtained.

A pseudo-polyrotaxane was prepared in the same manner as in Preparation Example 1, except that P123-ace-NH$_2$ was used.

A polyrotaxane comprising a plurality of β-CD molecules threaded by a linear molecule, where the linear molecule is linked to bulky substituents via intracellularly degradable acetal bonds at both ends, was obtained by capping the both ends of the pseudo-polyrotaxane with N-trityl-glycine in the same manner as in Preparation Example 1.

Water-soluble Polyrotaxane-2 (hereinafter, sometimes referred to as "HE-ace-PRX") was obtained by introducing HE groups into the β-CDs of the polyrotaxane in the same manner as in Preparation Example 1 (the average number of threaded β-CDs per polyrotaxane molecule is 12.9; the average number of HE substitutions is 66.9).

FIG. 2 shows a proton nuclear magnetic resonance spectrum at 500 MHz for HE-ace-PRX in heavy dimethylsulfoxide (Sigma-Aldrich).

The proton nuclear magnetic resonance spectrum confirmed that HE-ace-PRX had a structure represented by the following Structural Formula (2). In below Structural Formula (2), "m" represents the number of polypropylene glycol repeating units (in Formula (2), "m/3" is denoted since three polypropylene glycol repeating units are shown in parentheses) and "n" represents the number of polyethylene glycol repeating units. In addition, in Structural Formula (2) below, only one β-CD, which is represented by above Formula (A), is shown. Further, in above Formula (A), the case where the number of the modifying hydroxyethyl groups is x (x=1 to 7) is shown.

(Wako Pure Chemical Industries) was measured and added to an eggplant-shaped flask, and dissolved in 80 mL of N,N-dimethyl formamide. The P123-CI solution was added dropwise to the eggplant-shaped flask, and stirred at room temperature for 24 hours. After the reaction, the mixture was transferred to a dialysis membrane of molecular weight cut-off of 1,000 to dialysis against methanol, so as to remove unreacted material. By concentrating on a rotary evaporator, 5.85 g of Pluronic P123 having a primary amino group at each of both ends (hereinafter, sometimes referred to as "P123-NH$_2$") was obtained.

A pseudo-polyrotaxane was prepared in the same manner as in Preparation Example 1, except that P123-NH$_2$ was used.

A polyrotaxane comprising a plurality of β-CD molecules threaded by a linear molecule, where the linear molecule is linked to bulky substituents at both ends without intracellularly degradable linkage, was obtained by capping the both ends of the pseudo-polyrotaxane with N-trityl-glycine in the same manner as in Preparation Example 1.

Water-soluble Polyrotaxane-3 (hereinafter, sometimes referred to as "HE-PRX") was obtained by introducing HE groups into the β-CDs of the polyrotaxane in the same manner as in Preparation Example 1 (the average number of threaded β-CDs per polyrotaxane molecule is 11.3; the average number of HE substitutions is 65.3).

Figure 3:
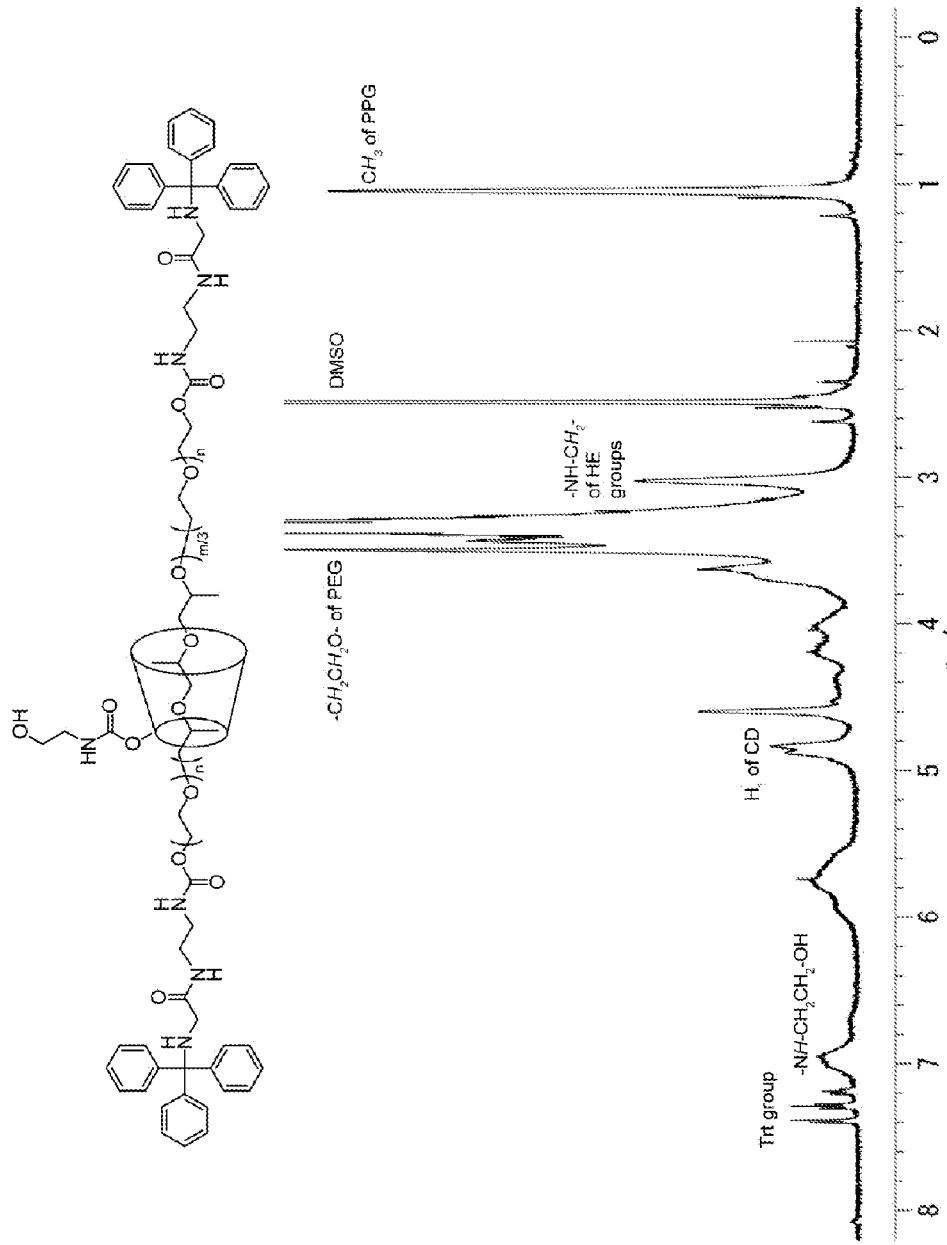
FIG. 3 is a proton nuclear magnetic resonance spectrum at 500 MHz, measured in deuterated dimethyl sulfoxide, of a polyrotaxane obtained in Comparative Preparation Example 1. Horizontal axis: unit in ppm.

FIG. 3 shows a proton nuclear magnetic resonance spectrum at 500 MHz for HE-PRX in heavy dimethylsulfoxide (Sigma-Aldrich).

The proton nuclear magnetic resonance spectrum confirmed that HE-ace-PRX had a structure represented by the following Structural Formula (3). In below Structural Formula (3), "m" represents the number of polypropylene Structural Formula (2)

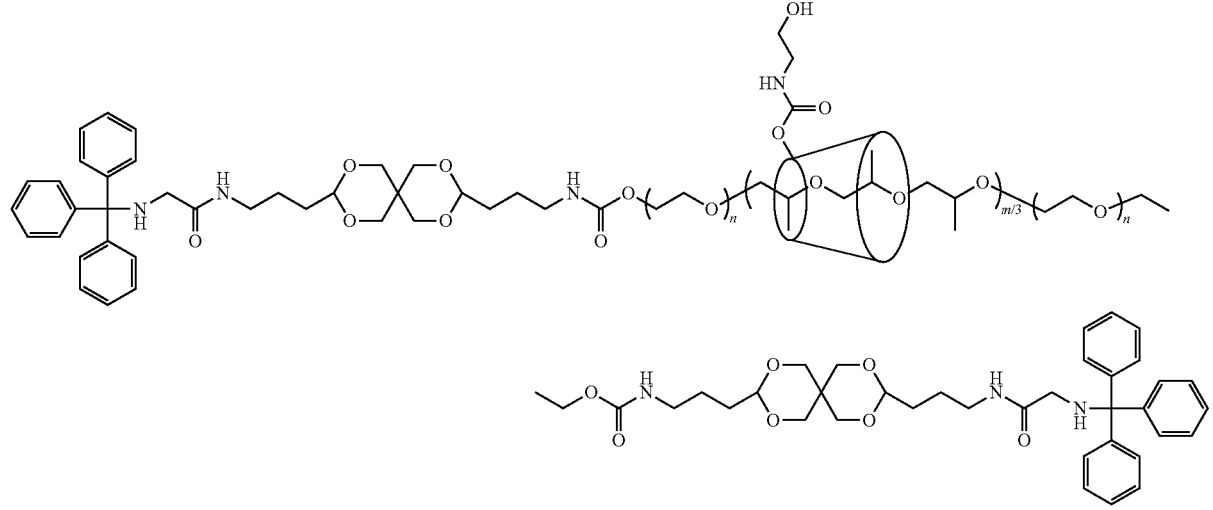

Comparative Preparation Example 1: Preparation of Polyrotaxane-3

Above-mentioned Pluronic P123 was used as a linear molecule to prepare a linear molecule that does not have an intracellularly degradable linkage, as follows.

9 g of P123-CI that was synthesized in the same manner as in Preparation Example 1 was measured, and dissolved in 8 mL of N,N-dimethylformamide. 1.65 g of ethylenediamine glycol repeating units (in Formula (3), "m/3" is denoted since three polypropylene glycol repeating units are shown in parentheses) and "n" represents the number of polyethylene glycol repeating units. In addition, in Structural Formula (3) below, only one β-CD, which is represented by above Formula (A), is shown. Further, in above Formula (A), the case where the number of the modifying hydroxyethyl groups is x (x=1 to 7) is shown.

Structural Formula (3)

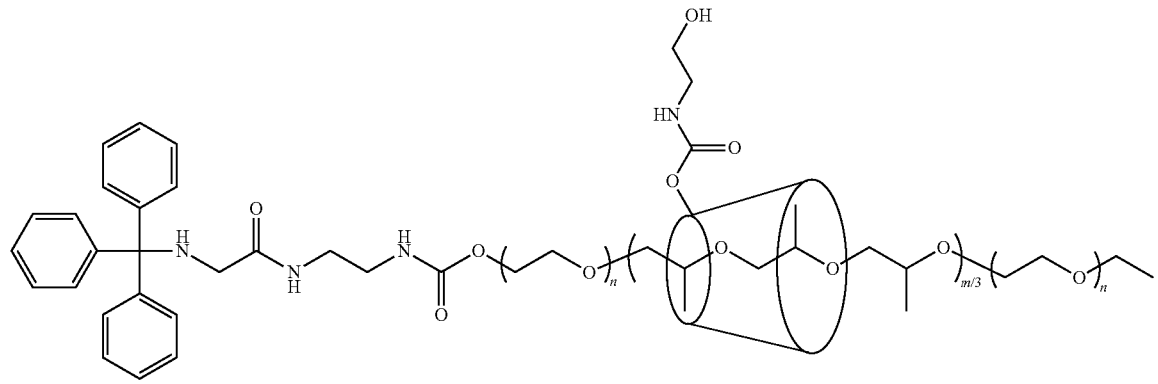

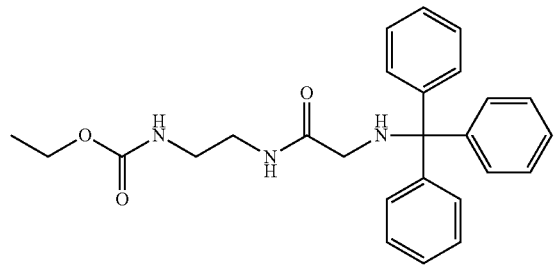

Preparation Example 3: Preparation of Polyrotaxane-4

Above-mentioned Pluronic P123 was used as a linear molecule, and provided with ester bonds at both ends as follows.

10 g of above-mentioned Pluronic P123 was measured and added to an eggplant-shaped flask, and dissolved in 133 mL of tetrahydrofuran. 3.3 mL of triethylamine (Wako Pure Chemical Industries) was added to the solution. Then, 1.28 mL of acryloyl chloride (Wako Pure Chemical Industries) was added under ice cooling and stirred for 24 hours at room temperature. After the reaction, the mixture was transferred to a dialysis membrane of molecular weight cut-off of 1,000 to dialysis against methanol, so as to remove unreacted material. By concentrating on a rotary evaporator, 6.12 g of Pluronic P123 having acryloyl groups at both ends was obtained.

5.0 g of Pluronic P123 having acryloyl groups at both ends and 1.2 g of cysteamine hydrochloride were measured and added to an eggplant type flask, and dissolved in 40 mL of N,N-dimethylformamide and stirred at room temperature for 24 hours. After the reaction, the mixture was transferred to a dialysis membrane of molecular weight cut-off of 1,000 to dialysis against methanol, so as to remove unreacted material. By concentrating on a rotary evaporator, 2.54 g of Pluronic P123 having a primary amino group via an ester linkage at each of both ends (hereinafter, sometimes referred to as "P123-COO—$NH_2$") was obtained.

A pseudo-polyrotaxane was prepared in the same manner as in Preparation Example 1, except that P123-COO—$NH_2$ was used.

A polyrotaxane comprising a plurality of β-CD molecules threaded by a linear molecule, where the linear molecule is linked to bulky substituents via intracellularly degradable ester linkages at both ends, was obtained by capping the both ends of the pseudo-polyrotaxane with N-trityl-glycine in the same manner as in Preparation Example 1.

Water-soluble Polyrotaxane-2 (hereinafter, sometimes referred to as "HE-COO-PRX") was obtained by introducing HE groups into the β-CDs of the polyrotaxane in the same manner as in Preparation Example 1 (the average number of threaded β-CDs per polyrotaxane molecule is 11.7; the average number of HE substitutions is 65.9).

FIG. 4 shows a proton nuclear magnetic resonance spectrum at 500 MHz for HE-COO-PRX in heavy dimethylsulfoxide (Sigma-Aldrich).

The proton nuclear magnetic resonance spectrum confirmed that HE-COO-PRX had a structure represented by the following Structural Formula (4). In below Structural Formula (4), "m" represents the number of polypropylene glycol repeating units (in Formula (4), "m/3" is denoted since three polypropylene glycol repeating units are shown in parentheses) and "n" represents the number of polyethylene glycol repeating units. In addition, in Structural Formula (4) below, only one β-CD, which is represented by above Formula (A), is shown. Further, in above Formula (A), the case where the number of the modifying hydroxyethyl groups is x (x=1 to 7) is shown.

Structural Formula (4)

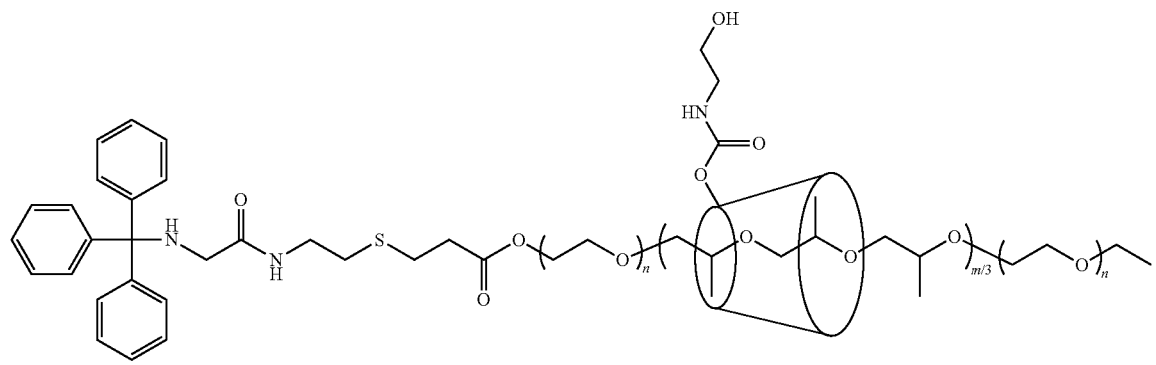
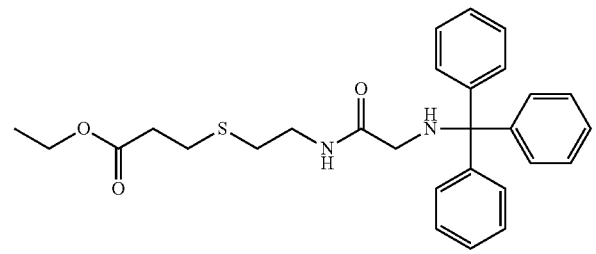

Preparation Example 4: Preparation of Polyrotaxane-5

Water-soluble Polyrotaxane-5 (hereinafter, sometimes referred to as "DMAE-SS-PRX") was obtained by introducing N,N-dimethylaminoethyl (DMAE) groups into the β-CDs of the polyrotaxane having disulfide linkages at the ends which was prepared in the same manner as in Preparation Example 1 (the average number of threaded β-CDs per polyrotaxane molecule is 12.9; the average number of DMAE groups is 65.3).

125 mg of the polyrotaxane having disulfide linkages at the ends was measured and dissolved in 5 mL of dimethylsulfoxide. 117 mg of 1,1'-carbonyldiimidazole was added, and the mixture was stirred at room temperature for 24 hours. Then, 237 μL of N,N-dimethylaminoethylamine (Wako Pure Chemical Industries) was added to the reaction solution, and the mixture was stirred for another 24 hours at room temperature. After the reaction, the mixture was transferred to a dialysis membrane of molecular weight cut-off of 3,500 (Spectra) to dialysis against ultrapure water, so as to remove unreacted material. By freeze-drying the recovered solution, 104.7 mg of polyrotaxane having a disulfide linkage at each of the ends and having been introduced with N,N-dimethylaminoethylamine groups (DMAE-SS-PRX) was obtained.

FIG. 5 shows a proton nuclear magnetic resonance spectrum at 500 MHz for DMAE-SS-PRX in heavy dimethylsulfoxide (Sigma-Aldrich).

The proton nuclear magnetic resonance spectrum confirmed that DMAE-SS-PRX had a structure represented by the following Structural Formula (5). In below Structural Formula (5), "m" represents the number of polypropylene glycol repeating units (in Formula (5), "m/3" is denoted since three polypropylene glycol repeating units are shown in parentheses) and "n" represents the number of polyethylene glycol repeating units. In addition, in Structural Formula (5) below, only one β-CD, which is represented by following Formula (B), is shown. Further, in Formula (B) below, the case where the number of the modifying N,N-dimethylaminoethyl groups is x (x=1 to 7) is shown.

Structural Formula (5)

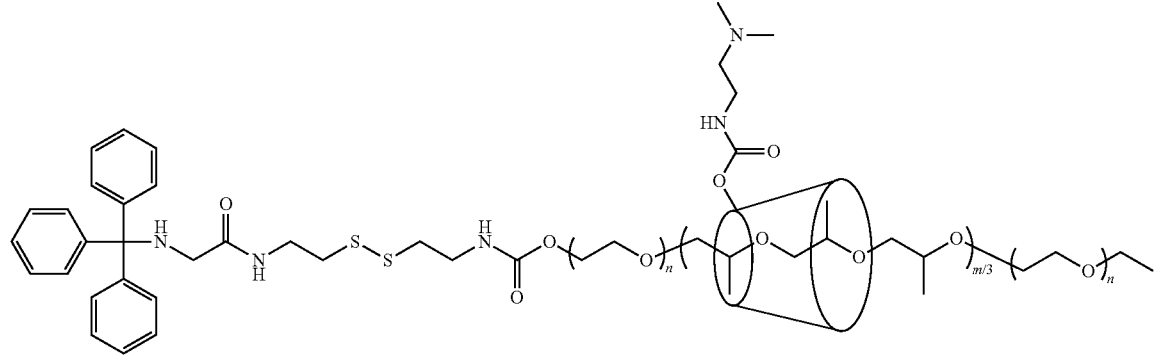

-continued

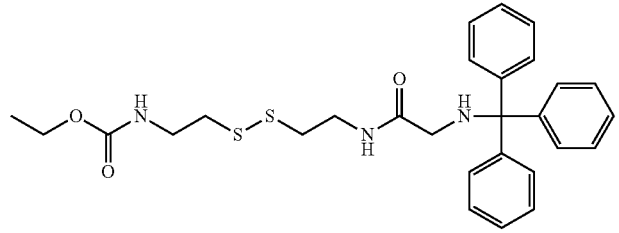

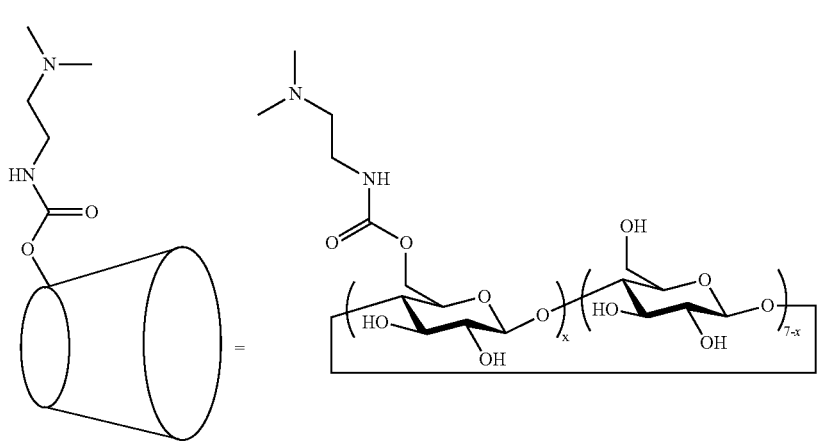

Formula (B)

Preparation Example 5: Preparation of Polyrotaxane-6

Water-soluble Polyrotaxane-6 (hereinafter, sometimes referred to as "HEE-SS-PRX") was obtained by introducing hydroxyethoxy ethyl (hereinafter, "HEE") groups into the β-CDs of the polyrotaxane having disulfide linkages at the ends which was prepared in the same manner as in Preparation Example 1 (the average number of threaded β-CDs per polyrotaxane molecule is 16.1; the average number of HEE groups is 64.7).

200 mg of the polyrotaxane having disulfide linkages at the ends was measured and dissolved in 15 mL of dimethylsulfoxide. 203 mg of 1,1'-carbonyldiimidazole was added, and the mixture was stirred at room temperature for 24 hours. Then, 624 μL of 2-(2-aminoethoxy)ethanol was added to the reaction solution, and the mixture was stirred for another 24 hours at room temperature. After the reaction, the mixture was transferred to a dialysis membrane of molecular weight cut-off of 3,500 (Spectra) to dialysis against ultrapure water, so as to remove unreacted material. By freeze-drying the recovered solution, 237.6 mg of polyrotaxane having a disulfide linkage at each of the ends and having been introduced with hydroxyethoxy ethyl groups (HEE-SS-PRX) was obtained.

FIG. 6 shows a proton nuclear magnetic resonance spectrum at 500 MHz for HEE-SS-PRX in heavy dimethylsulfoxide (Sigma-Aldrich).

The proton nuclear magnetic resonance spectrum confirmed that HEE-SS-PRX had a structure represented by the following Structural Formula (6). In below Structural Formula (6), "m" represents the number of polypropylene glycol repeating units (in Formula (6), "m/3" is denoted since three polypropylene glycol repeating units are shown in parentheses) and "n" represents the number of polyethylene glycol repeating units. In addition, in Structural Formula (6) below, only one β-CD, which is represented by following Formula (C), is shown. Further, in Formula (C) below, the case where the number of the modifying hydroxyethyl groups is x (x=1 to 7) is shown.

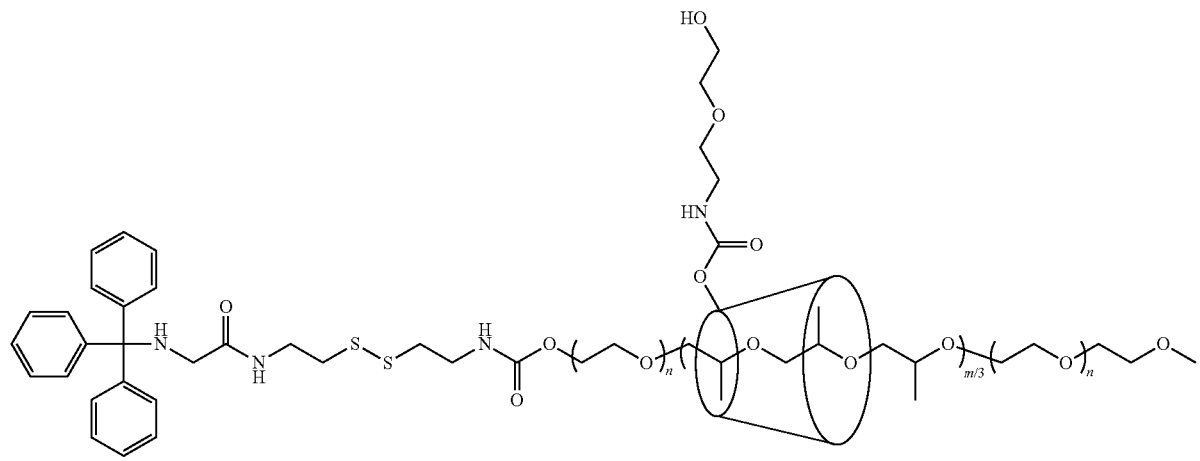

Structural Formula (6)

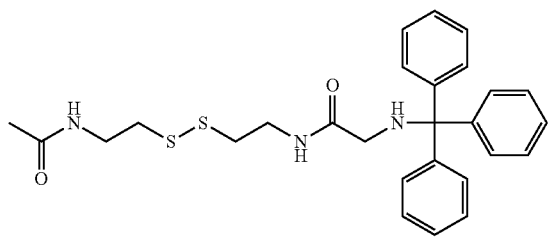

Formula (C)

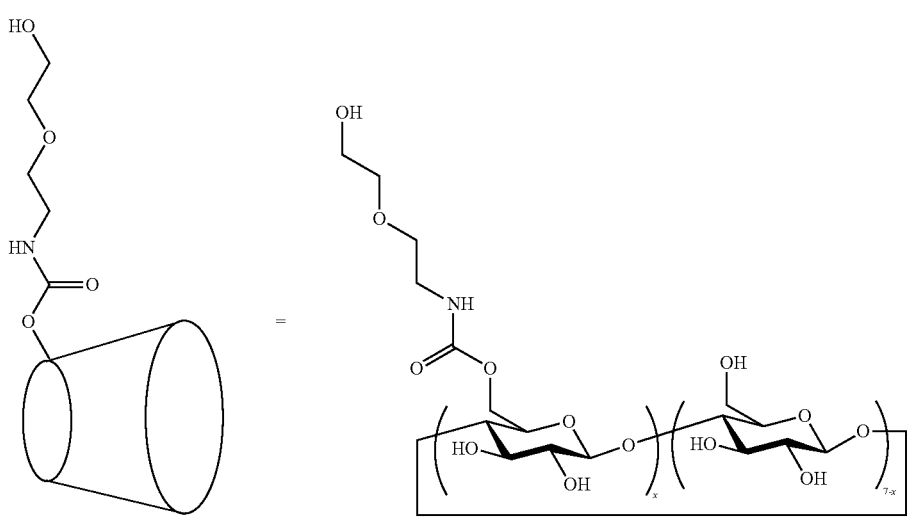

Test Example 1: Hemolysis Assay

Figure 7:
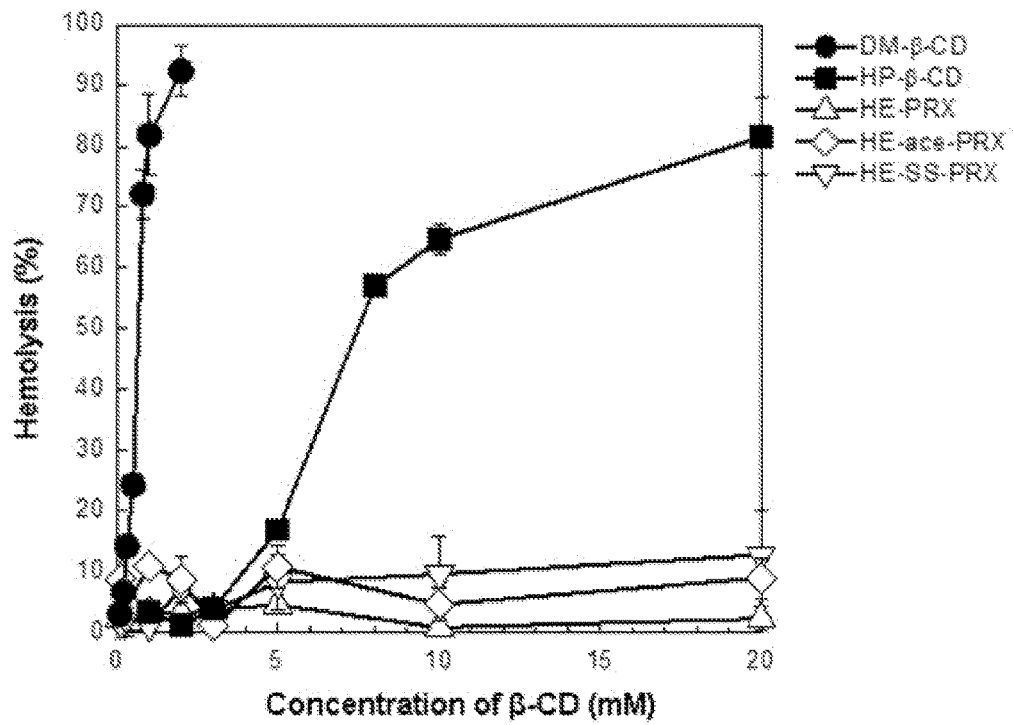
FIG. 7 is a graph showing results of hemolysis test of Test Example 1.

Rat erythrocyte suspensions (purchased from Kohjin Bio; cell count: $1\times10^8$ cells) in 200 μL of phosphate-buffered saline (hereinafter, sometimes referred to as "PBS") were incubated with the following samples of various concentrations (as the concentration of cyclodextrin) for 2 hours at 37° C. The erythrocytes were separated by centrifugation, and the supernatant (100 μL) was collected and aliquoted into 96-well plate (BD Falcon). The absorbance of the supernatant at 544 nm was measured by a microplate reader, ARVO-MX (Perkin Elmer). The hemolytic activities (%) were calculated according to the equation shown below, by setting the absorbance of supernatant after treatment with 0.1% Triton X-100 (Nacalai Tesque) as the hemolytic activity of 100%. The results are shown in FIG. 7.

<Samples>

(1) HE-SS-PRX (produced in Preparation Example 1)

(2) HE-ace-PRX (produced in Preparation Example 2)

(3) HE-PRX (produced in Comparative Preparation Example 1)

(4) Hydroxypropyl β-cyclodextrin (hereinafter, sometimes referred to as "HP-β-CD"; compound of Structural Formula (7) as shown below; purchased from Sigma-Aldrich; catalog number 332607; Structural Formula (7) shows the case where the number of the hydroxypropyl modifications as mentioned above is x (x=1 to 7).)

Structural Formula (7)

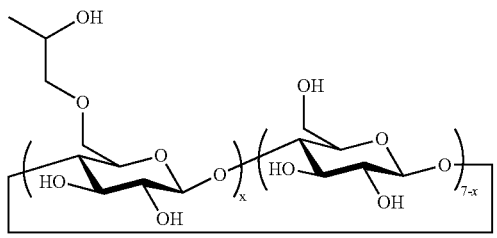

(5) 2,6-dimethyl-β-cyclodextrin (hereinafter, sometimes referred to as "DM-β-CD"; compound of Structural Formula (8) as shown below; Sigma-Aldrich, catalog number H0513)

Structural Formula (8)

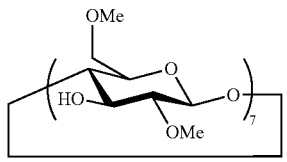

<Calculation of Hemolytic Activity>

Hemolytic activity (%)={(absorbance of supernatant after treatment with a sample)/(absorbance of supernatant after treatment with Triton X-100)}×100

In FIG. 7, "● (solid circle)" indicates the result for "DM-β-CD", "■ (solid square)" indicates the result for "HP-β-CD", "Δ (triangle)" indicates the result for "HE-PRX", "◊ (rhombus)" indicates the result for "HE-ace-PRX", and "∇ (inverted triangle)" indicates the result for "HE-SS-PRX".

The results shown in FIG. 7 demonstrate that HP-β-CD and DM-β-CD, which are cyclodextrins, induced hemolysis while HE-PRX, HE-SS-PRX and HE-ace-PRX, which are polyrotaxanes, showed negligible hemolysis even at the elevated concentration equivalent to 20 mM of cyclodextrin.

It is inferred that polyrotaxanes do not induce membrane disruption caused due to the hydrophobic cavity of cyclodextrin since the cavity is occupied with a polymer chain.

From these results, it is believed that polyrotaxanes are safer than cyclodextrins in terms of hemolysis.

Test Example 2: Accumulation of Cholesterol

Normal human dermal fibroblasts (hereinafter, referred to as "NHDF" or "NHDF cells"; obtained from Coriell Institute; number: GM05659) and human dermal fibroblasts derived from a Niemann-Pick type C disease patient (hereinafter, referred to as "NPC1" or "NPC1 cells"; obtained from Coriell Institute; number: GM03123) were used as follows to examine the cellular accumulation of cholesterol.

NPC1 cells were seeded on a 24-well plate (number of the cells: $2.5 \times 10^4$ cells/well) and incubated for 24 hours at 37° C., and then, the samples shown below were added at a concentration equivalent to 100 μM of cyclodextrin, and incubated for another 24 hours at 37° C.

After the incubation, the cells were fixed with 4% paraformaldehyde, and following the addition of filipin (Polysciences) in PBS adjusted to 100 μg/mL, were allowed to stand for 45 minutes at room temperature. After washing the cells three times with PBS, the localization of cholesterol was observed by using a confocal laser scanning microscope, FluoView FV10i (Olympus). Moreover, the amount of intracellular cholesterol accumulation was determined.

The quantification of the amount of intracellular cholesterol accumulation was carried out as follows.

After the incubation the cells were lysed with cell lysis buffer to obtain cell lysates, and the intracellular cholesterol was determined by Amplex Red Cholesterol Assay Kit (Invitrogen) while the total cellular protein content was determined with Micro BCA Protein Assay Kit (Thermo Fisher Scientific). The total intracellular cholesterol content is shown as total cholesterol content (nmol)/total protein content (mg).

For comparison, similar assays were performed for the case where the NHDF was contacted with no sample, as well as for the case where the NPC1 was contacted with no sample.

<Samples>
(1) HE-SS-PRX (produced in Preparation Example 1)
(2) HE-ace-PRX (produced in Preparation Example 2)
(3) HE-PRX (produced in Comparative Preparation Example 1)
(4) HP-β-CD (purchased from Sigma-Aldrich)
(5) DM-β-CD (purchased from Sigma-Aldrich)

Figure 8A:
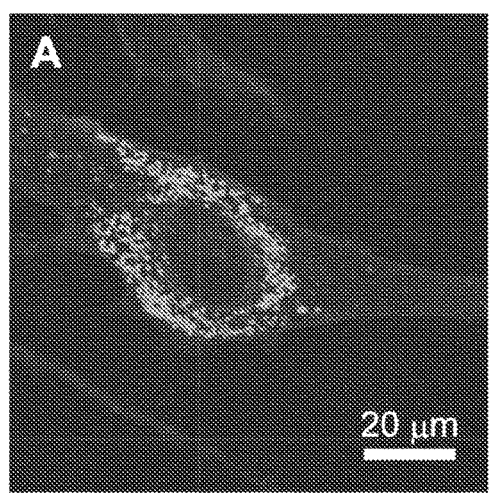
FIG. 8A is a diagram showing results of Test Example 2 in a case where Niemann-Pick Type C disease patient-derived dermal fibroblast cells were used and no sample was added.
Figure 8B:
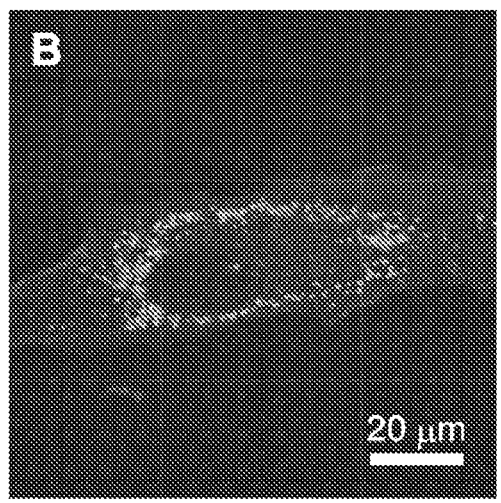
FIG. 8B is a diagram showing results of Test Example 2 in a case where Niemann-Pick Type C disease patient-derived dermal fibroblast cells were used and HP-β-CD was added as a sample.
Figure 8C:
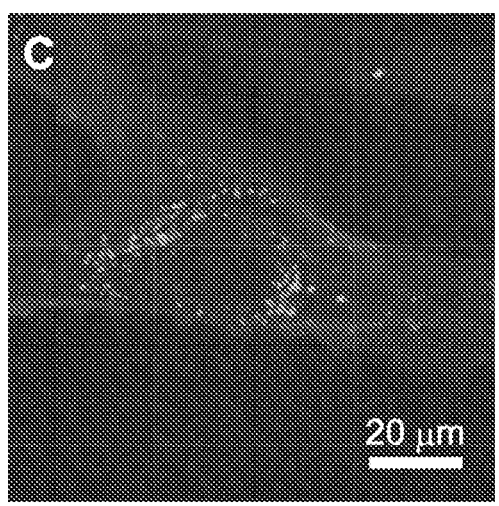
FIG. 8C is a diagram showing results of Test Example 2 in a case where Niemann-Pick Type C disease patient-derived dermal fibroblast cells were used and DM-β-CD was added as a sample.
Figure 8D:
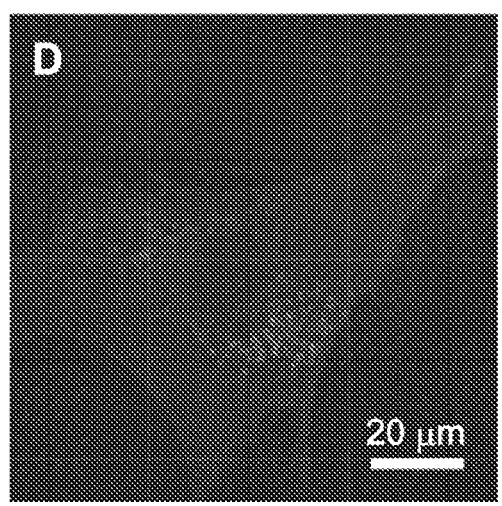
FIG. 8D is a diagram showing results of Test Example 2 in a case where Niemann-Pick Type C disease patient-derived dermal fibroblast cells were used and HE-SS-PRX was added as a sample.
Figure 8E:
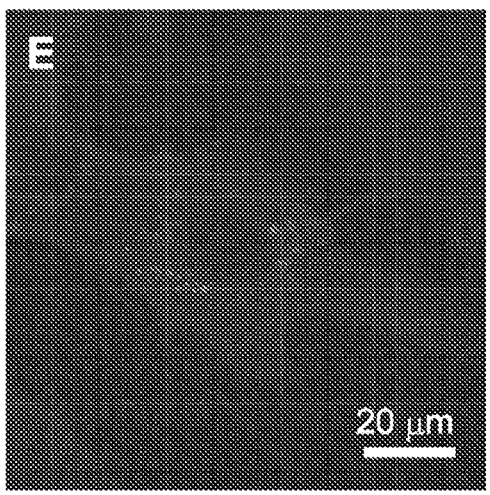
FIG. 8E is a diagram showing results of Test Example 2 in a case where Niemann-Pick Type C disease patient-derived dermal fibroblast cells were used and HE-ace-PRX was added as a sample.
Figure 8F:
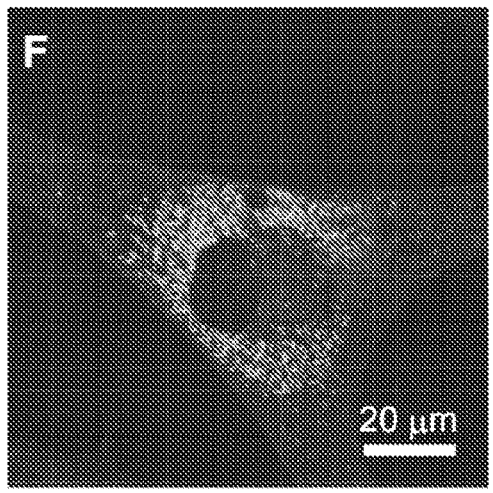
FIG. 8F is a diagram showing results of Test Example 2 in a case where Niemann-Pick Type C disease patient-derived dermal fibroblast cells were used and HE-PRX was added as a sample.
Figure 8G:
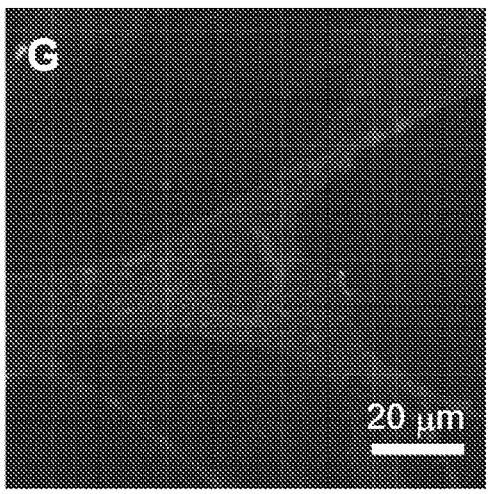
FIG. 8G is a diagram showing results of Test Example 2 in a case where healthy subject-derived dermal fibroblast cells were used and no sample was added.
Figure 9:
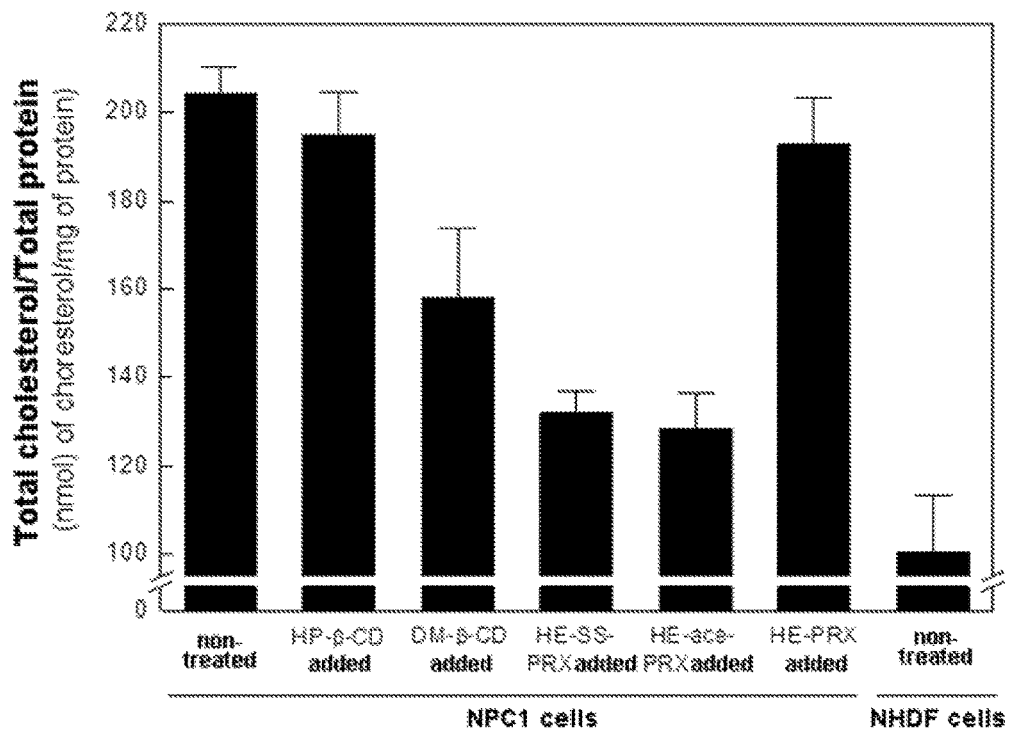
FIG. 9 is a graph showing quantitative results of the amount of cholesterol accumulated in cells of Test Example 2.

FIG. 8A to FIG. 8G show the intracellular accumulation of cholesterol observed with a confocal microscope, and FIG. 9 shows the quantified results of the intracellular cholesterol accumulation.

FIG. 8A shows the result of the case where NPC1 cells were used and none of the samples were added; FIG. 8B shows the result of the case where NPC1 cells were used and HP-β-CD was added as a sample; FIG. 8C shows the result of the case where NPC1 cells were used and DM-β-CD was added as a sample; FIG. 8D shows the result of the case where NPC1 cells were used and HE-SS-PRX was added as a sample; FIG. 8E shows the result of the case where NPC1 cells were used and HE-ace-PRX was added as a sample; FIG. 8F shows the result of the case where NPC1 cells were used and HE-PRX was added as a sample; and FIG. 8G shows the result of the case where NHDF cells were used and none of the samples were added. In each image, the part shown in white indicates cholesterol. The amount added of each sample is equivalent to 100 μM of cyclodextrin.

In FIG. 9, in order from the left, the results on the following are shown: "the case where NPC1 cells were used and none of the samples were added (non-treated)", "the case where NPC1 cells were used and HP-β-CD was added as a sample (HP-β-CD added)", "the case where NPC1 cells were used and DM-β-CD was added as a sample (DM-β-CD added)", "the case where NPC1 cells were used and HE-SS-PRX was added as a sample (HE-SS-PRX added)", "the case where NPC1 cells were used and HE-ace-PRX was added as a sample (HE-ace-PRX added)", "the case where NPC1 cells were used and HE-PRX was added as a sample (HE-PRX added)", and "the case where NPC1 cells were used and HE-SS-PRX was added as a sample (HE-SS-PRX added)", and "the case where NHDF cells were used and none of the samples were added (non-treated)". The amount added of each sample is equivalent to 100 μM of cyclodextrin.

The results of FIG. 8A to FIG. 8G show that the NPC1 cells contain a larger amount of intracellular cholesterol as compared to the NHDF cells.

When the NPC1 cells were incubated with DM-β-CD, the fluorescence intensity was reduced, indicating that the excretion of cholesterol was facilitated.

On the other hand, when the NPC1 cells were treated with HE-SS-PRX or HE-ace-PRX which has intracellularly degradable linkages, the fluorescence intensity decreased to the level similar to that of the NHDF cells, indicating a superior cholesterol removal as compared to DM-β-CD, and to HP-β-CD which is currently on clinical trial.

The fluorescence intensity induced by HE-PRX which does not have any intracellularly degradable linkage was higher than those cells treated with HE-SS-PRX and HE-ace-PRX which have intracellularly degradable linkages, indicating an inferior cholesterol removal.

FIG. 9 demonstrates that HP-β-CD, which is currently on a clinical trial, produced a subtle reduction of cholesterol at the concentration tested, while DM-β-CD which has the highest cholesterol inclusion among the known samples was capable of removing more cholesterol than HP-β-CD.

On the other hand, NPC1 cells treated with HE-ace-PRX or DMAE-ace-PRX, which has intracellularly degradable linkages, showed improved removal of cholesterol as compared to HP-β-CD and DM-β-CD, or as compared to HE-PRX which does not have any intracellularly degradable linkage, demonstrating their remarkable activities.

The above results demonstrate that the NPC1 cells treated with HE-SS-PRX or HE-ace-PRX which has intracellularly degradable linkages show a markedly reduced cholesterol accumulation. The intracellular release of cyclodextrins as a result of the intracellular cleavage of disulfide linkages or acetal linkages is thought to have caused the removal of the intracellular cholesterol.

Thus, the foregoing shows that polyrotaxanes, which comprise a plurality of cyclic molecules threaded along a linear molecule having bulky substituents linked via intracellularly degradable linkages at both ends, are useful as a minimally invasive therapeutic agent for lysosomal diseases, including Niemann-Pick type C disease, which has an excellent activity for removing cholesterol from the affected cells.

Test Example 3: Cytotoxicity Assay

The cytotoxicity of polyrotaxanes and cyclodextrin derivatives was examined by using NPC1 cells as follows.

NPC1 cells were seeded on a 96-well plate (cell count: $1 \times 10^4$ cells/well), and incubated in Dulbecco's modified Eagle's medium (Gibco) containing 10% fetal bovine serum (Gibco) for 24 hours at 37° C. After replacing the medium with 90 μL of Dulbecco's modified Eagle's medium, 10 μL of the following samples were added to each well at a range of concentration equivalent to 0.1 mM to 20 mM of cyclodextrin, and were incubated for another 24 hours at 37° C. Then, 10 μL of Cell Counting Kit-8 (Dojindo Laboratories) was added to each well, and further allowed to stand for 1 hour at 37° C.

The absorbance at 450 nm was measured with a Multiskan FC plate reader (Thermo Fisher). The cell viability (%) was calculated according to the equation shown below, by setting the absorbance of the cells to which phosphate buffer solution was added in place of the sample as the cell viability of 100%. The results are shown in FIG. 10.

<Samples>
(1) HE-SS-PRX (produced in Preparation Example 1)
(2) HE-PRX (produced in Comparative Preparation Example 1)
(3) HP-β-CD (purchased from Sigma-Aldrich)
(4) DM-β-CD (purchased from Sigma-Aldrich)
<Calculation of Cell Viability>

Cell viability (%)={(absorbance of cells incubated with a sample added)/(absorbance of cells incubated with PBS added)}×100

Figure 10:
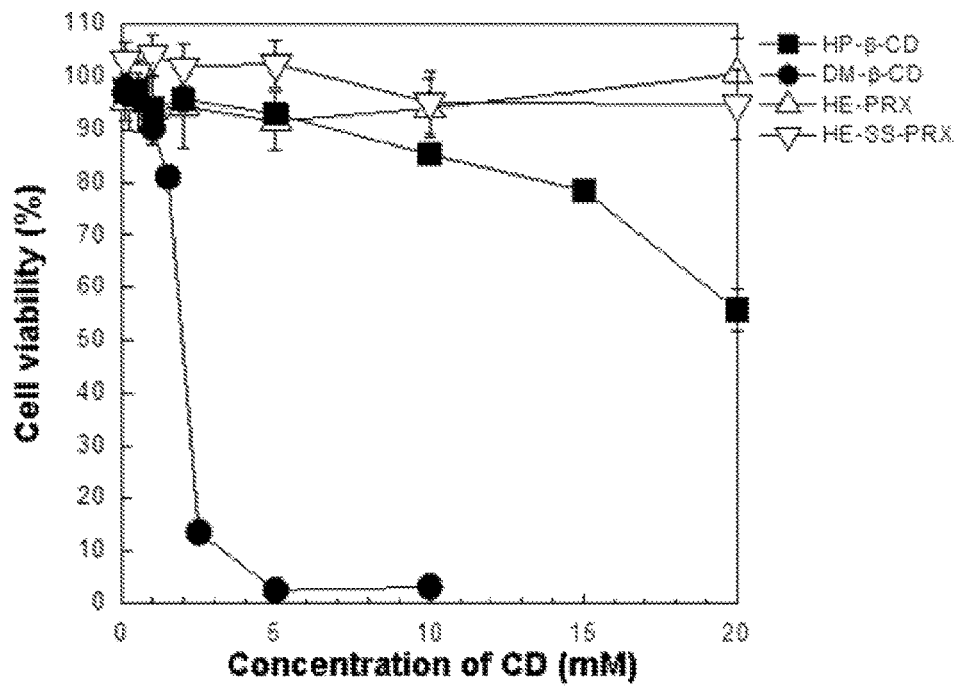
FIG. 10 is a graph showing results of evaluation of cytotoxicity of Test Example 3.

In FIG. 10, "● (solid circle)" indicates the result for "DM-β-CD", "■ (solid square)" indicates the result for "HP-β-CD", "Δ (triangle)" indicates the result for "HE-PRX", and "∇ (inverted triangle)" indicates the result for "HE-SS-PRX".

The results shown in FIG. 10 demonstrate that HP-β-CD and DM-β-CD, which are cyclodextrin derivatives, lowered the cell viability, while HE-PRX and HE-SS-PRX, which are polyrotaxanes, did not lower the cell viability even at the elevated concentration equivalent to 20 mM of cyclodextrin.

It is inferred that polyrotaxanes do not induce cellular membrane disruption since the cavity of cyclodextrin is occupied with a polymer chain.

From these results, it is believed that polyrotaxanes are safer than cyclodextrins in terms of cytotoxicity.

Test Example 4: Localization Observed with Confocal Microscope

<Sample Preparation>

In order to study the localization of polyrotaxanes and cyclodextrin derivatives upon contact with NPC1, HE-SS-PRX labeled with fluorescein isothiocyanate ethylenediamine (FITC-EDA) (hereinafter, referred to as "FITC-labeled HE-SS-PRX") and HP-β-CD (hereinafter, referred to as "FITC-labeled HP-β-CD") were prepared as follows and used as samples.

—Preparation of FITC-labeled HE-SS-PRX—

30 mg of HE-SS-PRX prepared in Preparation Example 1 was dissolved in 3 mL of DMSO. 4.83 mg of 1,1'-carbonyldiimidazole was added, and the mixture was stirred at room temperature for 24 hours. 2.67 mg of FITC-EDA (synthesized according to previously reported literature: N V. Nukolova et al. Biomaterials 32(23), 5417-5426 (2011)) was added, and the mixture was stirred for another 24 hours at room temperature. After the reaction, the mixture was transferred to a dialysis membrane of molecular weight cut-off of 3,500 (Spectra) to dialysis against ultrapure water, so as to remove unreacted FITC-EDA. By lyophilizing the recovered aqueous solution, 13.2 mg of FITC-labeled HE-SS-PRX was obtained. The degree of substitution was determined by measuring the absorbance at 494 nm with an ultraviolet-visible spectrophotometer, and the polyrotaxane was confirmed to be labeled with 0.04 molecules of FITC per β-CD molecule.

—Preparation of FITC-Labeled HP-β-CD—

200 mg of HP-β-CD (Sigma Aldrich) was dissolved in 10 mL of DMSO. 66.6 mg of 1,1'-carbonyldiimidazole was added, and the mixture was stirred at room temperature for 24 hours. 61.6 mg of FITC-EDA was added, and the mixture was stirred for another 24 hours at room temperature. After the reaction, the mixture was transferred to a dialysis membrane of molecular weight cut-off of 1,000 (Spectra) to dialysis against ultrapure water for 10 days, so as to remove unreacted FITC-EDA. By lyophilizing the recovered aqueous solution, 16.9 mg of FITC-labeled HP-β-CD (FITC-HP-β-CD) was obtained. The degree of FITC substitution was determined in a similar manner as the above. Unlabeled HP-β-CD and FITC-HP-β-CD were mixed to adjust the degree of FITC substitution to be 0.04 molecules per HP-β-CD molecule.

<Observation of Localization>

NPC1 cells were seeded on a 35 mm glass bottom dish (IWAKI) (cell count: $1 \times 10^4$ cells/dish), and incubated in Dulbecco's modified Eagle's medium containing 10% fetal bovine serum for 24 hours at 37° C. After replacing the medium with 900 μL of Dulbecco's modified Eagle's medium, 100 μL of the above-mentioned samples were added to each dish at the concentration equivalent to 5 mM of cyclodextrin, and were incubated for another 24 hours at 37° C.

The cells were washed twice with phosphate buffer solution, and then fixed by adding 1 mL of 4% paraformaldehyde and allowing to stand at room temperature for 15 minutes.

The cells were washed twice with phosphate buffer solution, and the plasma membranes were permeabilized by adding 1 mL of 0.1% Triton X-100 and allowing to stand at room temperature for 10 minutes.

After washing the cells twice with phosphate buffered saline, a mouse monoclonal anti-early endosome antigen 1 (EEA1) antibody (BD Bioscience), a mouse monoclonal anti-CD63 antibody (BioLegend), and a mouse monoclonal anti-lysosomal-associated membrane protein 1 (LAMP1) antibody (Santa Cruz), each diluted with phosphate buffered saline containing 1% bovine serum albumin, were added to each dish, respectively, and allowed to stand at room temperature for 1 hour.

Then, the cells were washed three times with phosphate buffer solution, Alexa Fluor 647-conjugated goat anti-mouse IgG solution diluted with phosphate buffer solution containing 1% bovine serum albumin was added, and the cells were allowed to stand at room temperature for 30 minutes. Then, the cells were washed three times with phosphate buffer solution.

Microscopic observation was performed with FluoView FV10i (Olympus).

To clarify the details of the intracellular localization of FITC-labeled HP-β-CD and FITC-labeled HE-PRX by fluorescence microscopic observation, early endosomes, late endosomes, and lysosomes were immunostained with EEA1, CD63, and LAMP1. The results are shown in FIG. 11A to FIG. 11F.

Figure 11A:
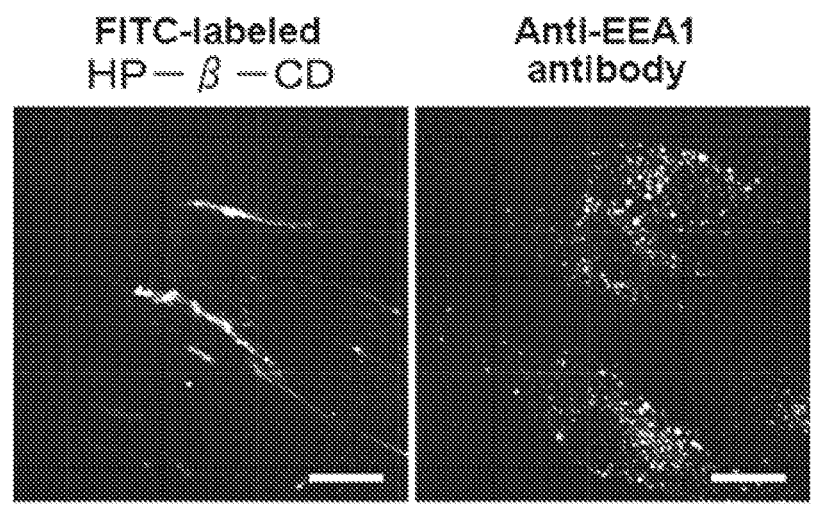
FIG. 11A is the first diagram showing a fluorescent microscope image of Test Example 4 (left: FITC-labeled HP-β-CD, right: anti-EEA1 antibody).
Figure 11B:
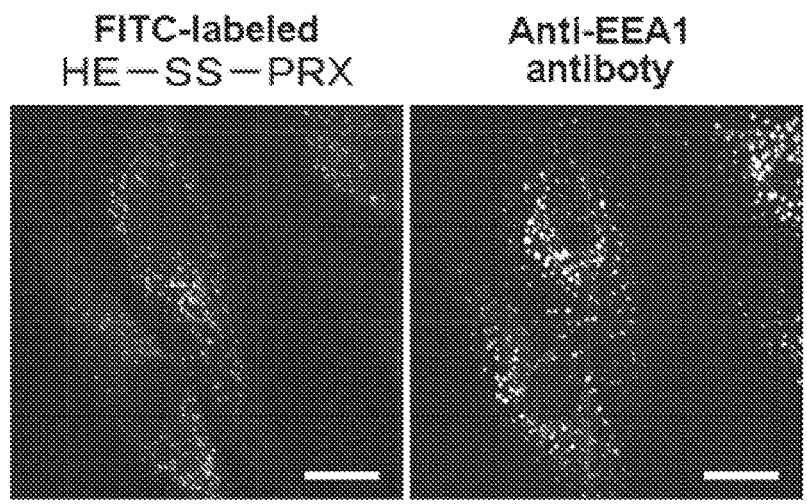
FIG. 11B is the second diagram showing a fluorescent microscope image of Test Example 4 (left: FITC-labeled HE-SS-PRX, right: anti-EEA1 antibody).
Figure 11C:
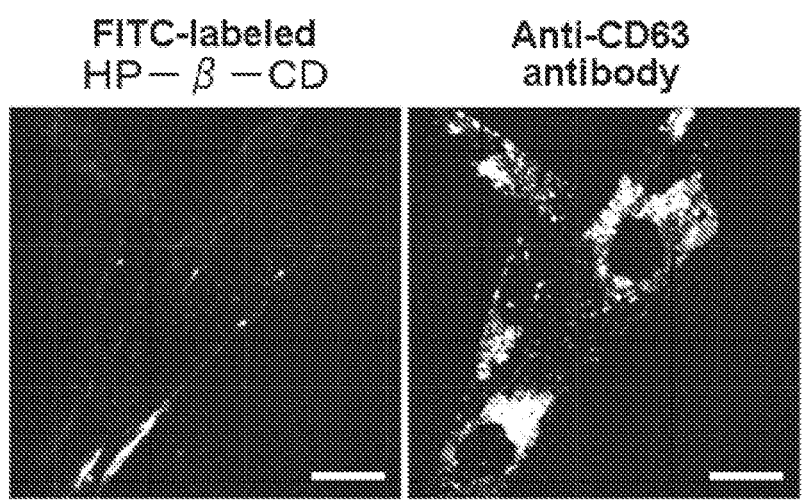
FIG. 11C is the third diagram showing a fluorescent microscope image of Test Example 4 (left: FITC-labeled HP-β-CD, right: anti-CD63 antibody).
Figure 11D:
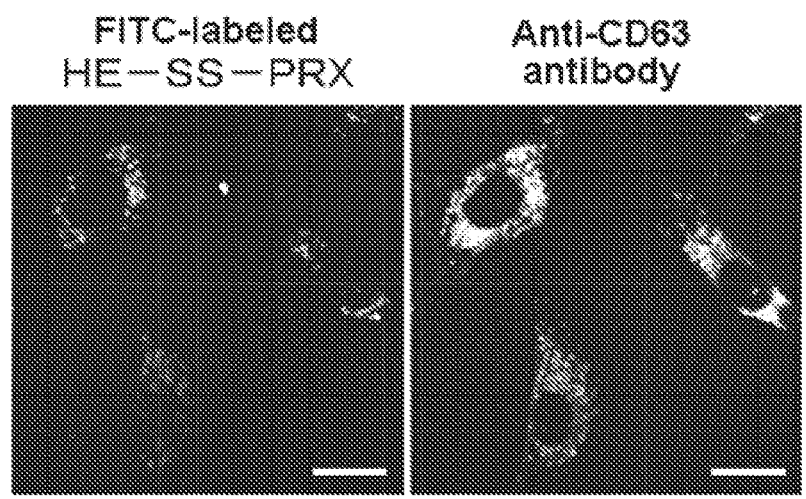
FIG. 11D is the fourth diagram showing a fluorescent microscope image of Test Example 4 (left: FITC-labeled HE-SS-PRX, right: anti-CD63 antibody).
Figure 11E:
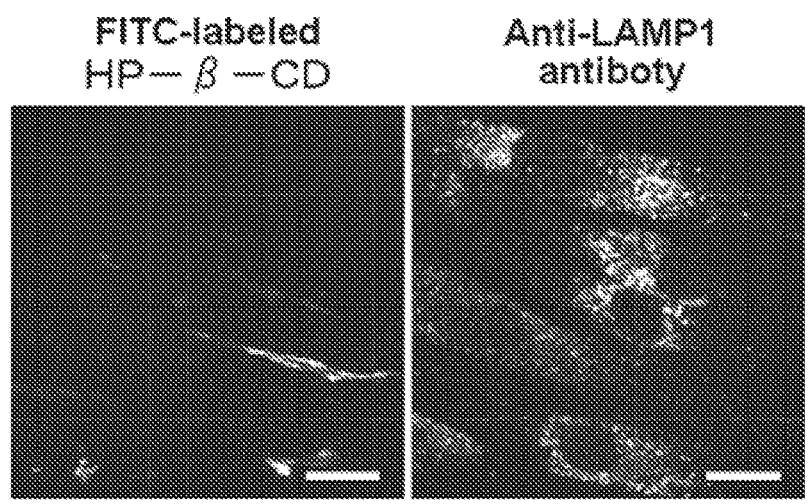
FIG. 11E is the fifth diagram showing a fluorescent microscope image of Test Example 4 (left: FITC-labeled HP-β-CD, right: anti-LAMP1 antibody).
Figure 11F:
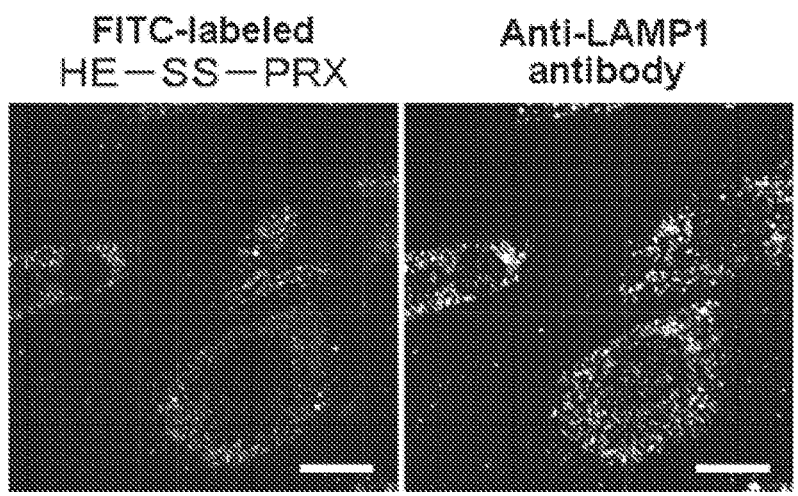
FIG. 11F is the sixth diagram showing a fluorescent microscope image of Test Example 4 (left: FITC-labeled HE-SS-PRX, right: anti-LAMP1 antibody).
Figure 12:
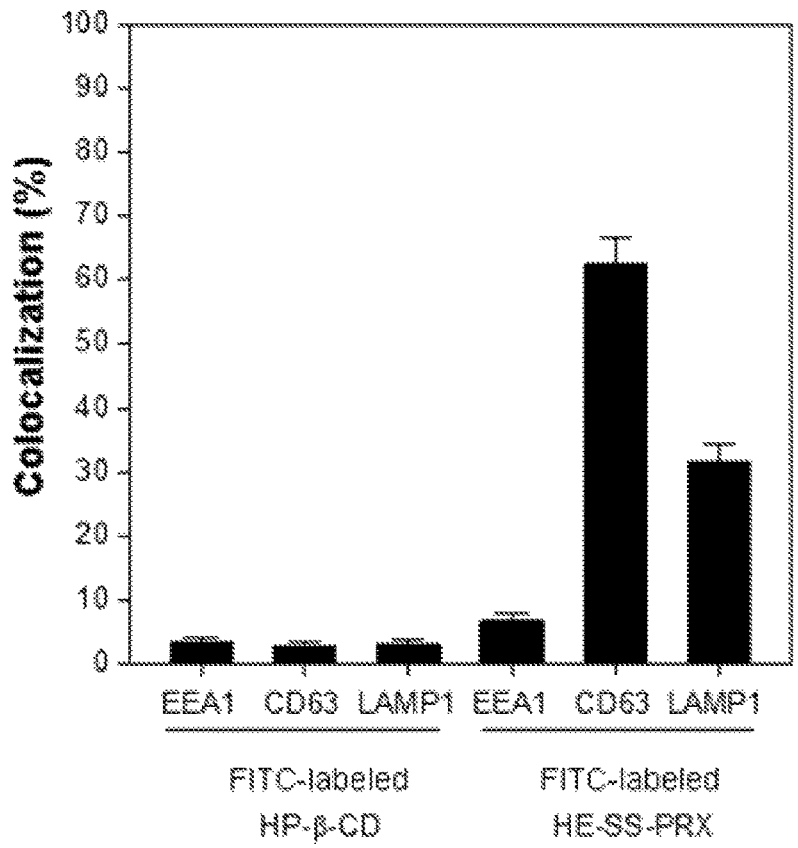
FIG. 12 is a graph showing results obtained for co-localization rate of FITC-labeled HP-β-CD and FITC-labeled HE-PRX with respect to EEA1, CD63, or LAMP1 positive vesicles.

FIG. 12 shows the colocalization percentage of FITC-labeled HP-β-CD and FITC-labeled HE-PRX on EEA1-, CD63-, or LAMP1-positive vesicles as calculated from the images of FIG. 11A to FIG. 11F obtained using FluoView Viewer (Olympus). The calculation was done by obtaining the colocalization percentage on 20 cells for each of EEA1, CD63, and LAMP1-positive vesicles, to obtain the mean and standard error.

The results observed from FIG. 11A to FIG. 12 show that the colocalization of FITC-labeled HP-β-CD to early endosomes (EEA1 positive vesicles), late endosomes (CD63-positive vesicles), and lysosomes (LAMP1-positive vesicles) is negligible, and most of the molecules are localized in the vicinity of the cell membrane. This is probably due to the interaction of the cavity of β-CD with lipid and cholesterol present in the cell membrane. This result is consistent with the above results showing that β-CD tightly interacts with the plasma membrane and induces membrane disruption and hemolysis.

FITC-labeled HE-PRX was localized to late endosomes (CD63-positive vesicles), or lysosomes (LAMP1-positive vesicles). It is thought that the polyrotaxane was taken into cells by endocytosis and then reached the late endosomes and lysosomes. Since polyrotaxane does not interact with the plasma membrane as the cavity of β-CD is occupied with a polymer chain, as a result it is expected to be taken into cells via endocytosis.

From the above results, it was found that FITC-labeled HP-β-CD and FITC-labeled HE-SS-PRX significantly differ in the cellular localization and site of action.

Test Example 5: Cholesterol Removal Effect

The cholesterol removal from NPC1 by polyrotaxanes and cyclodextrin derivatives was examined in further detail.

NPC1 cells were seeded on a 24 well plate (BD Falcon) (cell count: $2.5 \times 10^4$ cells/dish), and incubated in Dulbecco's modified Eagle's medium containing 10% fetal bovine serum for 24 hours at 37° C. After replacing the medium with 270 μL of Dulbecco's modified Eagle's medium, 30 μL of the following samples were added to each well at a range of concentration equivalent to 0.01 mM to 100 mM of cyclodextrin, and were incubated for another 24 hours at 37° C.

Then, the cells were washed twice with phosphate-buffered solution, and 0.25% trypsin-EDTA solution (Gibco) was added to each well to peel the cells. The cells were collected into a 1.5 mL tube, and washed twice with phosphate buffered saline. Then, cell lysis solution (including 50 mM phosphate buffer solution, 500 mM sodium chloride, 25 mM cholic acid, and 0.5% Triton X-100) was added to each tube to lyse the cells.

In each cell lysate, the total cholesterol was quantified by Amplex Red Cholesterol Assay Kit (Invitrogen), and the total protein was quantified by micro BCA Protein Assay Kit (Thermo Fisher Scientific). The total cellular cholesterol content is shown as total cholesterol content (nmol)/total protein content (mg).

For comparison, similar assays were performed for the case where NHDF was contacted with no sample, and for the case where NPC1 was contacted with no sample.

<Samples>
(1) HE-SS-PRX (produced in Preparation Example 1)
(2) HE-PRX (produced in Comparative Preparation Example 1)
(3) HP-β-CD (purchased from Sigma-Aldrich)
(4) DM-β-CD (purchased from Sigma-Aldrich)

Figure 13:
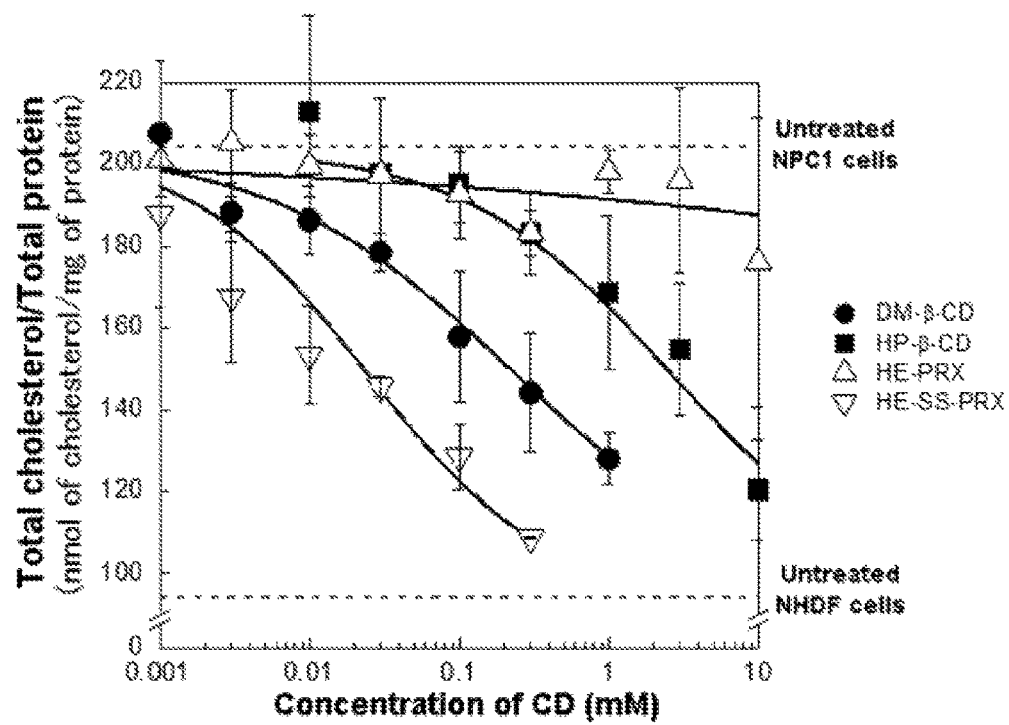
FIG. 13 is a graph showing results of cholesterol removing effect of Test Example 5.

The results are shown in FIG. 13. In FIG. 13, "● (solid circle)" indicates the result for "DM-β-CD", "■ (solid square)" indicates the result for "HP-β-CD", "Δ (triangle)" indicates the result for "HE-PRX", and "∇ (inverted triangle)" indicates the result for "HE-SS-PRX".

The half maximal effective concentration (ED50) was determined from the dose-response curve for cholesterol accumulation, and ED50s for HP-β-CD, DM-β-CD, and HE-SS-PRX were found to be 2.59 mM, 0.23 mM, and 0.024 mM, respectively.

The above results demonstrate that HE-SS-PRX with intracellularly degradable linkages can remove cholesterol from NPC1 at 10- to 100-fold lower concentration as compared to existing β-CD derivatives. In addition, non-degradable HE-PRX did not show any significant cholesterol reduction at the concentration range of this experiment.

From these results, it is thought that the intracellular cleavage of degradable linkages of the polyrotaxane and the accompanying release of β-CDs have resulted in the cholesterol removal at low concentration.

Test Example 6: Cholesterol Removal Effect

Similar assays to Test Example 5 were performed except that the following samples were used in order to investigate how the type of degradable linkage in polyrotaxane influences to cholesterol removal from NPC1.

<Samples>
(1) HE-PRX (produced in Comparative Preparation Example 1)
(2) HE-ace-PRX (produced in Preparation Example 2)
(3) HE-COO-PRX (produced in Preparation Example 3)
(4) HE-SS-PRX (produced in Preparation Example 1)

Figure 14:
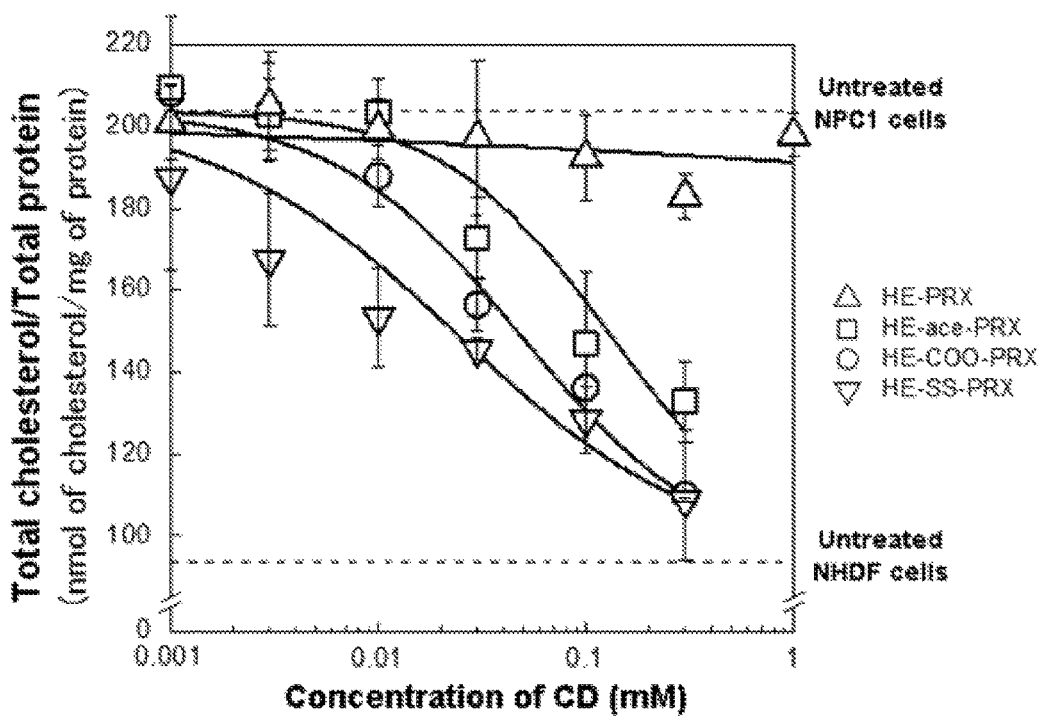
FIG. 14 is a graph showing results of cholesterol removing effect of Test Example 6.

The results are shown in FIG. 14. In FIG. 14, "Δ (triangle)" indicates the result for "HE-PRX", "■ (open square)" indicates the result for "HE-ace-PRX", "○" indicates the result for "HE-COO-PRX", and "▽ (inverted triangle)" indicates the result for "HE-SS-PRX".

ED50 was determined from the dose-response curve for cholesterol accumulation, and ED50s for HE-ace-PRX, HE-COO-PRX, and HE-SS-PRX were found to be 0.13 mM, 0.49 mM, and 0.024 mM, respectively.

These results demonstrate that any of the polyrotaxanes having intracellularly degradable linkages are capable of removing cholesterol from NPC1. Especially the polyrotaxane having disulfide linkages was found to have a high cholesterol removal activity. The differences in cholesterol removal activity depending on the type of the degradable linkage in polyrotaxane are thought to be related to the intracellular cleavage efficiency of degradable linkages.

Test Example 7-1: Cholesterol Removal Effect

Similar assays to Test Example 5 were performed except that the following samples were used in order to investigate how the type of functional group introduced into cyclodextrins in polyrotaxane influences to cholesterol removal from NPC1.
<Samples>
(1) HE-SS-PRX (produced in Preparation Example 1)
(2) DMAE-SS-PRX (produced in Preparation Example 4)

Figure 15A:
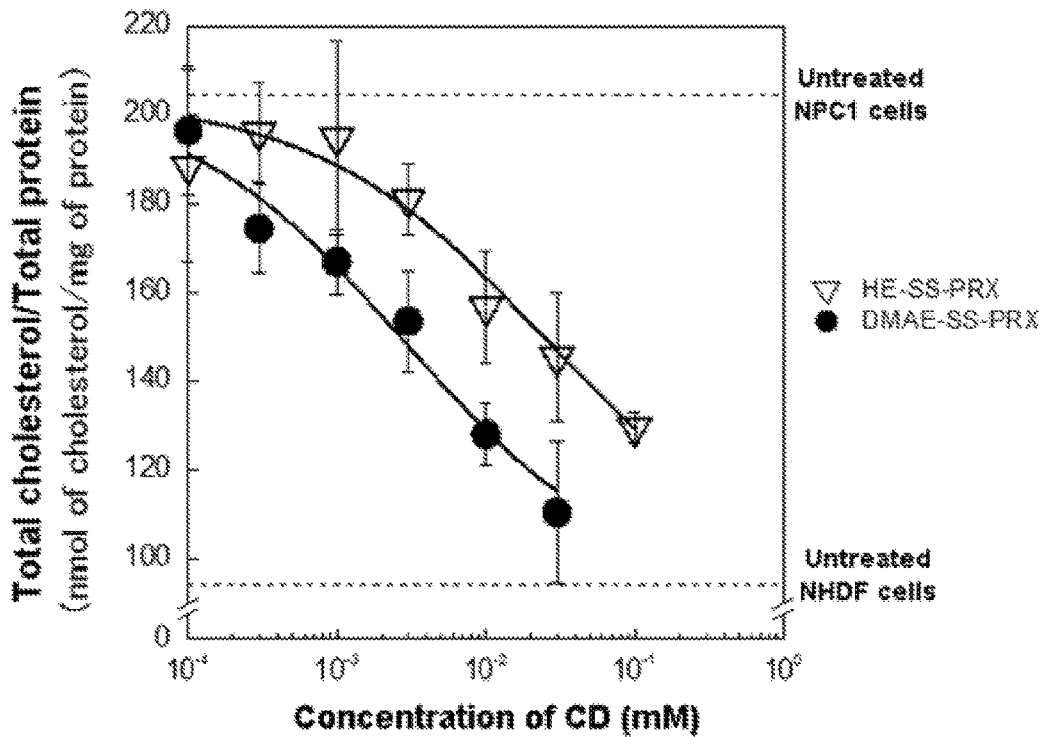
FIG. 15A is a graph showing results of cholesterol removing effect of Test Example 7-1.

The results are shown in FIG. 15A. In FIG. 15A, "▽ (inverted triangle)" indicates the result for "HE-SS-PRX" and "● (solid circle)" indicates the result for "DM-β-CD".

ED50 was determined from the dose-response curve for cholesterol accumulation, and ED50s for HE-SS-PRX and DMAE-SS-PRX were found to be 0.026 mM and 0.0028 mM, respectively.

The above results demonstrate that the functional group used for polyrotaxane modification influences the cholesterol removal from NPC1 by polyrotaxane. These results were probably due to the change in polyrotaxane uptake into cells. Especially, the polyrotaxane introduced with electrostatically charged DMAE groups strongly interacts with the plasma membrane electrostatically, and is thought to be taken up into cells efficiently.

Test Example 7-2: Amount of Cellular Uptake

The uptake into cells of each of the polyrotaxanes was determined by flow cytometry as follows.
<Sample Preparation>
To investigate the polyrotaxane uptake into cells, FITC-labeled HE-SS-PRX and DMAE-SS-PRX modified with fluorescein isothiocyanate ethylenediamine (FITC-EDA) (hereinafter, referred to as "FITC-labeled DMAE-SS-PRX") were prepared as follows, and were used as samples.
—Preparation of FITC-Labeled HE-SS-PRX—
The preparation was done in the same manner as in Test Example 4.
—Preparation of FITC-Labeled DMAE-SS-PRX—
30 mg of DMAE-SS-PRX prepared in Preparation Example 4 was dissolved in 5 mL of DMSO. 0.76 mg of 1,1'-carbonyldiimidazole was added, and the mixture was stirred at room temperature for 24 hours. 4.2 mg of FITC-EDA was added, and the mixture was stirred for another 24 hours at room temperature. After the reaction, the mixture was transferred to a dialysis membrane of molecular weight cut-off of 3,500 (Spectra) to dialysis against ultrapure water, so as to remove unreacted FITC-EDA. By lyophilizing the recovered aqueous solution, 27.5 mg of FITC-labeled DMAE-SS-PRX was obtained. The degree of substitution was determined by measuring the absorbance at 494 nm with an ultraviolet-visible spectrophotometer. Unlabeled DMAE-SS-PRX and FITC-DMAE-SS-PRX were mixed to adjust the degree of FITC substitution to be 0.04 molecules per DMAE-SS-PRX molecule.
<Flow Cytometry>
NPC1 cells were seeded on a 24 well plate (BD Falcon) (cell count: $1 \times 10^5$ cells/dish), and incubated in Dulbecco's modified Eagle's medium containing 10% fetal bovine serum for 24 hours at 37° C. After replacing the medium with 270 µL of Dulbecco's modified Eagle's medium, 30 µL of the following samples were added to each well at a range of concentration equivalent to 0.01 mM to 25 mM of cyclodextrin, and were incubated for another 24 hours at 37° C.

Then, the cells were washed twice with phosphate-buffered solution, and 0.25% trypsin-EDTA solution (Gibco) was added to each well to peel the cells. The cells were collected into a 1.5 mL tube, and washed twice with phosphate buffered saline. Then, phosphate buffer solution containing 0.1% bovine serum albumin was added, and the cells were filtered through 35 µm cell strainer (BD Falcon).

Figure 15B:
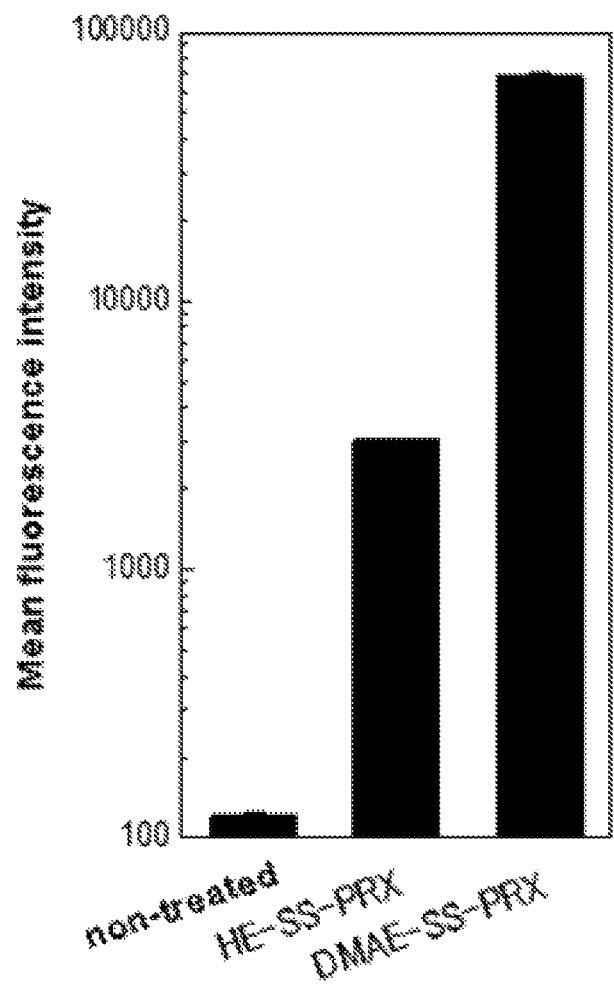
FIG. 15B is a graph showing results of flow cytometry of Test Example 7-2.

The fluorescence intensity of the cells was determined by FACSCanto II (BD Bioscience). 10,000 cells were counted, and the average value is shown in FIG. 15B.

A comparison of the flow cytometric results of the uptake into cells with FITC-labeled HE-SS-PRX and FITC-labeled DMAE-SS-PRX revealed a 22.6-fold higher fluorescence intensity for FITC-labeled DMAE-SS-PRX as compared to FITC-labeled HE-SS-PRX (in FIG. 15B, HE-SS-PRX indicates the result for FITC-labeled HE-SS-PRX, and DMAE-SS-PRX indicates the result for FITC-labeled DMAE-SS-PRX). From these results, it is thought that DMAE-SS-PRX is incorporated into cells efficiently, and is capable of removing cholesterol from NPC1 at lower concentrations than HE-SS-PRX.

Test Example 8: Observation of Autophagosomes by Immunostaining

NPC1 cells were seeded on a 35 mm glass bottom dish (IWAKI) (cell count: $1.5 \times 10^4$ cells/dish), and incubated at 37° C. under a 5% $CO_2$ atmosphere for one day, followed by the addition of the following samples and another 24-hour incubation.

After the culturing, the cells were fixed with 4% paraformaldehyde (Wako) for 10 minutes, treated with 50 µg/ml digitonin solution (Tokyo Chemical Industry) for 5 minutes to permeabilize the plasma membrane, and blocked with 1% BSA/PBS solution for 30 minutes.

The cells were then treated with Rabbit polyclonal anti-LC3 antibody (MBL) diluted to 1:200 with 1% BSA for one day at 4° C. After washing with PBS, the cells were stained with Alexa Fluor 488-conjugated goat anti-rabbit IgG (Abcam) (diluted to 1:1,000 with 1% BSA solution) for 30 minutes. After washing with PBS, the cells were observed by FluoView FV-10i (Olympus).

For comparison, similar assays were performed for the case where NHDF was contacted with no sample, and for the case where NPC1 was contacted with no sample.
<Samples>
(1) HEE-SS-PRX (produced in Preparation Example 5; the amount added was equivalent to 0.01 mM to 1 mM of cyclodextrin concentration)
(2) HP-β-CD (Sigma-Aldrich; the amount added was 0.1 mM to 10 mM)

Figure 16A:
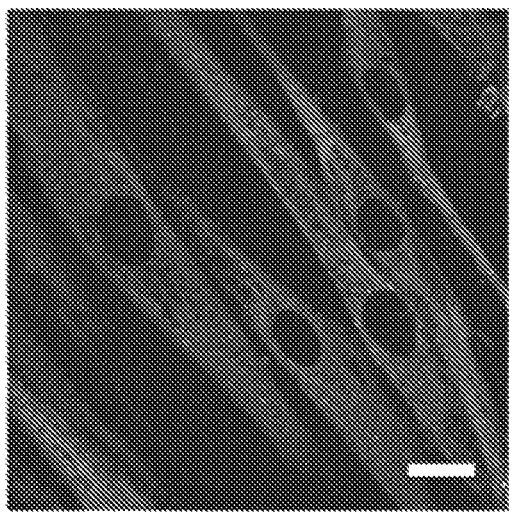
FIG. 16A is a diagram showing an image of LC3-stained NHDF (no sample added) in Test Example 8.
Figure 16B:
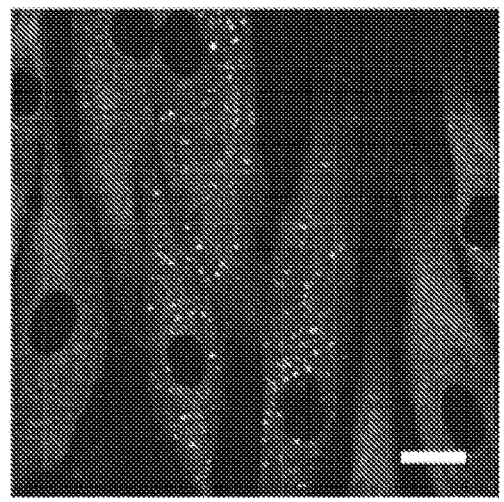
FIG. 16B is a diagram showing an image of LC3-stained NPC1 (no sample added) in Test Example 8.
Figure 16C:
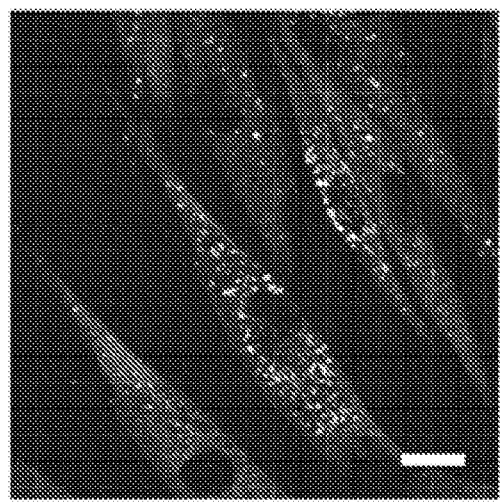
FIG. 16C is a diagram showing an image of LC3-stained NPC1 (HP-β-CD was added) in Test Example 8.
Figure 16D:
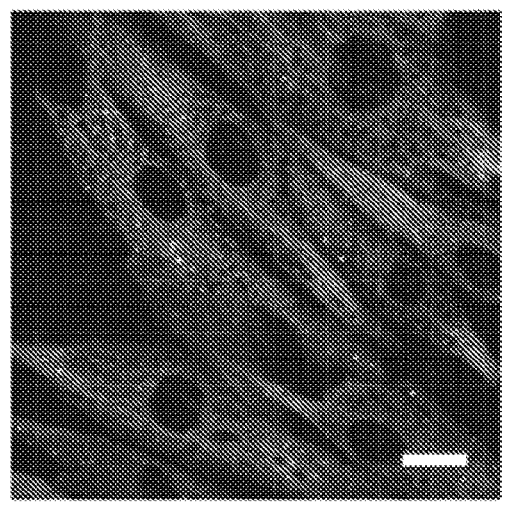
FIG. 16D is a diagram showing an image of LC3-stained NPC1 (HEE-SS-PRX was added) in Test Example 8.
Figure 16E:
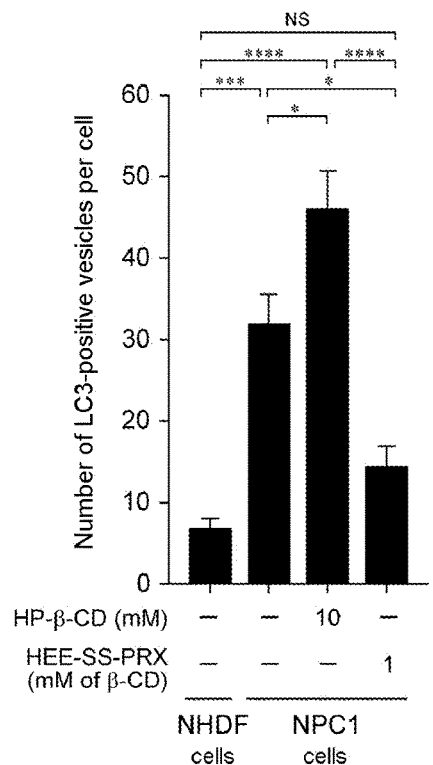
FIG. 16E is a graph showing results of the number of LC3-positive vesicles in a cell as determined in Test Example 8.

FIG. 16A to FIG. 16D show the images of LC3-stained cells, and FIG. 16E shows the quantitative results on the counts of intracellular LC3-positive vesicles.

FIG. 16A shows the result of the case where NHDF cells were used and none of the samples were added; FIG. 16B shows the result of the case where NPC1 cells were used and none of the samples were added; FIG. 16C shows the result of the case where NPC1 cells were used and HP-β-CD was added as a sample (amount added: 10 mM); FIG. 16D shows the result of the case where NPC1 cells were used and HEE-SS-PRX was added as a sample (amount added: amount equivalent to 1 mM concentration of β-CD on HEE-SS-PRX).

In FIG. 16E, in order from the left, the results on the following are shown: "the case where NHDF cells were used and none of the samples were added", "the case where NPC1 cells were used and HP-β-CD was added as a sample (amount added: 10 mM)", "the case where NPC1 cells were used and HE-SS-PRX was added as a sample (amount added: amount equivalent to 1 mM concentration of β-CD on HEE-SS-PRX)".

As a result of quantifying the number of LC3-positive vesicles in a cell based on the LC3-stained images, it was found that NPC1 cells had significantly higher counts of LC3-positive vesicles in ground state as compared to NHDF cells (normal cell). Moreover, NPC1 cells contacted with HP-β-CD showed further increased counts of LC3-positive vesicles. On the other hand, it was revealed that NPC1 cells contacted with a polyrotaxane having disulfide linkages (HEE-SS-PRX) showed LC3-positive vesicle counts decreased to a level similar to that of normal cells.

Test Example 9: Evaluation of LC3 and p62 Expressions

The expressions of LC3 and p62 in the following cells were assayed by Western blotting as follows.
<Cells>
(1) NPC1 cells
(2) NHDF cells
(3) NPC disease patient-derived NPC2 mutant dermal fibroblasts (obtained from Coriell Institute; number: GM18455)
(4) Fabry disease patient-derived dermal fibroblasts (obtained from Coriell Institute; number: GM00107)
(5) GM1 gangliosidosis patient-derived dermal fibroblasts (obtained from Coriell Institute; number: GM03589)

The cells were seeded on a 12-well plate (Nunc) (cell count: $1 \times 10^5$ cells/well), and incubated at 37° C. under a 5% $CO_2$ atmosphere for one day, followed by the addition of the following samples and another 24-hour incubation.

After the culturing, the cells were washed with PBS, and then 150 μL of RIPA buffer (Wako) containing 1% protease inhibitor cocktail (Nacalai Tesque) and 1% Phosphatase inhibitor cocktail (Nacalai Tesque) was added, and the cells were lysed by shaking for 30 minutes. The cell lysate was centrifuged for 10 minutes at 15,000 rpm, and the supernatant was collected.

10 μL of the supernatant and 2.5 μL of Laemmli buffer (Bio-Rad) were mixed, and applied to a 12% acrylamide gel. Then, electrophoresis was performed at 150V for 45 minutes. Then, proteins were transferred to a polyvinylidene fluoride (PVDF) membrane (Bio-Rad) using trans-blot Turbo Blotting System (Bio-Rad). Then, blocking was carried out with 5% skim milk solution (Wako) for an hour.

After the blocking treatment, PVDF membranes were treated at 4° C. for one day with an antibody against LC3 which is an indicator of autophagy (purchased from MBL), an antibody against p62/SQSTM1 which is a selective autophagy substrate (purchased from MBL), and an anti-β-actin antibody (Sigma-Aldrich), each diluted with 1% skim milk solution.

After three washes with PBS, the PVDF membranes were treated for 1 hour at room temperature with HRP-conjugated goat anti-rabbit IgG diluted in 1% skim milk solution.

After three washes with PBS, the PVDF membranes were treated with Pierce Western Blotting Substrate, and the images were taken with ImageQuant LAS 500 system (GE Healthcare Bioscience).

For comparison, the following cases were also examined in a similar manner: a case where NHDF cells were used and none of the samples were added; a case where NHDF cells were used and Bafilomycin A1 (hereinafter, referred to as "Baf A") was added instead of the sample; a case where NPC1 cells were used and none of the samples were added; and a case where NPC1 cells were used and Baf A was added instead of the sample.
<Samples>
(1) HEE-SS-PRX (produced in Preparation Example 5; the amount added was equivalent to 0.01 mM to 1 mM of β-CD on HEE-SS-PRX)
(2) HP-β-CD (Sigma-Aldrich; the amount added was 0.1 mM to 10 mM)

Figure 17A:
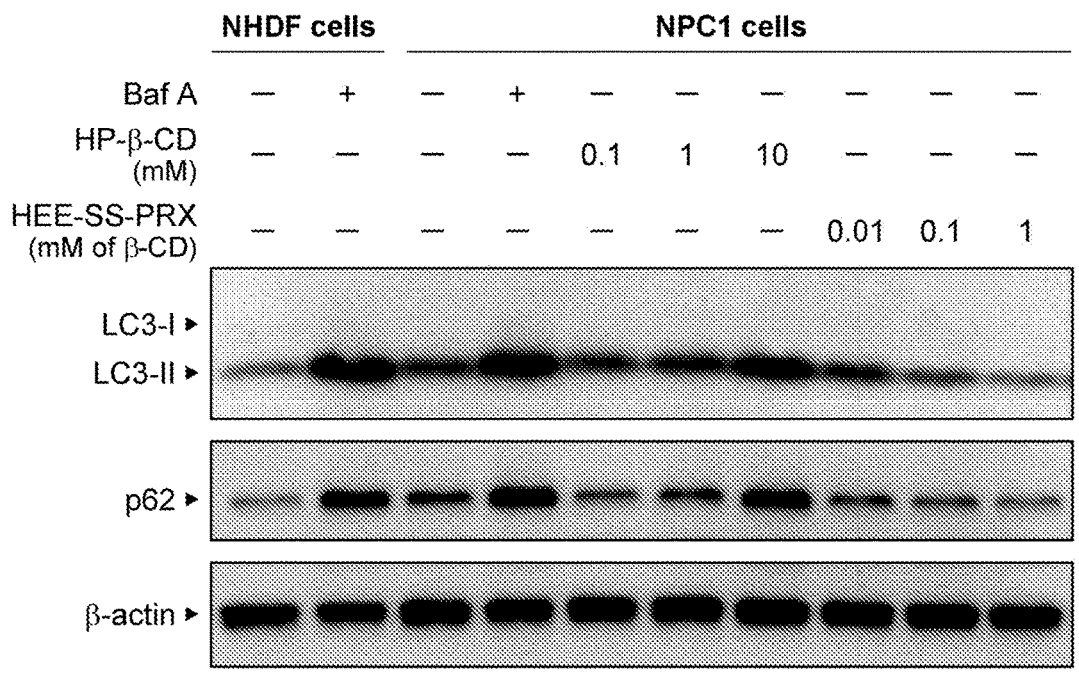
FIG. 17A is a diagram showing results of Western blotting of NHDF and NPC1 in Test Example 9.
Figure 17B:
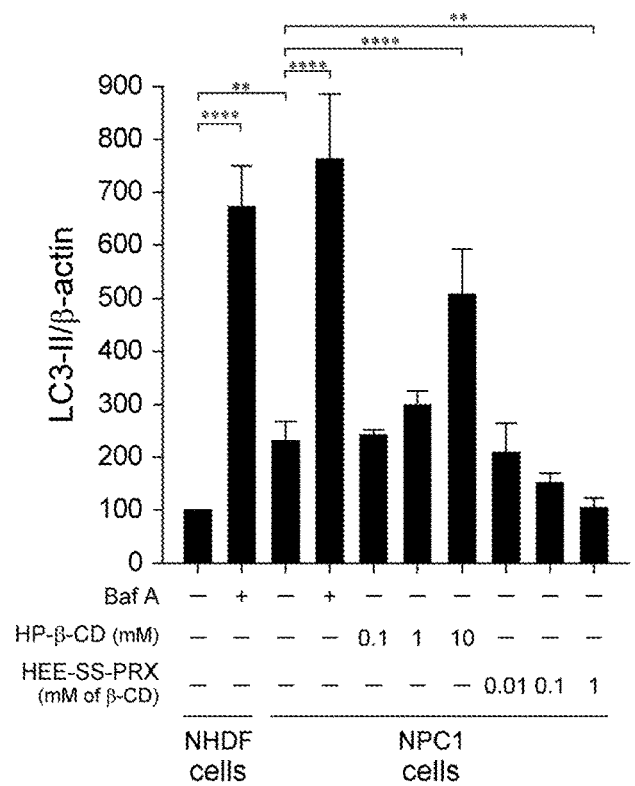
FIG. 17B is a graph showing the relative expression level of LC3-II in NHDF and NPC1 in Test Example 9.
Figure 17C:
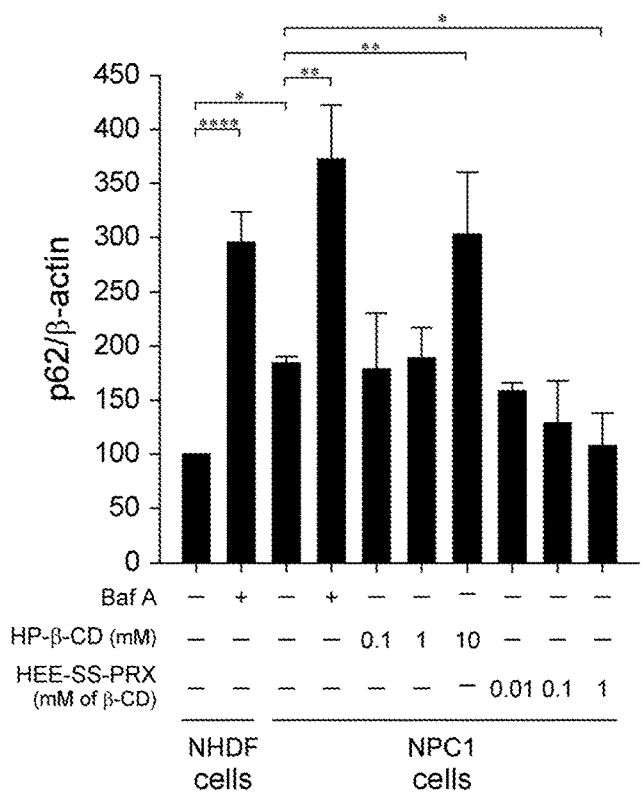
FIG. 17C is a graph showing the relative expression level of p62 in NHDF and NPC1 in Test Example 9.

FIG. 17A shows the results of Western blot of NHDF and NPC1, FIG. 17B shows the relative expression level of LC3-II in NHDF and NPC1, and FIG. 17C shows the relative expression level of p62 in NHDF and NPC1.

Figure 17D:
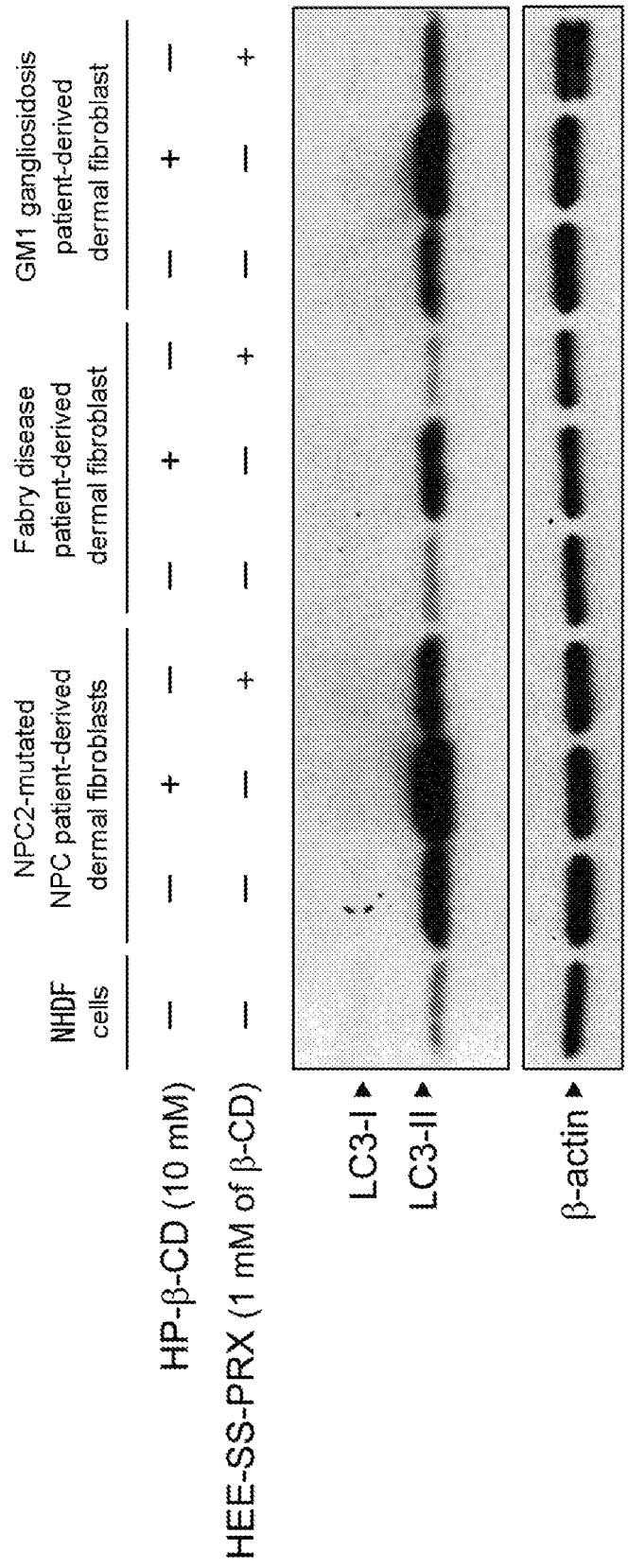
FIG. 17D is a diagram showing results of Western blotting of Test Example 9 with respect to NHDF, NPC2-mutated NPC disease patient-derived dermal fibroblast, Fabry disease patient-derived dermal fibroblast, and GM1 gangliosidosis patient-derived dermal fibroblast.
Figure 17E:
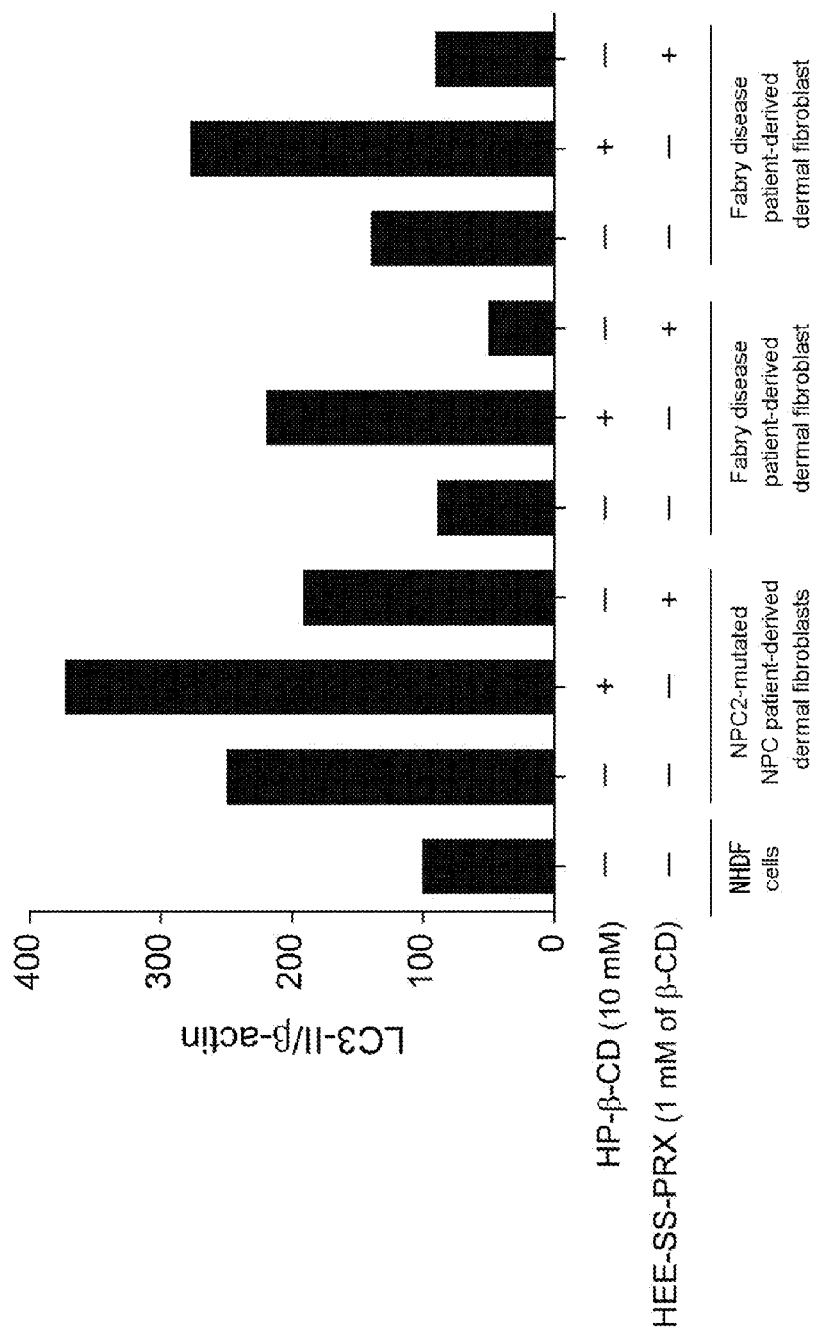
FIG. 17E is a diagram showing the relative expression level of LC3-II in Test Example 9 with respect to NHDF, NPC2-mutated NPC disease patient-derived dermal fibroblast, Fabry disease patient-derived dermal fibroblast, and GM1 gangliosidosis patient-derived dermal fibroblast.

Moreover, FIG. 17D shows the results of Western blotting for NHDF, NPC2-mutated NPC disease patient-derived dermal fibroblast, Fabry disease patient-derived dermal fibroblast, and GM1 gangliosidosis patient-derived dermal fibroblast, and FIG. 17E shows the relative expression levels of LC3-II in NHDF, NPC2-mutated NPC disease patient-derived dermal fibroblast, Fabry disease patient-derived dermal fibroblast, and GM1 gangliosidosis patient-derived dermal fibroblast.

Each of the relative expression levels was determined from the intensity of Western blot band.

FIG. 17A, FIG. 17B, and FIG. 17C show, in order from the left, the results for "the case where NHDF cells were used and none of the samples were added", "the case where NHDF cells were used and Baf A was added instead of a sample", "the case where NPC1 cells were used and none of the samples were added", "the case where NPC1 cells were used and Baf A was added instead of a sample", "the case where NPC1 cells were used and 0.1 mM HP-β-CD was added as a sample", "the case where NPC1 cells were used and 1 mM HP-β-CD was added as a sample", "the case where NPC1 cells were used and 10 mM HP-β-CD was added as a sample", "the case where NPC1 cells were used and 0.01 mM HEE-SS-PRX was added as a sample", "the case where NPC1 cells were used and 0.1 mM HEE-SS-PRX was added as a sample", and "the case where NPC1 cells were used and 1 mM HEE-SS-PRX was added as a sample".

FIG. 17D and FIG. 17E show, in order from the left, the results for "the case where NHDF cells were used and none of the samples were added", "the case where NPC2-mutated NPC disease patient-derived dermal fibroblasts were used and none of the samples were added", "the case where NPC2-mutated NPC disease patient-derived dermal fibroblasts were used and 10 mM HP-β-CD was added as a sample", "the case where NPC2-mutated NPC disease patient-derived dermal fibroblasts were used and 1 mM HEE-SS-PRX was added as a sample", "the case where Fabry disease patient-derived dermal fibroblasts were used and none of the samples were added", "the case where Fabry disease patient-derived dermal fibroblasts were used and 10 mM HP-β-CD was added as a sample", "the case where Fabry disease patient-derived dermal fibroblasts were used and 1 mM HEE-SS-PRX was added as a sample", "the case where GM1 gangliosidosis patient-derived dermal fibroblasts were used and none of the samples were added", "the case where GM1 gangliosidosis patient-derived dermal fibroblasts were used and 10 mM HP-β-CD was added as a sample", and "the case where GM1 gangliosidosis patient-derived dermal fibroblasts were used and 1 mM HEE-SS-PRX was added as a sample".

The results of FIG. 17A to FIG. 17C demonstrate significant increases of LC3 and p62 by the addition of Baf A that is known to neutralize the low pH in lysosomes and induce an impaired autophagic flux. Also, it was shown that the addition of HP-β-CD increased the expression of LC3-II in a concentration dependent manner, and at the concentration of 10 mM, p62 was also significantly increased.

On the other hand, the addition of HEE-SS-PRX (polyrotaxane having intracellularly degradable linkages) did not increase the expression levels of LC3-II and p62. Moreover, the relative expression level as determined from the band intensity indicated a concentration dependent decrease in LC3-II expression level.

Moreover, the results shown in FIG. 17D and FIG. 17E show that the addition of HP-β-CD resulted in an increase in LC3-II while the addition of HEE-SS-PRX reduced LC3-II even in NPC2-mutated NPC disease patient-derived dermal fibroblasts, Fabry disease patient-derived dermal fibroblasts, and GM1 gangliosidosis patient-derived dermal fibroblasts, which are known to have an impaired autolysosome formation.

The effects of HP-β-CD and HEE-SS-PRX on increase and decrease of intracellular LC3-II level were universal and not dependent on the cell type, and HP-β-CD resulted in the intracellular accumulation of LC3-II while HEE-SS-PRX eliminated the accumulation of LC3-II.

It was expected, from these results, that HP-β-CD inhibited the formation of autolysosomes, whereas polyrotaxanes having intracellularly degradable linkages promoted the formation of autolysosomes.

Test Example 10: Observation of Autolysosome Formation

The formation of autophagosomes and autolysosomes was evaluated, respectively, based on the fluorescent images obtained by utilizing EGFP which becomes quenched under acidic conditions, and linking LC3 to EGFP via mRFP which can be excited and emit fluorescence even under acidic conditions (S. Kimura et al. Autophagy 3, 452-260 (2007)). Specifically, the procedure was conducted as follows.

NPC1 cells were seeded on a 35 mm glass bottom dish (IWAKI) (cell count: $1.5 \times 10^4$ cells/dish), and incubated at 37° C. under a 5% $CO_2$ atmosphere for one day.

250 ng of ptfLC3 plasmid DNA containing mRFP-EGFP-LC3 in tandem (purchased from Addgene; no. 21074) was diluted in Opti-MEM (Life Technologies), mixed with Lipofectamine 3000 (Life Technologies), and allowed to stand for 5 minutes.

The plasmid-containing solution was added to the cell culture, and the cells were incubated for 24 hours. After replacing the culture medium, the following samples were added, and the cells were cultured for another 24 hours.

After the culturing, the cells were treated and fixed with 4% paraformaldehyde (Wako) for 10 minutes. After washing with PBS, the cells were observed with FluoView FV-10i (Olympus).

For comparison, similar assays were performed for the case where NHDF was not contacted with any sample, and for the case where NPC1 was not contacted with any sample.
<Samples>
(1) HEE-SS-PRX (produced in Preparation Example 5; the amount added was equivalent to 1 mM of cyclodextrin concentration)
(2) HP-β-CD (Sigma-Aldrich; the amount added was 10 mM)

Figure 18A:
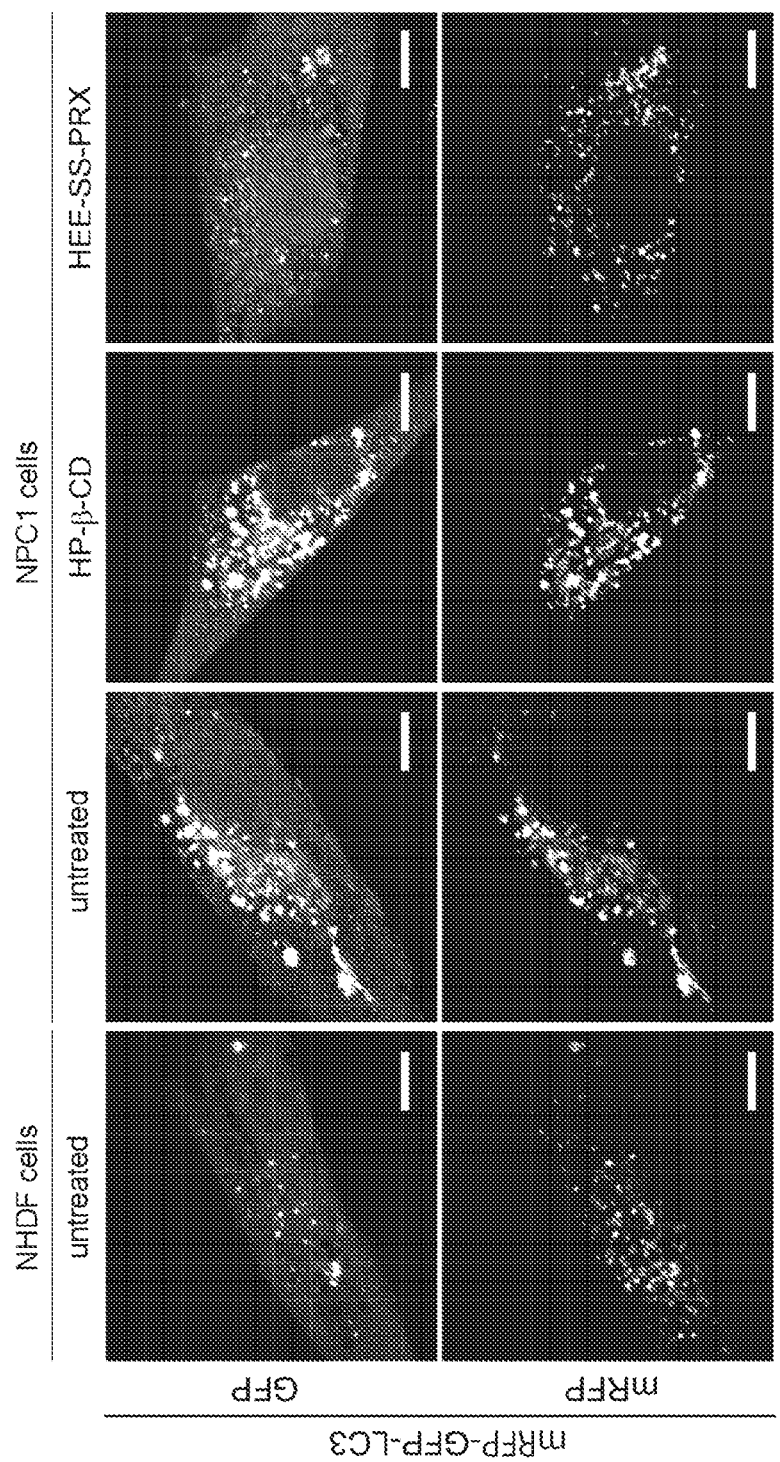
FIG. 18A is a diagram showing a fluorescent microscope image of each cell in Test Example 10.
Figure 18B:
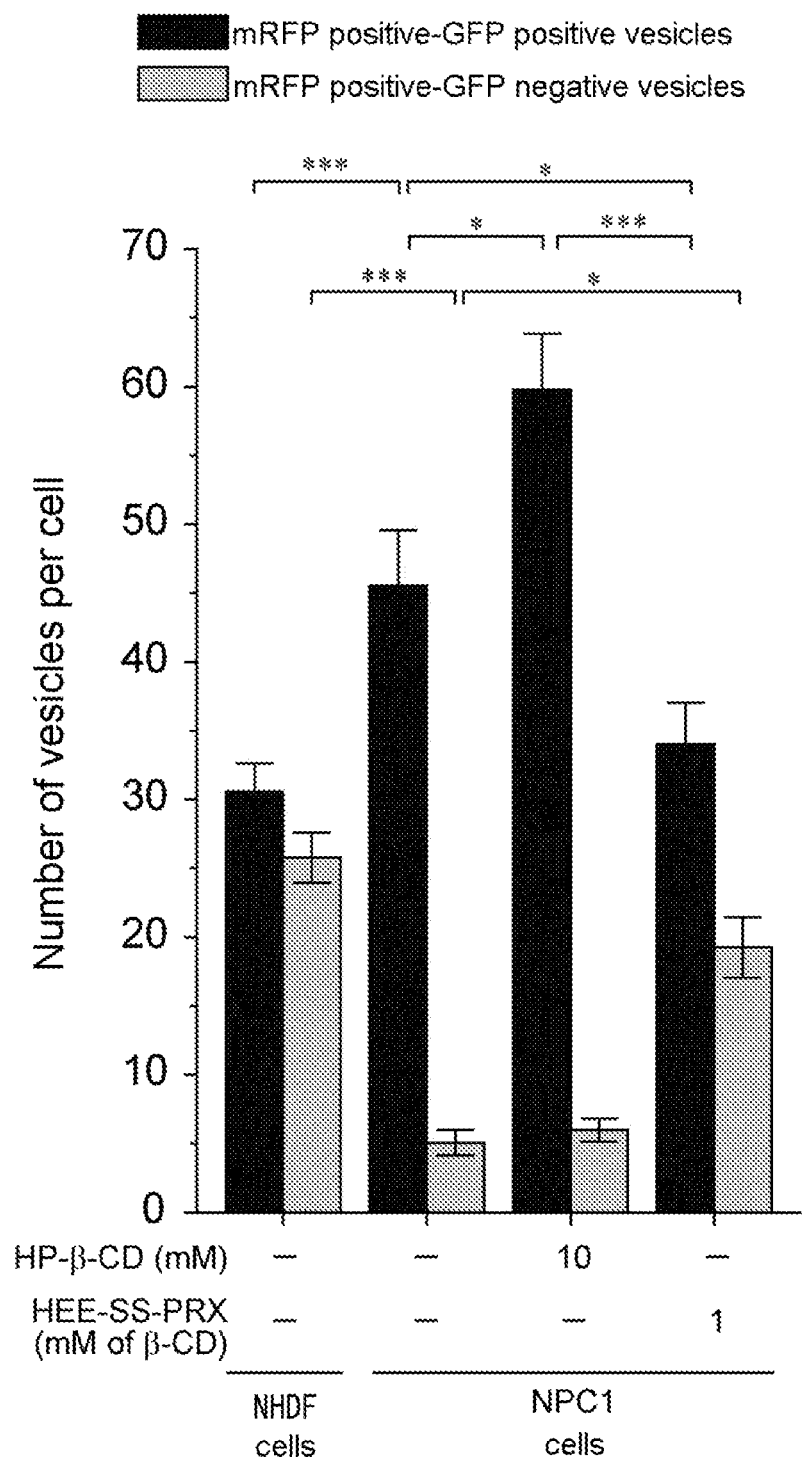
FIG. 18B is a graph showing results of the number of autophagosomes and the number of autolysosomes in each cell analyzed in Test Example 10.

FIG. 18A shows the expression of ptfLC3 in each of the cells observed by fluorescence microscopy, and FIG. 18B shows the image analysis of the number of autophagosomes and the number of autolysosomes.

FIG. 18A shows, in order from the left, the results for "the case where NHDF cells were used and none of the samples were added", "the case where NPC1 cells were used and none of the samples were added", "the case where NPC1 cells were used and HP-β-CD was added as a sample", "the case where NPC1 cells were used and HEE-SS-PRX was added as a sample", and the upper row shows the images generated by "GFP" and the lower row shows the images generated by "mRFP".

FIG. 18B shows, in order from the left, the results for "the case where NHDF cells were used and none of the samples were added", "the case where NPC1 cells were used and none of the samples were added", "the case where NPC1 cells were used and HP-β-CD was added as a sample", "the case where NPC1 cells were used and HEE-SS-PRX was added as a sample", and the left bars for each condition indicate the results for the number of autophagosomes and the right bars indicate the results for the number of autolysosomes.

The results of FIG. 18A and FIG. 18B demonstrated an increase in the number of autophagosomes and a decrease in the number of autolysosomes in untreated NPC1 cells as compared to untreated normal fibroblasts.

The NPC1 cells treated with HP-β-CD showed an increase in the number of autophagosomes with no change in the number of autolysosomes.

On the other hand, the NPC1 cells treated with HEE-SS-PRX showed nearly the same number of autophagosomes and autolysosomes as the normal cells, demonstrating that the impaired formation of autolysosomes in NPC1 cells could be ameliorated by the addition of polyrotaxanes having intracellularly degradable linkages.

Test Example 11: Observation of the Fusion of Autophagosomes and Lysosomes

To examine the formation of autolysosomes in more detail, the localization of mRFP-LC3 transiently expressed from plasmid DNA and the localization of LAMP1 which is a lysosomal-specific membrane protein were observed as follows.

NPC1 cells were seeded on a 35 mm glass bottom dish (IWAKI) (cell count: $1.5 \times 10^4$ cells/dish), and incubated at 37° C. under a 5% $CO_2$ atmosphere for one day.

250 ng of mRFP-LC3 expression plasmid DNA (purchased from Addgene; no. 21075) was diluted in Opti-MEM (Life Technologies), mixed with Lipofectamine 3000 (Life Technologies), and allowed to stand for 5 minutes.

The plasmid-containing solution was added to the cell culture, and the cells were incubated for 24 hours. After replacing the culture medium, the following samples were added, and the cells were cultured for another 24 hours.

After the culturing, the cells were treated and fixed with 4% paraformaldehyde (Wako) for 10 minutes, treated with 50 µg/ml digitonin (Tokyo Chemical Industry) for 5 minutes to permeabilize the plasma membrane, and blocked with 1% BSA/PBS solution for 30 minutes.

The cells were then treated with a mouse monoclonal anti-LAMP1 antibody (Santa Cruz) diluted to 1:200 with 1% BSA for one day at 4° C. After washing with PBS, the cells were stained with an Alexa Fluor 488-conjugated goat anti-mouse IgG (Abcam) (diluted to 1:1,000 with 1% BSA) for 30 minutes. After washing with PBS, the cells were observed with FluoView FV-10i (Olympus) to evaluate co-localization rate of mRFP-LC3 and LAMP1.

For comparison, similar assays were performed for the case where NHDF was contacted with no sample, and for the case where NPC1 was contacted with no sample.

<Samples>
(1) HEE-SS-PRX (produced in Production Example 5; the amount added was equivalent to 1 mM of cyclodextrin concentration)
(2) HP-β-CD (Sigma-Aldrich; the amount added was 10 mM)

Figure 19A:
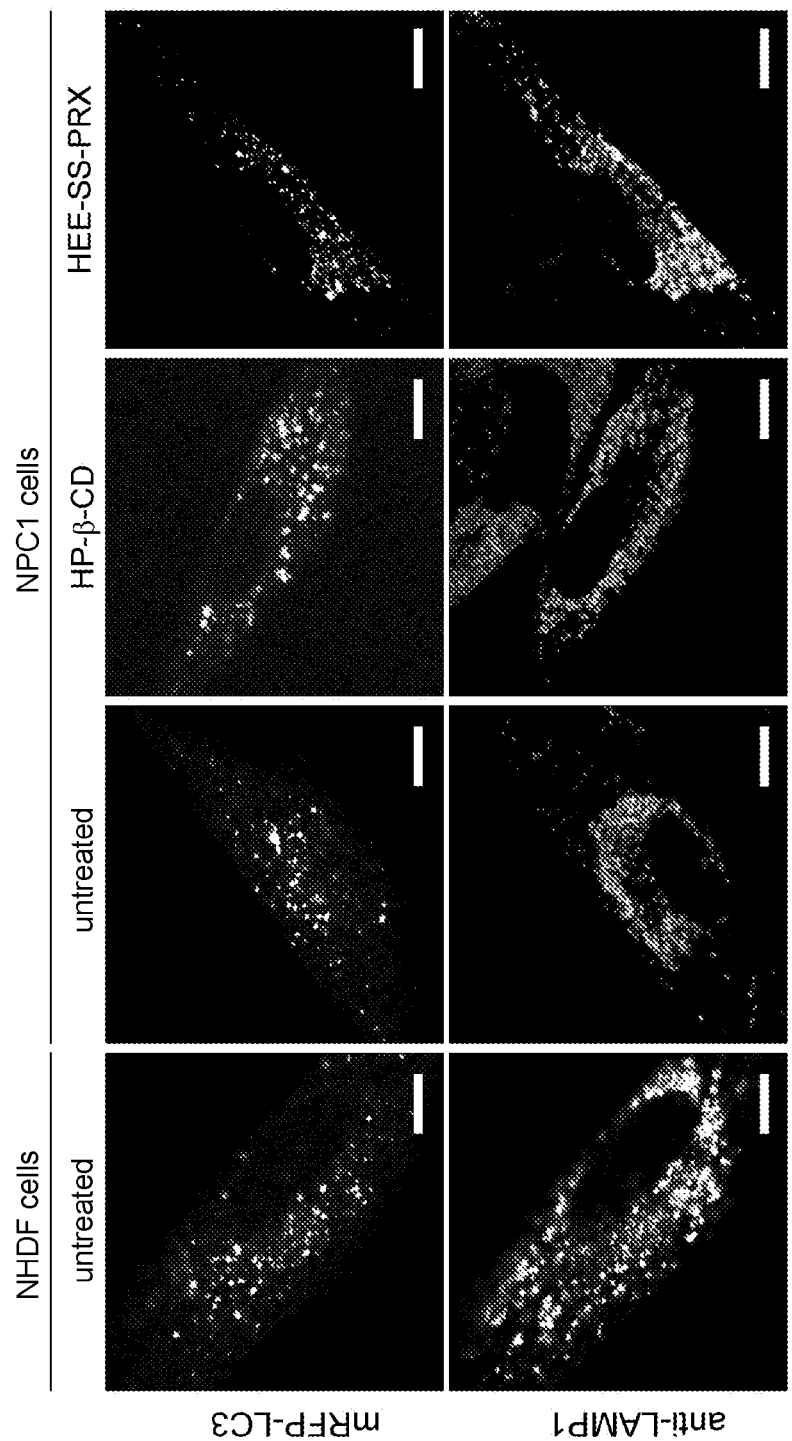
FIG. 19A is a diagram showing a microscope image of each cell in Test Example 11.
Figure 19B:
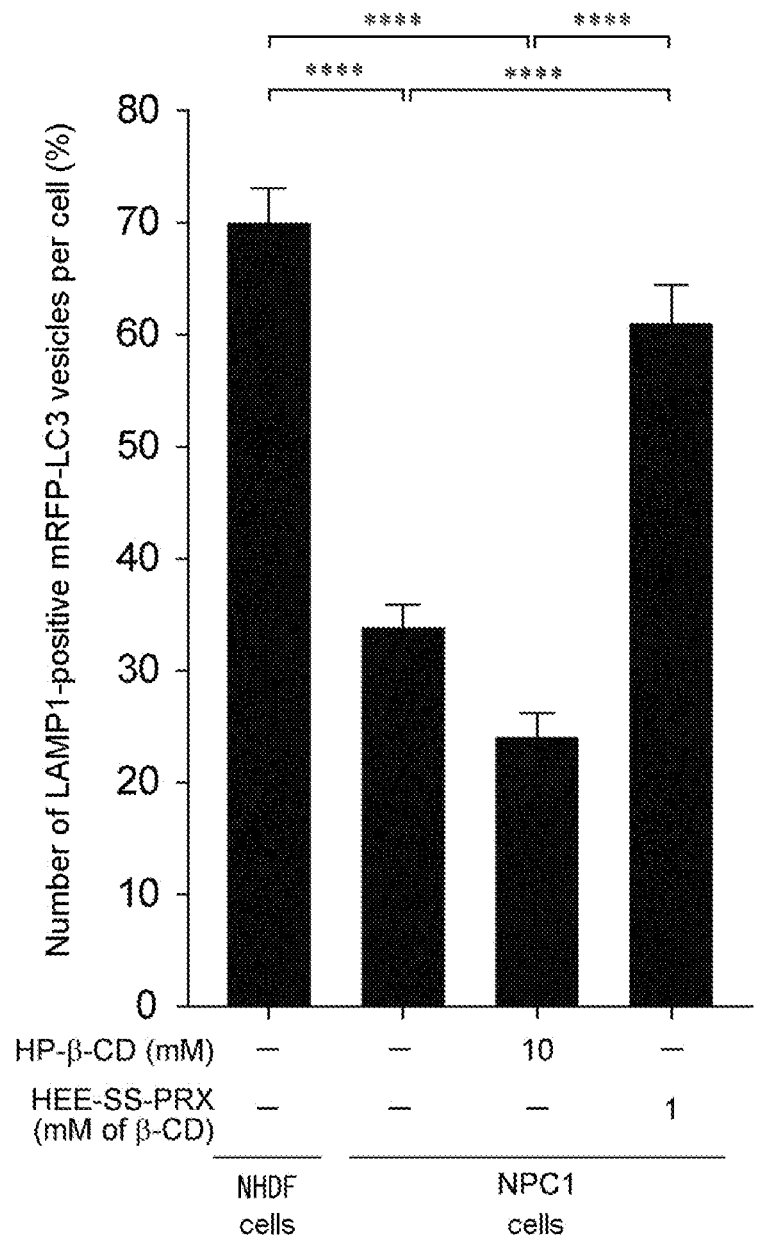
FIG. 19B is a graph showing results obtained for co-localization rate of mRFP-LC3 and anti-LAMP1 antibody in each cell of Test Example 11.

FIG. 19A shows the results for the expression of mRFP-LC3 and LAMP1 in each cell, and FIG. 19B shows the results for the colocalization rate of mRFP-LC3 and LAMP1.

FIG. 19A shows, in order from the left, the results for "the case where NHDF cells were used and none of the samples were added", "the case where NPC1 cells were used and none of the samples were added", "the case where NPC1 cells were used and HP-β-CD was added as a sample", "the case where NPC1 cells were used and HEE-SS-PRX was added as a sample", and the upper row shows the observations of the expression of "mRFP-LC3" and the lower row shows the observations the localization of endogenous "LAMP1".

FIG. 19B shows, in order from the left, the results for "the case where NHDF cells were used and none of the samples were added", "the case where NPC1 cells were used and none of the samples were added", "the case where NPC1 cells were used and HP-β-CD was added as a sample", "the case where NPC1 cells were used and HEE-SS-PRX was added as a sample". The vertical axis in FIG. 19B indicates the co-localization ratio of mRFP-LC3 and LAMP1 in the cells.

The results of FIG. 19A and FIG. 19B suggest that the formation of autolysosomes is inhibited in untreated NPC1 cells, as the co-localization rate of mRFP-LC3 and LAMP1 was low as compared to untreated normal fibroblasts.

Moreover, similar to untreated NPC1 cells, the co-localization rate of the mRFP-LC3 and LAMP1 was low in HP-β-CD-treated NPC1 cells.

On the other hand, the co-localization rate of mRFP-LC3 and LAMP1 in NPC1 cells treated with HEE-SS-PRX was increased to the level comparable to that of normal cells, suggesting an enhanced autolysosome formation.

The results of Test Examples 8 to 11 reveal that polyrotaxanes having a plurality of cyclic molecules threaded by a linear molecule that is linked to bulky substituent groups via intracellularly degradable linkages at both ends show an activity to enhance the autolysosome formation. Therefore, an application as a pharmaceutical agent for treating a disease caused by autophagy dysfunction due to impaired autolysosome formation is expected for the polyrotaxanes of the present invention.

Embodiments of the present invention include, for example, the following.

<1> A pharmaceutical composition for a disease caused by at least any one of lipid metabolism disorders and autophagy dysfunctions, comprising a polyrotaxane having a plurality of cyclic molecules threaded by a linear molecule, wherein the linear molecule is linked to bulky substituents via intracellularly degradable linkages at both ends.

<2> The pharmaceutical composition according to above <1>, wherein the disease caused by at least any one of lipid metabolism disorders and autophagy dysfunctions is a lysosomal disease.

<3> The pharmaceutical composition according to any one of above <1> to <2>, wherein the cyclic molecule is a cyclodextrin.

<4> The pharmaceutical composition according to any one of above <1> to <3>, wherein the intracellularly degradable linkage is any one selected from an acetal linkage, a ketal linkage, a disulfide linkage, an ester linkage, an ortho-ester linkage, a vinylether linkage, and a hydrazide linkage.

<5> The pharmaceutical composition according to any one of above <1> to <4>, wherein the linear molecule is any one of a copolymer of polyethylene glycol and polypropylene glycol, polypropylene glycol, and polyethylene glycol.

<6> The pharmaceutical composition according to any one of above <2> to <5>, wherein the lysosomal disease is any one selected from Gaucher's disease, Niemann-Pick disease type A, Niemann-Pick disease type B, Niemann-Pick disease type C, GM1 gangliosidosis, GM2 gangliosidosis, Farber disease, Wolman disease, and Fabry disease.

<7> The pharmaceutical composition according to any one of above <2> to <6>, wherein the lysosomal disease is any one selected from Niemann-Pick disease type C, GM1 gangliosidosis, and Fabry disease.

<8> A polyrotaxane comprising a plurality of cyclic molecules threaded by a linear molecule,
wherein the linear molecule is linked to bulky substituents via intracellularly degradable linkages at both ends,
wherein the linear molecule is a copolymer composed of polyethylene glycol and polypropylene glycol in the order of polyethylene glycol-polypropylene glycol-polyethylene glycol, and
wherein the plurality of cyclic molecules are β-cyclodextrins.

<9> The polyrotaxane according to above <8>, wherein the intracellularly degradable linkage is any one selected from an acetal linkage, a ketal linkage, a disulfide linkage, an ester linkage, an ortho-ester linkage, a vinylether linkage, and a hydrazide linkage.

<10> A method for prevention or treatment of a disease caused by at least any one of lipid metabolism disorders and autophagy dysfunctions, the method comprising administering to an individual the pharmaceutical composition according to any one of above <1> to <7>.

<11> A use of the pharmaceutical composition according to any one of above <1> to <7> for prevention or treatment of a disease caused by at least any one of lipid metabolism disorders and autophagy dysfunctions.

<12> A use of the pharmaceutical composition according to above <8> or <9> in the manufacture of a medicament for prevention or treatment of a disease caused by at least any one of lipid metabolism disorders and autophagy dysfunctions.

INDUSTRIAL APPLICABILITY

The pharmaceutical composition of the present invention, which includes a polyrotaxane, is not only safer than conventional cyclodextrin alone since hemolysis can be avoided, but also shows a superior cholesterol removal activity by specifically releasing cyclodextrins inside the cells. The pharmaceutical composition of the present invention also shows an excellent enhancing activity on the formation of autolysosomes. Due to these activities, it has a high therapeutic or prophylactic effect, and can be used as an excellent pharmaceutical composition with less side effects. Moreover, since the pharmaceutical composition of the present invention, which includes a polyrotaxane, has a higher molecular weight than cyclodextrin, it is expected to have a persistent efficacy due to extended blood half-life, as well as a reduction in the dose or number of doses.

What is claimed is:

1. A method of treatment of Niemann-Pick disease type C, the method comprising administering to a subject a pharmaceutical composition comprising a polyrotaxane having a plurality of cyclic molecules threaded by a linear molecule, wherein the linear molecule is linked to bulky substituents via intracellularly degradable linkages at both ends, wherein the plurality of cyclic molecules are β-cyclodextrins, wherein the β-cyclodextrin has a primary hydroxyl group linked to a substituent via carbamic acid ester, and wherein the substituent is a hydroxyethoxy ethyl group.

2. The method according to claim 1, wherein the intracellularly degradable linkage is selected from the group consisting of an acetal linkage, a ketal linkage, a disulfide linkage, an ester linkage, an ortho-ester linkage, a vinylether linkage, and a hydrazide linkage.

3. The method according to claim 1, wherein the linear molecule is selected from the group consisting of a copolymer of polyethylene glycol and polypropylene glycol, polypropylene glycol, and polyethylene glycol.

4. The method according to claim 1, wherein the intracellularly degradable linkage is selected from the group consisting of an acetal linkage, a disulfide linkage, and an ester linkage.

5. The method according to claim 4, wherein the intracellularly degradable linkage is selected from the group consisting of an acetal linkage and a disulfide linkage.

6. The method according to claim 1, wherein the subject is a human being.

7. The method according to claim 1, wherein the pharmaceutical composition is administered intracerebroventricularly.

8. The method according to claim 1, wherein the polyrotaxane having a plurality of cyclic molecules threaded by a linear molecule is represented by Structural Formula (6):

Structural Formula (6)

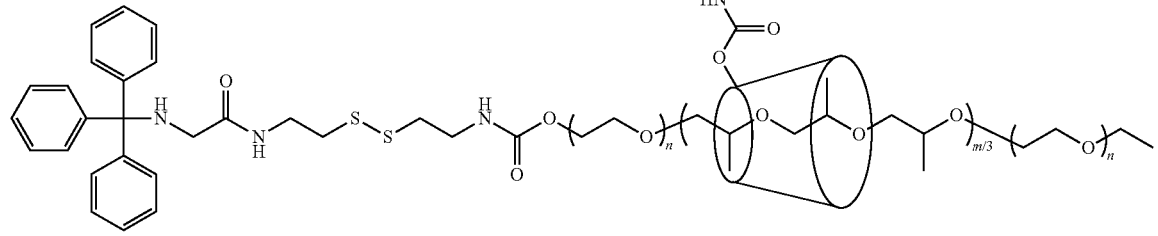

wherein m and n independently represent the number of repetitive units, and wherein the plurality of cyclic molecules have a structure represented by Formula (C):

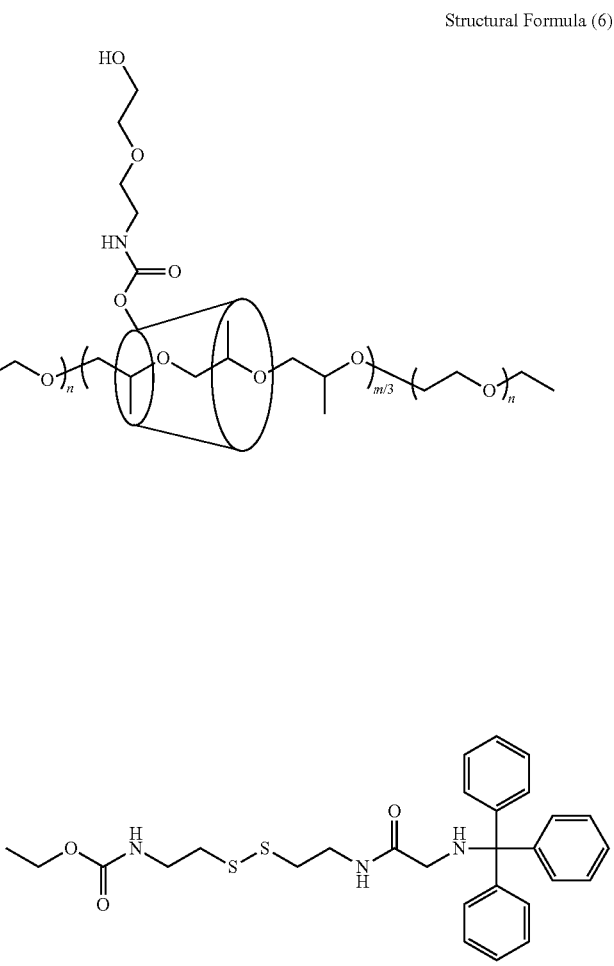

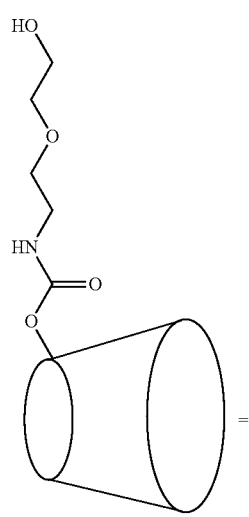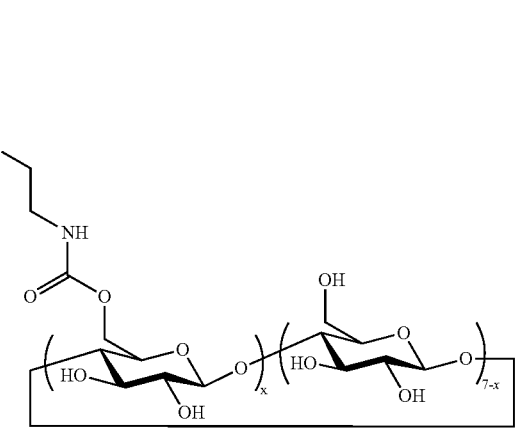
Formula (C)
wherein x is a number from 1 to 7.
9. The method according to claim 1, wherein the intracellularly degradable linkage is a disulfide linkage.
* * * * *